US007491534B2

(12) United States Patent
Collas et al.

(10) Patent No.: US 7,491,534 B2
(45) Date of Patent: Feb. 17, 2009

(54) METHODS FOR ALTERING CELL FATE TO GENERATE T-CELLS SPECIFIC FOR AN ANTIGEN OF INTEREST

(75) Inventors: Philippe Collas, Oslo (NO); James M. Robl, Brandon, SD (US); Bjorn Steen Skalhegg, Blommenholm (NO)

(73) Assignee: Kirin Holdings Kabushiki Kaisha, Tokyo (JP)

( * ) Notice: Subject to any disclaimer, the term of this patent is extended or adjusted under 35 U.S.C. 154(b) by 840 days.

(21) Appl. No.: 10/426,595

(22) Filed: Apr. 30, 2003

(65) Prior Publication Data

US 2004/0072288 A1    Apr. 15, 2004

Related U.S. Application Data

(63) Continuation of application No. PCT/US03/08120, filed on Mar. 14, 2003, which is a continuation-in-part of application No. 10/015,824, filed on Dec. 10, 2001, now abandoned.

(60) Provisional application No. 60/376,653, filed on Apr. 30, 2002, now abandoned, provisional application No. 60/258,152, filed on Dec. 22, 2000, now abandoned.

(51) Int. Cl.
  *C12N 5/10*  (2006.01)
  *C12N 5/08*  (2006.01)
  *C12N 5/00*  (2006.01)
  *C12N 15/00*  (2006.01)

(52) U.S. Cl. ............... 435/377; 435/455; 435/357; 435/366; 435/372.3

(58) Field of Classification Search ............... 435/377, 435/455, 357, 366, 372.3
See application file for complete search history.

(56) References Cited

U.S. PATENT DOCUMENTS

| | | | |
|---|---|---|---|
| 4,873,316 A | 10/1989 | Meade et al. ............... 530/412 |
| 4,959,317 A | 9/1990 | Sauer ....................... 435/172.3 |
| 4,994,384 A | 2/1991 | Prather et al. ............ 435/172.2 |
| 5,057,420 A | 10/1991 | Massey ..................... 435/172.2 |
| 5,096,822 A | 3/1992 | Rosenkrans, Jr. |
| 5,160,312 A | 11/1992 | Voelkel ....................... 600/34 |
| 5,175,384 A | 12/1992 | Krimpenfort et al. .......... 800/2 |
| 5,213,979 A | 5/1993 | First et al. ................ 435/240.2 |
| 5,240,840 A | 8/1993 | Feinberg et al. ........... 435/172.3 |
| 5,434,066 A | 7/1995 | Bebee et al. .............. 435/172.3 |
| 5,434,340 A | 7/1995 | Krimpenfort et al. .......... 800/2 |
| 5,453,366 A | 9/1995 | Sims et al. ............... 435/172.3 |
| 5,464,764 A | 11/1995 | Capecchi et al. .......... 435/172.3 |
| 5,470,560 A | 11/1995 | Martin, Jr. .................. 424/9.2 |
| 5,480,772 A | 1/1996 | Wangh ......................... 435/2 |
| 5,482,856 A | 1/1996 | Fell, Jr. et al. ............ 435/320.1 |
| 5,487,992 A | 1/1996 | Capecchi et al. .......... 435/172.3 |
| 5,496,720 A | 3/1996 | Susko-Parrish et al. .. 435/240.2 |
| 5,527,674 A | 6/1996 | Guerra et al. ................. 435/6 |
| 5,545,806 A | 8/1996 | Lonberg et al. ................ 800/2 |
| 5,545,807 A | 8/1996 | Surani et al. .................. 800/2 |
| 5,565,350 A | 10/1996 | Kmiec ...................... 435/172.3 |
| 5,565,362 A | 10/1996 | Rosen ...................... 435/320.1 |
| 5,569,825 A | 10/1996 | Lonberg et al. ................ 800/2 |
| 5,583,016 A | 12/1996 | Villeponteau et al. ....... 435/91.3 |
| 5,591,669 A | 1/1997 | Krimpenfort et al. .......... 800/2 |
| 5,612,205 A | 3/1997 | Kay et al. ................. 435/172.3 |
| 5,614,396 A | 3/1997 | Bradley et al. ............ 435/172.3 |
| 5,625,126 A | 4/1997 | Lonberg et al. ................ 800/2 |
| 5,627,059 A | 5/1997 | Capecchi et al. .......... 435/172.3 |
| 5,631,153 A | 5/1997 | Capecchi et al. .......... 435/172.3 |
| 5,633,076 A | 5/1997 | DeBoer et al. ............ 435/172.3 |
| 5,633,425 A | 5/1997 | Lonberg et al. ................ 800/2 |
| 5,639,457 A | 6/1997 | Brem et al. ............... 424/184.1 |
| 5,651,992 A | 7/1997 | Wangh ....................... 424/520 |
| 5,654,182 A | 8/1997 | Wahl et al. ................ 435/172.1 |
| 5,654,183 A | 8/1997 | Anderson et al. ......... 435/172.3 |
| 5,661,016 A | 8/1997 | Lonberg et al. ........... 435/172.3 |
| 5,677,177 A | 10/1997 | Wahl et al. .................. 435/325 |
| 5,679,523 A | 10/1997 | Li et al. ......................... 435/6 |
| 5,695,977 A | 12/1997 | Jurka ....................... 435/172.3 |
| 5,698,763 A | 12/1997 | Weissmann et al. ............ 800/2 |
| 5,721,367 A | 2/1998 | Kay et al. ...................... 800/2 |
| 5,733,730 A | 3/1998 | De Lange ....................... 435/6 |
| 5,741,957 A | 4/1998 | Deboer et al. .................. 800/2 |
| 5,750,172 A | 5/1998 | Meade et al. ............... 426/580 |

(Continued)

FOREIGN PATENT DOCUMENTS

EP    0546073    9/1997

(Continued)

OTHER PUBLICATIONS

Hall et al. (1991) Int. Immunol., vol. 3(4), 359-368.*

(Continued)

*Primary Examiner*—Anne Marie S Wehbe
(74) *Attorney, Agent, or Firm*—Clark & Elbing LLP; Karen L. Elbing

(57) ABSTRACT

The invention provides methods for altering the expression profile of a cell to convert the cell from one cell type to a desired cell type (e.g., T-cells). These reprogrammed cells may be used in a variety of medical applications for treating a mammal in need of a particular cell type.

7 Claims, 28 Drawing Sheets
(5 of 28 Drawing Sheet(s) Filed in Color)

U.S. PATENT DOCUMENTS

| | | | |
|---|---|---|---|
| 5,756,325 A | 5/1998 | Kmiec | 435/172.3 |
| 5,763,240 A | 6/1998 | Zarling et al. | 435/172.3 |
| 5,770,422 A | 6/1998 | Collins | 435/194 |
| 5,770,429 A | 6/1998 | Lonberg et al. | 435/240.2 |
| 5,773,217 A | 6/1998 | Wangh | 435/6 |
| 5,776,744 A | 7/1998 | Glazer et al. | 435/172.3 |
| 5,780,296 A | 7/1998 | Holloman et al. | 435/320.1 |
| 5,786,217 A | 7/1998 | Tubo et al. | 435/402 |
| 5,789,215 A | 8/1998 | Berns et al. | 435/172.3 |
| 5,789,650 A | 8/1998 | Lonberg et al. | 800/2 |
| 5,801,030 A | 9/1998 | McVey et al. | 435/172.3 |
| 5,814,318 A | 9/1998 | Lonberg et al. | 424/184.1 |
| 5,821,117 A | 10/1998 | Sandrin et al. | 435/172.3 |
| 5,827,690 A | 10/1998 | Meade et al. | 435/69.6 |
| 5,830,698 A | 11/1998 | Reff et al. | 435/69.1 |
| 5,837,857 A | 11/1998 | Villeponteau et al. | 536/24.31 |
| 5,843,643 A | 12/1998 | Ratner | 435/6 |
| 5,843,754 A | 12/1998 | Susko-Parrish et al. | 435/240 |
| 5,849,992 A | 12/1998 | Meade et al. | 800/2 |
| 5,874,299 A | 2/1999 | Lonberg et al. | 435/320.1 |
| 5,876,979 A | 3/1999 | Andrews et al. | 435/91.3 |
| 5,877,397 A | 3/1999 | Lonberg et al. | 800/2 |
| 5,905,042 A | 5/1999 | Stice et al. | 435/373 |
| 5,945,577 A | 8/1999 | Stice et al. | 800/24 |
| 5,952,222 A | 9/1999 | Rosenkrans, Jr. et al. | 435/325 |
| 5,994,619 A | 11/1999 | Stice et al. | |
| 6,001,654 A | 12/1999 | Anderson et al. | 435/377 |
| 6,011,197 A | 1/2000 | Strelchenko et al. | 800/24 |
| 6,023,010 A | 2/2000 | Krimpenfort et al. | 800/2 |
| 6,077,710 A | 6/2000 | Susko-Parrish et al. | 435/375 |
| 6,107,543 A | 8/2000 | Sims et al. | 800/21 |
| 6,147,276 A | 11/2000 | Campbell et al. | |
| 6,153,428 A | 11/2000 | Gustafsson et al. | 435/325 |
| 6,194,202 B1 | 2/2001 | Susko-Parrish et al. | 435/325 |
| 6,204,061 B1 | 3/2001 | Capecchi et al. | 435/463 |
| 6,211,429 B1 | 4/2001 | Machaty et al. | 800/24 |
| 6,215,041 B1 | 4/2001 | Stice et al. | |
| 6,235,969 B1 | 5/2001 | Stice et al. | |
| 6,235,970 B1 | 5/2001 | Stice et al. | |
| 6,245,567 B1 | 6/2001 | Wangh | 435/408 |
| 6,252,133 B1 | 6/2001 | Campbell et al. | |
| 6,258,998 B1 | 7/2001 | Damiani et al. | 800/24 |
| 6,271,436 B1 | 8/2001 | Piedrahita et al. | 800/21 |
| 6,300,129 B1 | 10/2001 | Lonberg et al. | 435/326 |
| 6,573,101 B1 * | 6/2003 | Goomer | 435/458 |
| 6,753,457 B2 | 6/2004 | Wangh et al. | |
| 6,808,704 B1 | 10/2004 | Lanza et al. | |
| 2001/0012513 A1 | 8/2001 | Robl et al. | |
| 2001/0039667 A1 | 11/2001 | Stice et al. | 800/15 |
| 2001/0044937 A1 | 11/2001 | Schatten et al. | 800/21 |
| 2001/0053550 A1 | 12/2001 | Stice | 435/455 |
| 2002/0001842 A1 | 1/2002 | Chapman | 435/449 |
| 2002/0010949 A1 | 1/2002 | Stice et al. | 800/24 |
| 2002/0012655 A1 | 1/2002 | Stice et al. | 424/93.2 |
| 2002/0012660 A1 | 1/2002 | Colman et al. | 424/93.21 |
| 2002/0019993 A1 | 2/2002 | Wakayama, Jr. | 800/21 |
| 2002/0035737 A1 | 3/2002 | Stice et al. | |
| 2002/0056149 A1 | 5/2002 | Campbell et al. | 800/14 |
| 2002/0069423 A1 | 6/2002 | Good et al. | |
| 2002/0073439 A1 | 6/2002 | Stice et al. | |
| 2002/0094968 A1 | 7/2002 | Wolffe et al. | 514/44 |
| 2002/0112254 A1 | 8/2002 | Campbell et al. | 800/14 |
| 2002/0124277 A1 | 9/2002 | Campbell et al. | 800/14 |
| 2002/0129394 A1 | 9/2002 | Aso et al. | 800/15 |
| 2002/0142397 A1 * | 10/2002 | Collas et al. | 435/69.5 |
| 2002/0174449 A1 | 11/2002 | West et al. | |
| 2002/0194637 A1 | 12/2002 | Robl et al. | |
| 2003/0037347 A1 | 2/2003 | Robl et al. | 800/6 |
| 2003/0037352 A1 | 2/2003 | Campbell et al. | 800/14 |
| 2003/0046722 A1 | 3/2003 | Collas et al. | 800/21 |
| 2003/0129745 A1 | 7/2003 | Robl et al. | |
| 2003/0217374 A1 | 11/2003 | West et al. | |
| 2003/0229908 A1 | 12/2003 | Cibelli et al. | |
| 2004/0014206 A1 | 1/2004 | Robl et al. | |
| 2004/0068760 A1 | 4/2004 | Robl et al. | 800/6 |
| 2004/0072288 A1 | 4/2004 | Collas et al. | 435/69.1 |
| 2004/0120934 A1 | 6/2004 | Stice et al. | |
| 2004/0139489 A1 | 7/2004 | Lanza et al. | |
| 2004/0146865 A1 | 7/2004 | Robl et al. | |
| 2004/0162917 A1 | 8/2004 | Akiyama et al. | |
| 2004/0180041 A1 | 9/2004 | Stice et al. | |
| 2004/0194159 A1 | 9/2004 | Stice et al. | |
| 2004/0199935 A1 | 10/2004 | Chapman et al. | |
| 2005/0014258 A1 | 1/2005 | Collas et al. | |
| 2005/0077439 A1 | 4/2005 | Stice et al. | |
| 2005/0095704 A1 | 5/2005 | Robl et al. | |
| 2005/0097627 A1 | 5/2005 | Robl et al. | |
| 2005/0108785 A1 | 5/2005 | Stice et al. | |
| 2005/0153443 A1 | 7/2005 | Lanza et al. | |
| 2005/0183145 A1 | 8/2005 | Goldsby et al. | |
| 2005/0216963 A1 | 9/2005 | Good et al. | |
| 2005/0250203 A1 | 11/2005 | Robl et al. | |
| 2005/0265976 A1 | 12/2005 | Cibelli et al. | |
| 2005/0273870 A1 | 12/2005 | Robl et al. | |
| 2006/0021070 A1 | 1/2006 | Stice et al. | |
| 2006/0051332 A1 | 3/2006 | Lanza et al. | |
| 2006/0083722 A1 | 4/2006 | Cibelli et al. | |

FOREIGN PATENT DOCUMENTS

| | | |
|---|---|---|
| EP | 1106061 | 6/2001 |
| WO | WO 90/06359 | 6/1990 |
| WO | WO 91/08216 | 6/1991 |
| WO | WO 92/03917 | 3/1992 |
| WO | WO 93/04169 | 3/1993 |
| WO | WO 93/12227 | 6/1993 |
| WO | WO 93/25567 | 12/1993 |
| WO | WO 94/21799 | 9/1994 |
| WO | WO 94/25585 | 11/1994 |
| WO | WO 95/20661 | 8/1995 |
| WO | WO 95/28412 | 10/1995 |
| WO | WO 95/33828 | 12/1995 |
| WO | WO 97/07668 | 3/1997 |
| WO | WO 97/07669 | 3/1997 |
| WO | WO 97/12035 | 4/1997 |
| WO | WO 98/14593 | 4/1998 |
| WO | WO 98/30683 | 7/1998 |
| WO | WO 98/33387 | 8/1998 |
| WO | WO 98/37183 | 8/1998 |
| WO | WO 98/39416 | 9/1998 |
| WO | WO 99/21415 | 5/1999 |
| WO | WO 99/34669 | 7/1999 |
| WO | WO 99/45962 | 9/1999 |
| WO | WO 99/60108 | 11/1999 |
| WO | WO 00/25578 | 5/2000 |
| WO | WO 00/42174 | 7/2000 |
| WO | WO 00/51424 | 9/2000 |
| WO | WO 00/67568 | 11/2000 |
| WO | WO 00/67569 | 11/2000 |
| WO | WO 00/74477 | 12/2000 |
| WO | WO 01/00809 | 1/2001 |
| WO | WO 01/23541 | 4/2001 |
| WO | WO 01/30992 | 5/2001 |
| WO | WO 01/35735 | 5/2001 |
| WO | WO 02/14469 | 2/2002 |
| WO | WO 02/24872 A2 | 3/2002 |
| WO | WO 02/051997 | 7/2002 |
| WO | WO 02/057415 | 7/2002 |
| WO | WO 02/067665 | 9/2002 |
| WO | WO 03/064618 | 8/2003 |
| WO | WO 2004/094611 A2 | 11/2004 |

| WO | WO 2005/049788 | 6/2005 |

OTHER PUBLICATIONS

Wade et al. (2002) Eur. J. Biochem., vol. 269, 2284-2287.*
Gurdon et al. (2003) PNAS, Aug. 14 early edition, e-publication, pp. 1-4.*
Amano et al., "Full-Term Development of Enucleated Mouse Oocytes Fused with Embryonic Stem Cells from Different Cell Lines," *Reproduction* 121:729-733 (2001).
Annas et al., "Stem Cell Politics, Ethics and Medical Progress," *Nat. Med.* 5:1339-1341 (1999).
Bell et al., "The Analysis of Costimulatory Receptor Signaling Cascades in Normal T Lymphocytes Using In Vitro Gene Transfer and Reporter Gene Analysis," *Nat. Med.* 7:1155-1158 (2001).
Blau et al., "Plasticity of Cell Fate: Insights from Heterokaryons," *Seminars in Cell & Dev. Biol.* 10:267-272 (1999).
Burke et al., "A Cell Free System to Study Reassembly of the Nuclear Envelope at the End of Mitosis," *Cell* 44:639-652 (1986).
Campbell et al., "Totipotency or Multipotentiality of Cultured Cells: Applications and Progress," *Theriogenology* 47:63-72 (1997).
Cheong et al., "Relationship Between Nuclear Remodeling and Subsequent Development of Mouse Embryonic Nuclei Transferred to Enucleated Oocytes," *Molecular Reproduction and Development* 37:138-145 (1994).
Church, "Are Problems Posed by Genetically Engineered Animals?," *Applied Animal Behavior Science* 20:73-82 (1988).
Cibelli et al., "Bovine Chimeric Offspring Produced by Transgenic Embryonic Stem Cells Generated from Somatic Cell Nuclear Transfer Embryos," *Theriogenology* p. 236.
Cibelli et al., "Transgenic Bovine Chimeric Offspring Produced from Somatic Cell-Derived Stem-Like Cells," *Nat. Biotechnol.* 16:642-646 (1998).
Collas et al., "Lipophilic Organizing Structures of Sperm Nuclei Target Membrane Vesicle Binding and Are Incorporated into the Nuclear Envelope," *Dev. Biol.* 169:123-135 (1995).
Collas, "Sequential PKC- and Cdc2-Mediated Phosphorylation Events Elicit Zebrafish Nuclear Envelope Disassembly," *J. Cell Sci.* 112:977-987 (1999).
Collas et al., "Sorting Nuclear Membrane Proteins at Mitosis," *Trends in Cell Biol.* 10:5-8 (2000).
Collas et al., "The A-Kinase Anchoring Protein, AKAP95, Is A Multivalent Protein with a Key Role in Chromatin Condensation at Mitosis," *J. Cell Biol.* 147:1167-1179 (1999).
Collas et al., "Relationship Between Nuclear Remodeling and Development in Nuclear Transplant Rabbit Embryos," *Biol. Reprod.* 45:455-465 (1991).
Condorelli et al., "Cardiomyocytes Induce Endothelial Cells to Transdifferentiate into Cardiac Muscle: Implications for Myocardium Regeneration," *Proc. Natl. Acad. Sci. U.S.A.* 98:10733-10738 (2001).
Costa et al., "Comparative Analysis of Three Genetic Modifications Designed to Inhibit Human Serum-mediated Cytolysis," *Xenotransplantation* 6:6-16 (1999).
Cubizolles et al., "pEg7, A New *Xenopus* Protein Required for Mitotic Chromosome Condensation in Egg Extracts," *J. Cell Biol.* 143:1437-1446 (1998).
de Anta et al., "k-FGF Protoncogene Expression Is Associated with Murine Testicular Teratogenesis, But Is Not Involved During Mouse Testicular Development," *Histol. Histopathol.*, 11:33-41 (1996).
DiBerardino et al., "Feeding Tadpoles Cloned from *Rana* Erythrocyte Nuclei," *Proc. Natl. Acad. Sci. U.S.A.*, 83:8231-8234 (1986).
Eggan et al., "Hybrid Vigor, Fetal Overgrowth, and Viability of Mice Derived by Nuclear Cloning and Tetraploid Embryo Complementation," *Proc. Natl. Acad Sci U.S.A.* 98:6209-6214 (2001).
Evans et al, "Mitochondrial DNA Genotypes in Nuclear Transfer-Derived Cloned Sheep," *Nat. Genet.* 23:90-93 (1999).
Finlay et al., "Inhibition of In Vitro Nuclear Transport by a Lectin that Binds to Nuclear Pores," *J. Cell Biol.* 104:189-200 (1987).
Finlay et al., "Reconstitution of Biochemically Altered Nuclear Pores: Transport can be Eliminated and Restored," *Cell* 60:17-29 (1990).

Fuchs et al., "Stem Cells: a New Lease on Life," *Cell* 100:143-155 (2000).
Funderburgh et al., "Proteoglycan Expression During Transforming Growth Factor β-Induced Keratocyte-Myofibroblast Transdifferentiation," *J. Biol. Chem.* 276:44173-44178 (2001).
Gjertsen et al., "Cytotoxic $CD4^+$ And $CD8^+$ T Lymphocytes, Generated By Mutant p21-*ras* (12Val) Peptide Vaccination of a Patient, Recognize 12Val-Dependent Nested Epitopes Present Within the Vaccine Peptide and Kill Autologous Tumour Cells Carrying this Mutation," *Int. J. Cancer* 72:784-790 (1997).
Görlich et al., "Identification of Different Roles for RanGDP and RanGTP in Nuclear Protein Import," *EMBO J.* 15:5584-5594 (1996).
Görlich et al., "A Novel Class of RanGTP Binding Proteins," *J. Cell Biol.* 138:65-80 (1997).
Greiner et al., "SCID Mouse Models of Human Stem Cell Engraftment," *Stem Cells* 16:166-177 (1998).
Gurdon et al., "Nuclear Reprogramming and Stem Cell Creation," *Proc. Natl. Acad. Sci. U.S.A.* 100 Suppl. 1:11819-11822 (2003).
Gurdon et al., "Reprogramming of Transplanted Nuclei in Amphibia," *Int. Rev. Cytol. Suppl.* 9:161-178 (1979).
Håkelien et al., "Reprogramming Fibroblasts to Express T-Cell Functions Using Cell Extracts," *Nat. Biotechnol.* 20:460-466 (2002).
Hasler, "Current Status and Potential of Embryo Transfer Reproductive Technology in Dairy Cattle," *J. Dairy Sci.* 75:2857-2879 (1992).
Hu et al., "Transdifferentiation of Myoblasts by the Adipogenic Transcription Factors PPAR γ and C/EBP α," *Proc. Natl. Acad. Sci. U.S.A.* 92:9856-9860 (1995).
Ishida et al., "Production of a Diverse Repertoire of Human Antibodies in Genetically Engineered Mice," *Microbiol. Immunol.* 42(3):143-150, (1998).
Iwasaki et al., "Production of Live Calves Derived from Embryonic Stem-like Cells Aggregated with Tetraploid Embryos," *Biol. Reprod.* 62:470-475 (2000).
Iwasaki et al., "In-vitro Development of Aggregates of Bovine Inner Cell Mass Cells or Bovine Mammary Cells and Putative Tetraploid Embryos Produced by Electrofusion," *Journal of Reproduction and Development* 45:65-71 (1999).
Kasinathan et al., "Production of Calves From G1 Fibroblasts," *Nature Biotech.* 19:1176-1178 (2001).
Kasinathan et al., "Effect of Fibroblast Donor Cell Age and Cell Cycle on Development of Bovine Nuclear Transfer Embryos In Vitro," *Biol. Reprod.* 64:1487-1493 (2001).
Kass et al., "How does DNA Methylation Repress Transcription?," *Trends Genet.* 13:444-449 (1997).
Kato et al., "Germ Cell Nuclei of Male Fetal Mice Can Support Development of Chimeras to Midgestation Following Serial Transplantation," *Development* 121:779-783 (1995).
Kikyo et al., "Reprogramming Nuclei: Insights from Cloning, Nuclear Transfer and Heterokaryons," *J. Cell Sci.* 113:11-20 (2000).
Kikyo et al., "Active Remodeling of Somatic Nuclei in Egg Cytoplasm by the Nucleosomal ATPase ISWI," *Science* 289:2360-2362, 2000.
Kono et al., "Development of Chimaeric Two-Cell Mouse Embryos Produced by Allogenic Exchange of Single Nucleus From Two-and Eight-Cell Embryos," *Gamete. Res.* 24:375-384 (1989).
Kuroiwa et al., "Manipulation of Human Minichromosomes to Carry Greater than Megabase-Sized Chromosome Inserts," *Nature Biotechnol.* 18:1086-1090, (2000).
Kutay et al., "Dominant-Negative Mutants of Importin-β Block Multiple Pathways of Import and Export through the Nuclear Pore Complex," *EMBO J.* 16:1153-1163 (1997).
Landsverk et al., "Reprogrammed Gene Expression In A Somatic Cell-Free Extract," *EMBO Rep.* 3:384-389 (2002).
Li et al., "Activation of Mitogen-Activated Protein Kinases (Erk 1 and Erk2) Cascade Results in Phosphorylation of NF-M Tail Domains in Transfected NIH 3T3 Cells," *Eur. J. Biochem.* 262:211-217 (1999).
Lohka et al., "Formation In Vitro of Sperm Pronuclei and Mitotic Chromosomes Induced by Amphibian Ooplasmic Components," *Science* 220:719-721 (1983).
Lohka et al., "Induction of Nuclear Envelope Breakdown, Chromosome Condensation and Spindle Formation in Cell-Free Extracts," *J. Cell Biol.* 101:518-523 (1985).

Macaulay et al., "Assembly of the Nuclear Pore: Biochemically Distinct Steps Revealed with NEM, GTPγS, and BAPTA," *J. Cell Biol.* 132:5-20 (1996).

Maghazachi et al., "Interferon-Inducible Protein-10 and Lymphotactin Induce the Chemotaxis and Mobilization of Intracellular Calcium in Natural Killer Cells through Pertussis Toxin-Sensitive and -Insensitive Heterotrimeric G-Proteins," *FASEB J.* 11:765-774 (1997).

Mann, "Inviability of Parthenogenones is Determined by Pronuclei, Not Egg Cytoplasm," *Nature* 310:66-67 (1984).

Maus et al., "Disassembly of the Drosophila Nuclear Lamina in a Homologous Cell-Free System," *J. Cell Sci.* 108:2027-2035 (1995).

Meinecke-Tillmann, "Über Kerntransplantationen und das Klonen von Säugetieren," *Praktishe Tierarzt* 9:59-67 (1988).

Miake-Lye et al., "Induction of Early Mitotic Events in a Cell-Free System," *Cell* 41:165-175 (1985).

Modlinski et al., "Further Perspectives in Mammalian Embryo Cloning: Establishment, Culture and Possible Use of Embryonic Stem Cells," *Animal Science Papers and Reports—Polish Academy of Sciences* 13:169-184 (1995).

Moreira et al., "Architectural Defects in Pronuclei of Mouse Nuclear Transplant Embryos," *J. Cell Sci.* 116:3713-3720, (2003).

Morrison, "Stem Cell Potential: Can Anything Make Anything," *Curr. Biol.* 11:R7-R9 (2001).

Munsie et al., "Isolation of Pluripotent Embryonic Stem Cells from Reprogrammed Adult Mouse Somatic Cell Nuclei," *Curr. Biol.* 10:989-992 (2000).

Munsie et al., "Novel Method for Demonstrating Nuclear Contribution in Mouse Nuclear Transfer," *Reprod. Fertil. & Dev.*. 10:633-637 (1998).

Newmeyer et al., "In Vitro Transport of a Fluorescent Nuclear Protein and Exclusion of Non-Nuclear Proteins," *J. Cell Biol.* 103:2091-2102 (1986).

Newmeyer "Nuclear Import Can be Separated into Distinct Steps In Vitro: Nuclear Pore Binding and Translocation," *Cell* 52:641-653 (1988).

Newmeyer et al., "An N-Ethylmaleimide-Sensitive Cytosolic Factor Necessary for Nuclear Protein Import: Requirement in Signal-Mediated Binding to the Nuclear Pore," *J. Cell Biol.* 110:547-557 (1990).

Newport, "Nuclear Reconstitution In Vitro: Stages of Assembly Around Protein-Free DNA," *Cell* 48:205-217 (1987).

Niemann et al., "Manipulating Early Pig Embryos," *J. Reprod.& Fertil. Suppl.* 48:75-94 (1993).

Notarianni, "Prospects for the Attainment of Transgenesis in Livestock," Abstract No. 4173, *Genetic Engineering Applications*, p. 613.

Overström, "Manipulation of Early Embryonic Development," *Animal Reproduction Science* 28:277-285 (1992).

Paschal et al,. "Identification of NTF2, a Cytosolic Factor for Nuclear Import that Interacts with Nuclear Pore Complex Protein p62," *J. Cell Biol.* 129:925-937 (1995).

Perry et al., "Mammalian Oocyte Activation by the Synergistic Action of Discrete Sperm Head Components: Induction of Calcium Transients and Involvement of Proteolysis," *Dev. Biol.* 217:386-393 (2000).

Perry et al., "Mammalian Transgenesis by Intracytoplasmic Sperm Injection," *Science* 284:1180-1183 (1999).

Polejaeva et al., "New Advances in Somatic Cell Nuclear Transfer: Application in Transgenesis," *Theriogenology* 53:117-126 (2000).

Polejaeva et al., "Cloned Pigs Produced by Nuclear Transfer From Adult Somatic Cells," *Nature* 407:86-90 (2000).

Polge, "Potential Impact of Advanced Biotechnology on Genetic Conservation Programmes," in *Genetic Conservation of Domestic Livestock*, edited by Alderson, Wallingford, U.K. pp. 227-235 (1990).

Pollock et al., "Development of Human Lymphocyte-Engrafted SCID Mice as a Model for Immunotoxicity Assessment," *Fund. & Appl. Toxicol.* 22:130-138, (1994).

Prelle et al., "Establishment of Pluripotent Cell Lines from Vertebrate Species—Present Status and Future Prospects," *Cells Tissues Organs* 165:220-236 (1999).

Ramirez et al., "Life-Supporting Human Complement Regulator Decay Accelerating Factor Transgenic Pig Liver Xenograft Maintains the Metabolic Function and Coagulation in the Nonhuman Primate for Up to 8 Days," *Transplantation* 70:989-998 (2000).

Rexroad, "History of Genetic Engineering of Laboratory and Farm Animals," *Genetic Engineering of Animals, An Agricultural Perspective*, pp. 127-138 (1986).

Ribbeck et al., "NTF2 Mediates Nuclear Import of Ran," *EMBO J.* 17:6587-6598 (1998).

Rideout et al., "Generation of Mice From Wild-Type and Targeted ES Cells by Nuclear Cloning," *Nat. Genet.* 24:109-110 (2000).

Rideout et al., "Nuclear Cloning and Epigenetic Reprogramming of the Genome," *Science* 293:1093-1098 (2001).

Risau et al., "Vasculogenesis and Angiogenesis in Embryonic-Stem-Cell-Derived Embryoid Bodies," *Development* 102:471-478 (1988).

Sandrin et al., "Galα(1,3)Gal, the Major Xenoantigen(s) Recognised in Pigs by Human Natural Antibodies," *Immunol. Rev.* 141:169-190 (1994).

Schlenstedt et al., "Reconstitution of Nuclear Protein Transport with Semi-Intact Yeast Cells," *J. Cell Biol.* 123:785-798 (1993).

Schnieke et al., "Human Factor IX Transgenic Sheep Produced by Transfer of Nuclei from Transfected Fetal Fibroblasts," *Science* 278:2130-2133 (1997).

Seidel, "Reproductive Biotechnology and 'Big' Biological Questions," *Theriogenology* 53:187-194 (2000).

Shelton, "Embryo Manipulation in Research and Animal Production," *Aust. J. Biol. Sci.* 41:117-132 (1988).

Shen et al., "Molecular Basis of Transdifferentiation of Pancreas to Liver," *Nat. Cell Biol.* 2:879-887 (2000).

Sotomaru et al., "Induction of Pluripotency by Injection of Mouse Trophectoderm Cell Nuclei into Blastocysts Following Transplantation into Enucleated Oocytes," *Theriogenology* 52:213-220 (1999).

Sotomaru et al., "Nuclear Transplantation of Mouse Inner Cell Mass and Trophectoderm Cells into Endonucleated Two-cell Embryos," *Journal of Reproduction and Development* 44:1-6 (1998).

Steen et al., "Recruitment of Protein Phosphatase 1 to the Nuclear Envelope by A-Kinase Anchoring Protein AKAP149 is a Prerequisite for Nuclear Lamina Assembly," *J. Cell Biol.*150:1251-1261 (2000).

Steen et al., "A Kinase-Anchoring Protein (AKAP)95 Recruits Human Chromosome-Associated Protein (hCAP)-D2/Eg7 for Chromosome Condensation in Mitotic Extract," *J. Cell Biol.* 149:531-536 (2000).

Stice et al., "Nuclear Reprogramming in Nuclear Transplant Rabbit Embryos," *Biol. Reprod.* 39:657-664 (1988).

Stice et al., "Bovine Pluripotent Embryonic Cells Contribute to Nuclear Transfer and Chimeric Fetuses," *Theriogenology* 41:301 (1994).

Stice et al., "Pluripotent Bovine Embryonic Cell Lines Direct Embryonic Development Following Nuclear Transfer," *Biol. Reprod.* 54:100-110 (1996).

Sullivan et al., "Cloned Calves From Chromatin Remodeled in Vitro," *Biology of Reproduction* 70:146-153, (2004).

Sun et al., "Immunization with Interleukin-2-Secreting Allogeneic Cells Transfected with DNA from Mouse Melanoma Cells Induces Immune Responses that Prolong the Lives of Mice with Melanoma," *Cancer Gene Therapy* 5:110-118 (1998).

Suprynowicz et al., "A Fractionated Cell-Free System for Analysis of Prophase Nuclear Disassembly," *J. Cell Biol.* 103:2073-2081 (1986).

Tada et al., "Embryonic Germ Cells Induce Epigenetic Reprogramming of Somatic Nucleus in Hybrid Cells," *EMBO J.* 16:6510-6520 (1997).

Tamashiro et al., "Postnatal Growth and Behavioral Development of Mice Cloned from Adult Cumulus Cells," *Biol. Reprod.* 63:328-334 (2000).

Tearle et al., "The α-1,3-Galactosyltransferase Knockout Mouse: Implications for Xenotransplantation," *Transplantation* 61:13-19 (1996).

Wade et al., "Chromatin Remodeling in Nuclear Cloning," *Eur. J. Biochem.* 269:2284-2287 (2002).

Wakayama et al., "Mice Cloned from Embryonic Stem Cells," *Proc. Natl. Acad. U.S.A.* 96:14984-14989 (1999).

Wakayama et al., "Cloning of Male Mice From Adult Tail-Tip Cells," *Nat. Genet.* 22:127-128 (1999).

Wakayama et al., "Nuclear Transfer into Mouse Zygotes," *Nat. Genet.* 24:108-109 (2000).

Wakayama et al., "Differentiation of Embryonic Stem Cell Lines Generated from Adult Somatic Cells by Nuclear Transfer," *Science* 292:740-743 (2001).

Wakayama et al., "The First Polar Body can be Used for the Production of Normal Offspring in Mice," *Biol. Reprod.* 59:100-104 (1998).

Wakayama et al., "Full-Term Development of Mice from Enucleated Oocytes Injected with Cumulus Cell Nuclei," *Nature* 394:369-74 (1998).

Wakayama et al., "Fertilisability and Developmental Ability of Mouse Oocytes with Reduced Amounts of Cytoplasm," *Zygote* 6:341-346 (1998).

Wakayama et al., "Cloning the Laboratory Mouse," *Semin. Cell & Dev. Biol.* 10:253-258, (1999).

Wangh et al., "Efficient Reactivation of *Xenopus* Erythrocyte Nuclei in *Xenopus* Egg Extracts," *J. Cell Sci.* 108:2187-2196 (1995).

Westphal et al., "Transposon-generated 'Knock-out' and 'Knock-in' Gene-Targeting Constructs For Use in Mice," *Current Biology* 7:R530-R533 (1997).

Wilson et al., "A Trypsin-Sensitive Receptor on Membrane Vesicles is Required for Nuclear Envelope Formation In Vitro," *J. Cell Biol.* 107:57-68 (1988).

Yang et al., "Micromanipulation of Mammalian Embryos: Principles, Progress and Future Possibilities," *Theriogenology* 38:315-335 (1992).

Zhou et al., "Developmental Potential of Mouse Embryos Reconstructed from Metaphase Embryonic Stem Cell Nuclei," *Biol. Reprod.* 65:412-419 (2001).

U.S. Appl. No. 10/705,519, filed Nov. 10, 2003.

U.S. Appl. No. 11/011,711, filed Dec. 14, 2004.

Collas et al., "Electrical Activation of Mouse Oocytes," *Theriogenology* 32(5):835-844 (1989).

Collas et al., "Electrically Induced Calcium Elevation, Activation, and Parthenogenetic Development of Bovine Oocytes," *Mol. Reprod. Dev.* 34:212-223 (1993).

Collas, "Nuclear Envelope Disassembly in Mitotic Extract Requires Functional Nuclear Pores and a Nuclear Lamina," *J. Cell Sci.* 111:1293-1303 (1998).

Collas, "Modulation of Plasmid DNA Methylation and Expression in Zebrafish Embryos," *Nuc. Acid. Res.* 26:4454-4461 (1998).

Collas and Robl, "Reprogrammed Gene Expression in a Somatic Cell-Free Extract," *Transgenic Research* 11(1):75 (Abstract) (2002).

Commonwealth of Massachusetts Superior Court Civil Action No. 04-0445 BLS2 (2004).

Coppock et al., "Replication of *Xenopus* Erythrocyte Nuclei in a Homologous Egg Extract Requires Prior Proteolytic Treatment," *Dev. Biol.* 131:102-110 (1989).

Dimitrov and Wolffe, "Remodeling Somatic Nuclei in *Xenopus laevis* egg extracts: Molecular Mechanisms for the Selective Release of Histones H1 and H1o from Chromatin and the Acquisition of Transcriptional Competence," *EMBO J.* 15:5897-5906 (1996).

Fissore and Robl, "Intracellular $Ca^{2+}$ Response of Rabbit Oocytes to Electrical Stimulation." *Mol. Reprod. Dev.* 32:9-16 (1992).

Håkelien et al., "Reprogramming Fibroblasts to Express T-cell Functions Using Cell Extracts," *Nat. Biotechnol.* 20(5):460-466 (2002).

Huang et al., "The Enhancement of Specific Gene Transcription in Isolated Nuclei by Added HeLa Whole Cell Extract," *Int. J. Biochem.* 16:963-969 (1984).

Kikyo et al., "Active Remondeling of Somatic Nuclei in Egg Cytoplasm by the Nucleosomal ATPase ISWI," *Science* 289:2360-2362 (2000).

Landsverk et al., "Reprogrammed Gene Expression in a Somatic Cell-free Abstract," *EMBO Rep.* 3(4):384-389 (2002).

Leno and Munshi, "Initiation of DNA Replication in Nuclei from Quiescent Cells Requires Permeabilization of the Nuclear Membrane," *J. Cell. Biol.* 127:5-14 (1994).

Martins et al., "HA95 is a Protein of the Chromatin and Nuclear Matrix Regulating Nuclear Envelope Dynamics," *J. Cell Sci.* 113:3703-3713 (2000).

Renard et al., "Nuclear Transfer Technologies: Between Successes and Doubts," *Theriogenology* 57(1):203-222 (2002).

Shi et al., "Synergistic Effect of A23187 and Cycloheximide Allows Effective Activation of Freshly Matured Bovine Oocytes," *Theriogenology* 39:309 (1993).

United State District Court, District of Massachusetts, Civil Action No. 04-11013-RGS (2004).

University of Massachusetts, Uniform Invention Disclosure Form dated Jul. 7, 2000.

University of Massachusetts, Uniform Invention Disclosure Form dated Nov. 23, 1998.

Weiss et al., "DNA Demethylation In Vitro: Involvement of RNA," *Cell* 86:709-718 (1996).

Wright and Bondioli, "Aspects of In Vitro Fertilization and Embryo Culture in Domestic Animals," *J. Anim. Sci.* 53:702-729 (1981).

Yang and Anderson, "Micromanipulation of Mammalian Embryos: Principles, Progress and Future Possibilities", *Theriogenology* 38:315-335, 1992.

* cited by examiner

Alkaline Phosphatase Assay

Figure 20: List of Exemplary Autoantibodies

1. Anti-lopicortin autoantibodies associated with rheumatic diseases (Goulding NJ et al. Ann Rheum Dis 1989;48:843-850; Podgorski MR et al. Br J Rheumatol 1988;28 (Suppl. 1):30.; Loftus JK et al. Br J Rheumatol 1989;28 (Suppl. 2):35-36

2. Autoantibodies to brain myelin basic protein (MBP) associated with measles in children 3. Autoantibodies to thyroglobulin, T4 or T3 associated with autoimmune thyroiditis (Thyroid Database: http://www.offa.org/ofathy.html)

4. Autoantibodies to desmoglein 1, associated with superficial subtypes of pemphigus (Marinkovich, MP., 2001: Blistering Diseases; http://telemedicine.org/blister.htm)

5. Autoantibodies to desmoglein 3, associated with Pemphigus vulgaris (Marinkovich, MP., 2001: Blistering Diseases; http://telemedicine.org/blister.htm)

6. Autoantibodies associated with neuromuscular disorders (see Table and details below):
Neuromuscular Clinical Laboratory, University of Washington, St. Louis, MO (www.neuro.wustl.edu/neuromuscular/over/labdis.html) and references therein 7. Autoantibodies, such as IgM antibodies, reactive with
   GalC,
   GalNAc-GD1a
   GALOP antigen
   GD1a
   GD1b
   GM1 ganglioside
   Co-GM1; GM1; NP-9
   GM2
   Heparan sulfate
   MAG
   Neurofilaments
   SGPG
   Sulfatide
   Tubulin, or
   Decorin (BJ antigen)

8. Autoantibodies, such as IgG antibodies, reactive with
   Acetylcholine receptors,

Figure 20 (cont'd)

Muscle
Other
Channels
Calcium
Potassium
Gangliosides
GM1
GD1b
GQ1b
GD1a
GalNAc-GD1a
Hu
Muscle striations
MuSK, or
Yo 9. Autoantibodies, such as polyspecific IgM or IgG, reactive with
connective tissue,
proteins associated with Diabetes,
M-proteins
Muscle
Nerve
Oligosaccharide antigens
Paraneoplastic
Stiffman, or
Vasculitis 10. Antibodies reactive with glycolipids or Glycoproteins

- Anti-GM1 antibodies associated with motor syndromes
  - IgM:
    - Motor: Asymmetric, Distal, Chronic
    - Demyelinating or Axonal
  - IgG:
    - Signs: Motor predominant; Occasional sensory loss
    - Syndromes
      - Chronic: Asymmetic, Distal, without conduction block.

- Anti-MAG antibodies associated with polyneuropathy

Figure 20 (Cont'd)

- Anti-sulfamide antibodies associated with polyneuropathy: M-protein (IgM): GALOP syndrome; Weakness; Demyelinating ; polyclonal (IgM or IgG): Dysesthesias; Axonal

- Anti-GQ1b antibodies (IgG)
  - Miller Fisher Syndrome
- Antibodies vs. GALOP (Central Myelin Lipid) Antigen (CMA)
  - GALOP Syndrome (Gait disorder; Autoantibody; Late-age-Onset; Polyneuropathy)
- Anti-GD1b antibodies
  - IgM: Ataxic sensory neuropathy
  - IgG: Acute sensory ± motor neuropathy
- Anti-GD1a antibodies
  - IgM: Demyelinating motor neuropathies (in the setting of an IgM M-protein) & lower motor neuron syndromes.
    - Most serums with this IgM reactivity also show binding to GM1 ganglioside
  - IgG: Motor, & axonal Guillain-Barré-like syndromes (AMAN) & motor neuropathies.
- Anti-GalNAc-GD1a antibodies
  - *Campylobacter jejuni* infection
  - Acute motor neuropathies
  - Distal predominant weakness & Sparing of the cranial nerves 11. Antibodies reactive with intracellular antigens

- Anti-Hu (ANNA-1) antibodies (IgG in serum & CSF)
  - Associated with Small Cell Neoplasms, especially lung
- Anti-Yo antibodies (IgG in serum & CSF)
  - Associated with gynecologic neoplasms.
- Anti-Tubulin antibodies (IgM > IgG)
  - CIDP (asymmetric)
- IgM vs Neurofilaments
  - Polyclonal: Opsoclonus-Myoclonus syndromes
  - Monoclonal: Axonal sensory neuropathy
- Stiffman syndromes
  - Glutamic acid decarboxylase □(50% to 80%): Also found in
    - Palatal myoclonus & epilepsy
    - Insulin-dependent diabetes mellitus (IDDM)
      - Association with antibodies to tyrosine phosphatase IA-2
  - Autoimmune polyendocrine syndrome II
  - Pancreatic islet cell (60%)

Figure 20 (Cont'd)

- o Also found in type 1 diabetes: Lower titer, different staining pattern
- o Amphiphysin (128kDa) ✻: with breast cancer
- o 80 kDa protein
- Vasculitis: Anti-neutrophil cytoplasmic antibodies (ANCA)
  - o c-ANCA
  - o p-ANCA 12. Antibodies reactive with receptors or channels

- IgG vs P/Q-type Voltage Gated Calcium Channel (Conotoxin w-MVIIC binding; CACNB2)
  - o Myasthenic syndrome (Lambert-Eaton)
- AChR, subunit a3
  - o Autonomic neuropathy
  - o Small cell lung cancer
  - o Ion Channels 13. Autoantibodies associated with vasculitis

- ANCA: General
  - o Rare in polyarteritis with no inflammation in vessels smaller than arteries
  - o Initial testing by immunocytochemistry
  - o Confirmation by Western blot: Binding to specific antigen
- c-ANCA
  - o Antigen: Proteinase-3
  - o Disease specificity: Wegener's
  - o Pathology: granulomatous inflammation
  - o Pathogenicity
    - Leukocyte activation: Potentiated by TNF-a
    - Increased ICAM-1 expression on endothelial cells ® Leukocyte adhesion
- p-ANCA
  - o Antigen
    - Myeloperoxidase: Vasculitis
    - Other: Vasculitis; Inflammatory bowel; Hepatitis; Rheumatologic disorders
  - o Pathology: Often Hemorrhagic capillaritis Figure 21 Exemplary Antigenic Determinants of Pathogens Adeno-associated Virus VP1, VP2 or VP3 peptides
Lethal factor of Bacillus antracis
Chlamydia lipopolysaccharid antigen (LGV type II strain 434 antigen) olyclonal 7/98)
Clostridium Botulinum D Toxoid
Clusterin
Diptheria Toxin
Epstein Barr Virus capsid antigen gp120
Hepatitis B Core Antigen
Hepatitis B virus surface antigen
HCV Core, HCVNS3, HCV NS4, HCVNS5 peptides of Hepatitis C virus
HGV protein of Hepatitis G Virus
glycoprotein D of Herpes Simplex Virus Type
hemagglutin of Influenza virus type A
nucleoproteid of Influenza Virus Type A
legionella pneumophilia SG1 antigen
desmoglein 3 protein of Pemphigus vulgaris
Pichia pastoris
Lipopolisaccharides of Pseudomonas mallei
P42 inner-capsid antigen of Rotavirus group of viruses
Rubella virus structural glycoprotein E1
Lipopolisaccharides of Salmonella typhimurium
enterotoxin A from FRI-722H strain of St. aureus

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: primer

<400> SEQUENCE: 1
gctattcaca tgttcagtgt ag                                                  22

<210> SEQ ID NO 2
<211> LENGTH: 22
<212> TYPE: DNA
<213> ORGANISM: Artificial Sequence
<220> FEATURE:
<223> OTHER INFORMATION: primer

<400> SEQUENCE: 2
gacaggagtt gcatcctgta ca                                                  22

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
atgtacagga tgcaactcct gtctt                                               25

<210> SEQ ID NO 4
<211> LENGTH: 25
<212> TYPE: DNA
<213> ORGANISM: Artificial Sequence
<220> FEATURE:
<223> OTHER INFORMATION: primer

<400> SEQUENCE: 4
gttagtgttg agatgatgct ttgac                                               25

<210> SEQ ID NO 5
<211> LENGTH: 25
<212> TYPE: DNA
<213> ORGANISM: Artificial Sequence
<220> FEATURE:
<223> OTHER INFORMATION: primer

<400> SEQUENCE: 5
atgtacagga tgcaactcct gtctt                                               25

<210> SEQ ID NO 6
<211> LENGTH: 25
<212> TYPE: DNA
<213> ORGANISM: Artificial Sequence
<220> FEATURE:
<223> OTHER INFORMATION: primer

<400> SEQUENCE: 6
gttagtgttg agatgatgct ttgac                                               25
```

US 7,491,534 B2

METHODS FOR ALTERING CELL FATE TO GENERATE T-CELLS SPECIFIC FOR AN ANTIGEN OF INTEREST

CROSS-REFERENCE TO RELATED APPLICATION

This application is a continuation of International Application No. PCT/US03/08120, filed Mar. 14, 2003, which will be published in English under PCT Article 21(2), and which claims the benefit of the filing date of U.S. provisional application 60/376,653, filed Apr. 30, 2002 now abandoned, hereby incorporated by reference. In addition, this application is a continuation-in-part of U.S. utility application 10/015,824. filed Dec. 10, 2001 now anandoned, which claims benefit of the filing date of U.S. provisional application 60/258,152, filed Dec. 22, 2000 now abandoned.

BACKGROUND OF THE INVENTION

In general, the invention features methods for converting cells into a desired cell type (e.g., cells reactive with an antigen of interest) and methods for administering these reprogrammed cells to a mammal for the treatment or prevention of disease.

Despite having essentially the same genome, different classes of somatic cells in a particular mammal have distinctive phenotypes due to the different combinations of genes that they express. These different expression profiles allow cells to perform certain functions, such as secretion of a hormone or cartilage, or the expression of a T-cell receptor and thus antigen recognition leading to replication and clonal expansion.

Because many diseases and injuries are caused by damage to a particular class of cells, methods are needed to produce cells of a desired cell type that may be used to replace these damaged cells. Preferably, these replacement cells have the same genotype as the damaged cells.

Given the high prevalence of cancer and obesity in developed countries, improved methods are also needed to treat or prevent these conditions. For example, many of the current treatments that destroy cancerous cells also affect normal cells, resulting in a variety of possible side-effects, such as nausea, vomiting, low blood cell counts, increased risk of infection, hair loss, and ulcers in mucous membranes. Many current therapies for obesity have limited long-term efficacy and may produce adverse side-effects. Thus, improved therapies are needed for cancer and obesity that have few adverse side-effects and greater efficacy. Improved methods are also desirable for the treatment of other diseases that cause debilitating effects, such as immune dysfunction and autoimmune diseases.

SUMMARY OF THE INVENTION

The purpose of the present invention is to provide methods for altering the characteristics or functions of cells. For example, methods have been developed to produce T-cells that express a functional T-cell receptor (TCR) that specifically binds an antigen of interest. In particular, these methods involve incubating a nucleus or chromatin mass from a donor cell with a reprogramming media (e.g., a cell extract) under conditions that allow nuclear or cytoplasmic components such as transcription factors to be added to, or removed from, the nucleus or chromatin mass. Preferably, the added transcription factors promote the expression of mRNA or protein molecules found in cells of the desired cell type (e.g., T-cells), and the removal of transcription factors that would otherwise promote expression of mRNA or protein molecules found in the donor cell. If desired, the chromatin mass may then be incubated in an interphase reprogramming media (e.g., an interphase cell extract) to reform a nucleus that incorporates desired factors from either reprogramming media. Then, the nucleus or chromatin mass is inserted into a recipient cell or cytoplast, forming a reprogrammed cell of the desired cell type (e.g., a T-cell). In a related method, a permeabilized cell is incubated with a reprogramming media (e.g., a T-cell extract) to allow the addition or removal of factors from the cell, and then the plasma membrane of the permeabilized cell is resealed to enclose the desired factors and restore the membrane integrity of the cell. If desired, the steps of any of these methods may be repeated one or more times or different reprogramming methods may be performed sequentially to increase the extent of reprogramming, resulting in a greater alteration of the mRNA and protein expression profile in the reprogrammed cell. In some embodiments, a nucleic acid that encodes a TCR reactive with an antigen of interest is inserted into the chromatin mass, nucleus, or cell before, during, or after reprogramming. Preferably, a reprogrammed T-cell that binds an antigen of interest is selected or purified. The reprogrammed T-cell can be used to replace non-functional T-cells of patients with highly reactive and antigen-specific T-cells and used to destroy undesired cells, such as tumor cells, fat cells, and autoimmune generated cells (e.g., B-cells that produce a "self"-reacting antibody or T-cells that are activated by presented self epitopes). These cells may also be used to destroy infectious pathogens in a mammal.

Accordingly, in a first aspect, the invention provides a method of reprogramming a cell to express a TCR reactive with an antigen of interest. This method involves incubating a nucleus with a reprogramming media (e.g., a T-cell extract or a media having a T-cell factor such as a molecule present in, or expressed by, T-cells) under conditions that allow the removal of a factor from the nucleus or the addition of a factor to the nucleus. Then the nucleus or a chromatin mass formed from incubation of the nucleus in the reprogramming media is inserted into a recipient cell or cytoplast, thereby forming a reprogrammed cell. In various embodiments, a nucleic acid encoding a TCR reactive with an antigen of interest is inserted into the nucleus, chromatin mass, or reprogrammed cell. In some embodiments, a reprogrammed cell expressing a TCR reactive with the antigen is selected or purified. In one preferred embodiment, the nucleus is incubated with an interphase reprogramming media (e.g., an interphase T-cell extract). Preferably, the nucleus remains membrane-bounded, and the chromosomes in the nucleus do not condense during incubation with this interphase reprogramming media. In another preferred embodiment, a chromatin mass is formed from incubation of the nucleus in a mitotic reprogramming media (e.g., a mitotic media having a T-cell factor or a mitotic T-cell extract). Preferably, this chromatin mass is then incubated in an interphase reprogramming media under conditions that allow a nucleus to reform, and the reformed nucleus is inserted into the recipient cell or cytoplast.

In a related aspect, the invention provides another method of reprogramming a cell to express a TCR reactive with an antigen of interest. This method involves incubating a chromatin mass with a reprogramming media (e.g., a T-cell extract or a media having a T-cell factor) under conditions that allow the removal of a factor from the chromatin mass or the addition of a factor to the chromatin mass. Then the chromatin mass or nucleus formed from incubation of the chromatin mass in a reprogramming media (e.g., an interphase media having a T-cell factor or an interphase T-cell extract) is inserted into a recipient cell or cytoplast, thereby forming a reprogrammed cell. In various embodiments, a nucleic acid encoding a TCR reactive with an antigen of interest is inserted into the nucleus, chromatin mass, or reprogrammed cell. In some embodiments, a reprogrammed cell expressing a TCR reactive with the antigen is selected or purified. In one preferred embodiment, the chromatin mass is generated by incubating a nucleus from a donor cell in a detergent and salt solution, in a protein kinase solution, or in a mitotic reprogramming media in the presence or absence of an antibody to NuMA or to another protein of the nucleus. In another preferred embodiment, the chromatin mass is isolated from mitotic cells.

In another related aspect, the invention provides yet another method of reprogramming a cell to express a TCR reactive with an antigen of interest. This method involves incubating a permeabilized cell with a reprogramming media (e.g., a media having a T-cell factor or a T-cell extract) under conditions that allow the removal of a factor from the nucleus or chromatin mass of the permeabilized cell or the addition of a factor to the nucleus or chromatin mass, thereby forming a reprogrammed cell. In various embodiments, a nucleic acid encoding a TCR reactive with an antigen of interest is inserted into the nucleus, chromatin mass, or reprogrammed cell. In some embodiments, a reprogrammed cell expressing a TCR reactive with the antigen is selected or purified. In one preferred embodiment, the permeabilized cell is incubated with an interphase reprogramming media (e.g., an interphase media having a T-cell factor or an interphase T-cell extract). Preferably, the nucleus in the permeabilized cell remains membrane-bounded, and the chromosomes in the nucleus do not condense during incubation with this interphase reprogramming media. In another preferred embodiment, a chromatin mass is formed from incubation of the permeabilized cell in a mitotic reprogramming media. In yet another preferred embodiment, the reprogrammed cell is incubated under conditions that allow the membrane of the reprogrammed cell to reseal. If desired, the permeabilized cell may be formed by incubating an intact cell with a detergent, such as digitonin, or a bacterial toxin, such as Streptolysin O.

The invention also provides reprogrammed cells generated using any method of the invention or a combination of methods of the invention. These cells are useful for the treatment or prevention of a disease due to a deficiency in a particular cell type. Additionally, reprogrammed cells that express two or more mRNA molecules or proteins that are each specific for a certain cell type may have novel combinations of phenotypes and activities that are useful for the treatment of disease. For example, cells that maintain the ability of the donor cell to divide and gain the ability to form a functional T-cell receptor or a functional neurofilament are useful for the generation of multiple T-cells or neurons for therapeutic applications. Once transplanted into a subject, these cells may maintain the ability to divide, thereby reducing the dose or dosing frequency of the transplant cells that is required to treat, prevent, or stabilize a disease. The characterization of these cells may also result in the identification of proteins involved in the regulation of gene expression.

In one such aspect, the invention features a cell that expresses a combination of two or more endogenous mRNA molecules or endogenous proteins that is not expressed by a naturally-occurring cell. In a related aspect, the invention features a cell that expresses a combination of two or more endogenous mRNA molecules or endogenous proteins at a level that is at least 10, 20, 50, 75, or 100 fold greater than the expression level of the corresponding mRNA molecules or proteins in any naturally-occurring cell. In preferred embodiments of the above aspects, the cell expresses a combination of 5, 10, 25, 50, 75, 100, 150, 300, or more endogenous mRNA molecules or endogenous proteins that is not expressed by a naturally-occurring cell. In another preferred embodiment, the cell expresses 1, 3, 5, 10, 25, 50, 100, or more endogenous mRNA molecules or endogenous proteins that are specific for one cell type (e.g., specific for T-cells) and expresses 1, 3, 5, 10, 25, 50, 100, or more endogenous mRNA molecules or endogenous proteins that are specific for another cell type. In other preferred embodiments, the cell has a combination of 2, 5, 10, 25, 50, 75, 100, 150, 300, or more activities or phenotypes that are not exhibited in a naturally-occurring cell. In yet other preferred embodiments, the cell is able to divide or is immortalized and expresses a neuronal protein such as the NF200 neurofilament protein or any other protein expressed by differentiated neurons. In still other preferred embodiments, the cell is able to divide or is immortalized and expresses IL-2, an IL-2 receptor, a T-cell receptor, CD3, CD4 and CD8, CD45 tyrosine phosphatase, or any other protein expressed in hematopoietic cells. In yet another embodiment, the cell is formed from the reprogramming of a donor fibroblast cell, nucleus, or chromatin mass, and the reprogrammed cell expresses one or more cytoskeleton proteins such as an integrin at a level that is at least 25, 50, 75, 90, or 95% lower that the corresponding level in the donor fibroblast under the same conditions. In another embodiment, a reprogrammed cell formed from a donor fibroblast or liver cell (e.g., a hepatocyte) expresses IL-2, a neurofilament protein, a T-cell receptor, Oct4, or insulin.

In a related aspect, the invention provides a cell that expresses a T-cell specific protein (e.g., T-cell receptor protein, IL-2 receptor, CD3, CD4, or CD8) and one or more fibroblast-specific proteins. Preferably, stimulation of the cell with an antigen or an anti-CD3 antibody induces the expression of the α-chain of the IL-2 receptor. Preferred T-cells express a TCR specific for one of the tumor antigens listed in Table 1, a fat cell antigen, or an antigen from an infectious pathogen (e.g., a protein, nucleic acid, carbohydrate, lipid, or small molecule from a pathogen or an intact pathogen such as a bacteria, virus, or yeast). Other desirable T-cells express a TCR specific for an antibody reactive with a self epitope or an antigen from an autoimmune generated cell (e.g., a B-cell that produces an an antibody reactive with a self epitope, also called an autoantibody). In another aspect, the invention provides a cell that expresses a hematopoietic-specific protein (e.g., CD45 typrosine phosphatase) and one or more fibroblast-specific proteins. In another related aspect, the invention provides a cell that expresses a neuron-specific protein (e.g., a neurofilament protein such as NF200) or forms neurites and expresses one or more fibroblast-specific proteins. In still another aspect, the invention provides a cell that expresses a neurofilament protein (e.g., NF200) or forms neurites and is immortalized. In yet another aspect, the invention provides a cell that expresses a stem cell-specific protein (e.g., Oct4) or alkaline phosphatase and one or more fibroblast-specific proteins. In still another aspect, the invention provides a cell that expresses one or more fibroblast-specific proteins and grows in aggregates, forms colonies, or forms embryoid bodies. Preferred fibroblast-specific proteins include cell adhesion molecules that e.g., promote anchoring of one or more reprogrammed cells to a site of interest in a host patient. Fibroblast-specific growth factors (e.g., the FGF family of proteins) are other exemplary fibroblast-specific proteins.

These methods for reprogramming cells are useful for the generation of cells of a desired cell type, for example, for medical applications. Accordingly, the invention also provides methods for the treatment or prevention of disease in a mammal that include administering a reprogrammed cell to the mammal. In one such method, the invention features a procedure for treating, stabilizing, or preventing a disease, disorder, or condition in a mammal. This method involves incubating a nucleus from a donor cell with a reprogramming media (e.g., a media having a T-cell factor or a T-cell extract) under conditions that allow the removal of a factor from the nucleus or the addition of a factor to the nucleus. The nucleus or a chromatin mass formed from the nucleus is inserted into a recipient cell or cytoplast, thereby forming a reprogrammed cell. The reprogrammed cell is then administered to the mammal in need of the cell type. In various embodiments, a nucleic acid encoding a TCR reactive with an antigen of interest is inserted into the nucleus, chromatin mass, or reprogrammed cell. In some embodiments, a reprogrammed cell expressing a TCR reactive with the antigen is selected or purified. In one preferred embodiment, the nucleus is incubated with an interphase reprogramming media. Preferably, the nucleus remains membrane-bounded, and the chromosomes in the nucleus do not condense during incubation with this interphase reprogramming media. In another preferred embodiment, a chromatin mass is formed from incubation of the nucleus in a mitotic reprogramming media. Preferably, this chromatin mass is then incubated in an interphase reprogramming media under conditions that allow a nucleus to be formed from the chromatin mass, and the reformed nucleus is inserted into the recipient cell or cytoplast. Preferably, the donor cell is from the mammal (for example, a human) in need of the cell type. Examples of diseases, disorders, or conditions that may be treated or prevented include neurological, endocrine, structural, skeletal, vascular, urinary, digestive, integumentary, blood, immune, autoimmune, inflammatory, metabolic, hormonal, endocrine, kidney, bladder, cardiovascular, cancer, circulatory, digestive, hematopoeitic, and muscular diseases, disorders, and conditions. Other exemplary conditions include bacterial, yeast, and viral infections. Still other conditions include having a higher than normal weight (e.g., clinical obesity) or having a higher than desired weight. In addition, reprogrammed cells may be used for reconstructive applications, such as for repairing or replacing tissues or organs.

In a related aspect, the invention provides another method of treating, stabilizing, or preventing a disease, disorder, or condition in a mammal (for example, a human). This method involves incubating a chromatin mass from a donor cell with a reprogramming media (e.g., a media having a T-cell factor or a T-cell extract) under conditions that allow the removal of a factor from the chromatin mass or the addition of a factor to the chromatin mass. The chromatin mass or a nucleus formed from incubating the chromatin mass in an interphase reprogramming media is inserted into a recipient cell or cytoplast, thereby forming a reprogrammed cell. The reprogrammed cell is then administered to a mammal in need of the cell type. In various embodiments, a nucleic acid encoding a TCR reactive with an antigen of interest is inserted into the nucleus, chromatin mass, or reprogrammed cell. In some embodiments, a reprogrammed cell expressing a TCR reactive with the antigen is selected or purified. In one preferred embodiment, the chromatin mass used in this method is generated by incubating a nucleus from a donor cell in a detergent and salt solution, in a protein kinase solution, or in a mitotic reprogramming media in the presence or absence of an antibody to NuMA. In another preferred embodiment, the chromatin mass is isolated from mitotic cells. Preferably, the donor cell is from the recipient mammal. Examples of diseases, disorders, or conditions that may be treated or prevented include neurological, endocrine, structural, skeletal, vascular, urinary, digestive, integumentary, blood, immune, autoimmune, inflammatory, metabolic, hormonal, endocrine, kidney, bladder, cardiovascular, cancer, circulatory, digestive, hematopoeitic, and muscular diseases, disorders, and conditions. Other exemplary conditions include bacterial, yeast, and viral infections; a higher than normal weight (e.g., clinical obesity); or a higher than desired weight. In addition, reprogrammed cells may be used for reconstructive applications, such as for repairing or replacing tissues or organs.

In still another related aspect, the invention provides another method of treating, stabilizing, or preventing a disease, disorder, or condition in a mammal (for example, a human) that involves incubating a permeabilized cell with a reprogramming media (e.g., a media having a T-cell factor or a T-cell extract) under conditions that allow the removal of a factor from the nucleus or chromatin mass of the permeabilized cell or the addition of a factor to the nucleus or chromatin mass, thereby forming a reprogrammed cell. In various embodiments, a nucleic acid encoding a TCR reactive with an antigen of interest is inserted into the nucleus, chromatin mass, or reprogrammed cell. In some embodiments, a reprogrammed cell expressing a TCR reactive with the antigen is selected or purified. The reprogrammed cell is administered to a mammal in need of that cell type. In one preferred embodiment, the permeabilized cell is incubated with an interphase reprogramming media. Preferably, the nucleus in the permeabilized cell remains membrane-bounded, and the chromosomes in the nucleus do not condense during incubation with the interphase reprogramming media. In another preferred embodiment, a chromatin mass is formed from incubation of the permeabilized cell in a mitotic reprogramming media. In yet another preferred embodiment, the reprogrammed cell is incubated under conditions that allow the membrane of the reprogrammed cell to reseal prior to being administered to the mammal. Preferably, the permeabilized cell is from the mammal in need of that cell type. In another preferred embodiment, the permeabilized cell is formed by incubating an intact cell with a detergent, such as digitonin, or a bacterial toxin, such as Streptolysin O. Examples of diseases, disorders, or conditions that may be treated or prevented include neurological, endocrine, structural, skeletal, vascular, urinary, digestive, integumentary, blood, immune, autoimmune, inflammatory, metabolic, hormonal, endocrine, kidney, bladder, cardiovascular, cancer, circulatory, digestive, hematopoeitic, and muscular diseases, disorders, and conditions. Other exemplary conditions include bacterial, yeast, and viral infections. Still other conditions include having a higher than normal weight (e.g., clinical obesity) or having a higher than desired weight. In addition, reprogrammed cells may be used for reconstructive applications, such as for repairing or replacing tissues or organs.

Exemplary cancers that can be treated, stabilized, or prevented using the above methods include prostate cancers, breast cancers, ovarian cancers, pancreatic cancers, gastric cancers, bladder cancers, salivary gland carcinomas, gastrointestinal cancers, lung cancers, colon cancers, melanomas, brain tumors, leukemias, lymphomas, and carcinomas. Benign tumors may also be treated or prevented using the methods and reprogrammed cells of the present invention.

In a further embodiment of any of the above aspects, administering a reprogrammed cell includes contacting an in-dwelling device with the cell prior to, concurrent with, or following the administration of the in-dwelling device to a patient. In-dwelling devices include, but are not limited to, surgical implants, prosthetic devices, and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, and continuous ambulatory peritoneal dialysis (CAPD) catheters.

In desirable embodiments, the viral infection relevant to the methods of the invention is an infection by one or more of the following viruses: Hepatitis, picornarirus, polio, HIV, coxsacchie, herpes simplex, St. Louis encephalitis, Epstein-Barr, myxovirus, JC, coxsakievirus B, togavirus, measles, paramyxovirus, echovirus, bunyavirus, cytomegalovirus, varicella-zoster, mumps, equine encephalitis, lymphocytic choriomeningitis, rabies, simian virus 40, human polyoma virus, parvovirus, papilloma virus, primate adenovirus, and/or BK.

In other desirable embodiments, the bacterial infection is due to one or more of the following bacteria: *Chlamydophila pneumoniae, C. psittaci, C. abortus, Chlamydia trachomatis, Simkania negevensis, Parachlamydia acanthamoebae, Pseudomonas aeruginosa, P. alcaligenes, P. chlororaphis, P. fluorescens, P. luteola, P. mendocina, P. monteilii, P. oryzihabitans, P. pertocinogena, P. pseudalcaligenes, P. putida, P. stutzeri, Burkholderia cepacia, Aeromonas hydrophilia, Escherichia coli, Citrobacter freundii, Salmonella typhimurium, S. typhi, S. paratyphi, S. enteritidis, Shigella dysenteriae, S. flexneri, S. sonnei, Enterobacter cloacae, E. aerogenes, Klebsiella pneumoniae, K. oxytoca, Serratia marcescens, Francisella tularensis, Morganella morganii, Proteus mirabilis, Proteus vulgaris, Providencia alcalifaciens, P. rettgeri, P. stuartii, Acinetobacter calcoaceticus, A. haemolyticus, Yersinia enterocolitica, Y. pestis, Y. pseudotuberculosis, Y. intermedia, Bordetella pertussis, B. parapertussis, B. bronchiseptica, Haemophilus influenzae, H. parainfluenzae, H. haemolyticus, H. parahaemolyticus, H. ducreyi, Pasteurella multocida, P. haemolytica, Branhamella catarrhalis, Helicobacter pylori, Campylobacter fetus, C. jejuni, C. coli, Borrelia burgdorferi, V. cholerae, V. parahaemolyticus, Legionella pneumophila, Listeria monocytogenes, Neisseria gonorrhea, N. meningitidis, Kingella dentrificans, K. kingae, K. oralis, Moraxella catarrhalis, M. atlantae, M. lacunata, M. nonliquefaciens, M. osloensis, M. phenylpyruvica, Gardnerella vaginalis, Bacteroides fragilis, Bacteroides distasonis,* Bacteroides 3452A homology group, *Bacteroides vulgatus, B. ovalus, B. thetaiotaomicron, B. uniformis, B. eggerthii, B. splanchnicus, Clostridium difficile, Mycobacterium tuberculosis, M. avium, M. intracellulare, M. leprae, C. diphtheriae, C. ulcerans, C. accolens, C. afermentans, C. amycolatum, C. argentorense, C. auris, C. bovis, C. confusum, C. coyleae, C. durum, C. falsenii, C. glucuronolyticum, C. imitans, C. jeikeium, C. kutscheri, C. kroppenstedtii, C. lipophilum, C. macginleyi, C. matruchoti, C. mucifaciens, C. pilosum, C. propinquum, C. renale, C. riegelii, C. sanguinis, C. singulare, C. striatum, C. sundsvallense, C. thomsenii, C. urealyticum, C. xerosis, Streptococcus pneumoniae, S. agalactiae, S. pyogenes, Enterococcus avium, E. casseliflavus, E. cecorum, E. dispar, E. durans, E. faecalis, E. faecium, E. flavescens, E. gallinarum, E. hirae, E. malodoratus, E. mundtii, E. pseudoavium, E. raffinosus, E. solitarius, Staphylococcus aureus, S. epidermidis, S. saprophyticus, S. intermedius, S. hyicus, S. haemolyticus, S. hominis,* and/or *S. saccharolyticus*. Preferably, a reprogrammed cell is administered in an amount sufficient to prevent, stabilize, or inhibit the growth of a pathogen or to kill the pathogen.

The invention also provides methods for measuring an endogenous activity (e.g., an endogenous enzymatic activity) or an endogenous protein in a cell, nucleus, chromatin mass, cell lysate, or in vitro sample. In one such aspect, the method involves contacting a solid support with a test sample from a cell, nucleus, chromatin mass, cell lysate, or in vitro sample, and with a reference sample. The test sample has an endogenous activity of interest that is naturally found in the test sample (e.g., luciferase activity or phosphatase activity, e.g., alkaline phosphatase activity), and the test sample has a known protein concentration or is derived from a known number of cells. The reference sample has a known level of the activity of interest (e.g., luciferase activity or phosphatase activity) or a known amount of naturally-occurring or recombinant protein having the activity. The level of luciferase or phosphatase activity in the test sample is measured and compared to the level of luciferase or phosphatase activity in the reference sample, thereby determining the level of luciferase or phosphatase activity in the cell, nucleus, chromatin mass, cell lysate, or in vitro sample. In one preferred embodiment, the luciferase or phosphatase activity is performed by a naturally-occurring protein encoded by an endogenous nucleic acid under the control of an endogenous promoter. This method may also be used to measure any other endogenous activity of interest. In another preferred embodiment, the activity is specific for one cell type or specific for a family of related cell types. In various embodiments, the activity of interest is the chemical alteration of one or more substrates to form a product. Preferably, either one of the substrates or one of the products is detectable. Detectable labels are well known in the art and include, without limitation, radioactive labels (e.g., isotopes such as $^{32}P$ or $^{35}S$) and nonradioactive labels (e.g., chemiluminescent labels or fluorescent labels, e.g., fluorescein).

In a related aspect, the invention provides a method for measuring the level of an endogenous protein in a cell, nucleus, chromatin mass, cell lysate, or in vitro sample. This method involves contacting a solid support with a test sample from a cell, nucleus, chromatin mass, cell lysate, or in vitro sample, and with a reference sample. The test sample has an endogenous, detectable protein of interest (e.g., luciferase, alkaline phosphatase, or Oct4) that is naturally found in the test sample, and the test sample has a known protein concentration or is derived from a known number of cells. The reference sample has a known amount of the protein of interest, e.g., naturally-occurring or recombinant luciferase, alkaline phosphatase, or Oct4 protein. The signal from the luciferase, alkaline phosphatase, or Oct4 protein in the test sample is measured and compared to the signal from the corresponding protein in the reference sample, thereby determining the amount of luciferase, alkaline phosphatase, or Oct4 protein in the cell, nucleus, chromatin mass, cell lysate, or in vitro sample. This method may also be used to measure the level of any other endogenous protein of interest. In one preferred embodiment, the protein of interest is encoded by an endogenous nucleic acid under the control of an endogenous promoter. In a preferred embodiment, the protein of interest is specific for one cell type or specific for a family of related cell types. In various embodiments, the protein of interest has a detectable label or binds another molecule (e.g., an antibody) with a detectable label. Exemplary detectable labels include radioactive labels (e.g., isotopes such as $^{32}P$ or $^{35}S$) and nonradioactive labels (e.g., chemiluminescent labels or fluorescent labels, e.g., fluorescein).

In preferred embodiments for the above methods of measuring the level of an activity or protein of interest, the solid support is contacted with multiple reference samples, each with a different level of activity or a different amount of the protein of interest. According to this embodiment, a standard curve may be generated from the reference samples and used to determine the level of activity or the amount of the protein of interest in the test sample. In various embodiments, the cell is a stem cell such as an embryonic stem cell or an adult stem cell from brain, blood, bone marrow, pancreas, liver, skin, or any other organ or tissue. In other embodiments, the cell has been exposed to an extract from a stem cell. In yet other embodiments, the test sample is a from a nuclear or cytoplasmic cell extract. Useful solid supports include any rigid or semi-rigid surface that may be contacted with the sample. The support can be any porous or non-porous water insoluble material, including, without limitation, membranes, filters, chips, slides, fibers, beads, gels, tubing, strips, plates, rods, polymers, particles, microparticles, capillaries, and plastic surfaces. If desired, the support can have a variety of surface forms, such as wells, trenches, pins, channels and pores, to which the samples are contacted.

In preferred embodiments of various aspects of the invention, at least 1, 5, 10, 15, 20, 25, 50, 75, 100, 150, 200, 300, or more mRNA or protein molecules are expressed in the reprogrammed cell that are not expressed in the donor or permeabilized cell. In another preferred embodiment, the number of mRNA or protein molecules that are expressed in the reprogrammed cell, but not expressed in the donor or permeabilized cell, is between 1 and 5, 5 and 10, 10 and 25, 25 and 50, 50 and 75, 75 and 100, 100 and 150, 150 and 200, or 200 and 300, inclusive. Preferably, at least 1, 5, 10, 15, 20, 25, 50, 75, 100, 150, 200, 300, or more mRNA or protein molecules are expressed in the donor or permeabilized cell that are not expressed in the reprogrammed cell. In yet another preferred embodiment, the number of mRNA or protein molecules that are expressed in the donor or permeabilized cell, but not expressed in the reprogrammed cell, is between 1 and 5, 5 and 10, 10 and 25, 25 and 50, 50 and 75, 75 and 100, 100 and 150, 150 and 200, or 200 and 300, inclusive. Preferably, the mRNA or protein molecules are specific for the cell type of the donor, permeabilized, or reprogrammed cell, such that the molecules are only expressed in cells of that particular cell type. In still another preferred embodiment, these mRNA or protein molecules are expressed in both the donor cell (i.e., the donor or permeabilized starting cell) and the reprogrammed cell, but the expression levels in these cells differ by at least 2, 5, 10, or 20-fold, as measured using standard assays (see, for example, Ausubel et al., Current Protocols in Molecular Biology, John Wiley & Sons, New York, 2000). In other embodiments, the expression of one or more cytoskeleton proteins such as integrins is decreased by at least at least 2, 5, 10, or 20-fold compared to the donor fibroblast cell. In yet other embodiments, the reprogrammed cell expresses a neurofilament protein, T-cell receptor (TCR) protein, IL-2, IL-2 receptor, insulin, or Oct4 at a level that is at least 2, 5, 10, or 20-fold greater that the corresponding level in the donor or permeabilized cell. Preferred TCRs specifically recognize and bind an antigen from a tumor cell, fat cell, autoimmune generated cell, autoantibody, or infectious pathogen. Preferably, reprogrammed cells expressing the TCR destroy the tumor cell, fat cell, autoimmune generated cell, autoantibody, or infectious pathogen. In other preferred embodiments, the reprogrammed cells expressing the TCR stimulate antigen presenting cells (APCs) such as B-cells, macrophages, and dendritic cells that present the antigen. The stimulated B-cells preferably express an antibody reactive with the antigen. In preferred embodiments, a therapeutic method of the invention results in a decrease of at least 10, 20, 30, 40, 50, 60, 70, 80, 90, or 95% in the number of tumor cells, fat cells, autoimmune generated cells, autoantibodies, or infectious pathogens in a mammal. In other embodiments, the reprogrammed cells are a polyclonal mixture or antiserum of reprogrammed cells (e.g., T-cells) that are specific for an antigen of interest.

In other preferred embodiments, the size of the donor or permeabilized cell differs from that of the reprogrammed cell by at least 10, 20, 30, 50, 75, or 100%, as measured using standard methods. In another preferred embodiment, the volume of cytoplasm in the donor or permeabilized cell differs from that in the reprogrammed cell by at least 10, 20, 30, 50, 75, or 100%, based on standard methods. In yet another preferred embodiment, the reprogrammed cell has gained or lost an activity relative to the donor or permeabilized cell, such as secretion of a particular hormone, extracellular matrix component, or antibody. In another embodiment, the reprogrammed cell has gained the ability to produce and secrete an interleukin such as IL-2, gained the ability to form a neurofilament, neurite, or axon, or gained the ability to form an embryoid body. In another embodiment, cell has gained the ability to express a T-cell receptor or IL-2 receptor or to produce insulin. Preferably, the β-chain of the IL-2 receptor is expressed constitutively, and the α-chain is expressed upon activation (e.g., by stimulation with an anti-CD3 antibody or by presentation of an antigen). In other embodiments, a reprogrammed cell such as a stem cell or fibroblast has gained the ability to contract, resembling a contracting muscle cell or beating heart cell.

In still other preferred embodiments, the reprogramming media is an interphase reprogramming media, such as an extract formed from cells synchronized in one or more of the following phases of the cell cycle: $G_0$, $G_1$, S, or $G_2$ phase. In another preferred embodiment, the reprogramming media is an extract formed from cells synchronized in mitosis or from unsynchronized cells. Preferably, the reprogramming media is an extract from the cell type one wishes the donor or permeabilized cell to become, or the reprogramming media is a solution containing factors specific for the cell type one wishes the donor or permeabilized cell to become. Examples of cells that may be used to generate extracts to reprogram cells into stem cells include embryonic stem cells and adult stem cells from brain, blood, bone marrow, pancreas, liver, skin, or any other organ or tissue. Preferably, the donor or permeabilized cell is an interphase or mitotic somatic cell. Preferred reprogramming medias include medias or extracts that contain at least 1, 2, 3, 5, 10, 15, 20, 30, 50, or more T-cell factors. In another preferred embodiment, the reprogramming media is modified by the enrichment or depletion of a factor, such as a TCR, DNA methyltransferase, histone deacetylase, histone, nuclear lamin, transcription factor, activator, repressor, growth factor, hormone, or cytokine. The concentration of exogenous or endogenous TCR mRNA in the reprogramming media is preferably at least 1 nM, 10 nM, 100 nM, 500 nM, 1 μM, 10 μM, 100 μM, 500 μM, 1 mM, 10 mM, 100 mM, 200 mM, or 500 mM. The concentration of TCR alpha and/or beta protein subunits added to, or expressed by, the reprogramming media is preferably at least 1 ng/ml, 10 ng/ml, 100 ng/ml, 500 ng/ml, 1 μg/ml, 10 μg/ml, 100 μg/ml, 500 μg/ml, 1 mg/ml, 10 mg/ml, 20 mg/ml, 50 mg/ml, or 100 mg/ml. In certain embodiments, the concentration of TCR RNA and/or protein in the reprogramming media is between 1 and 100 ng/mL, 100 and 1000 ng/mL, 1 and 100 1 μg/mL, 100 and 1000 1 μg/mL, 1 and 100 mg/mL, or 100 and 1000 mg/mL, inclusive. The reprogramming media may or may not contain exogenous nucleotides. In other preferred embodiments, a chromatin mass in a reprogramming media or formed in a permeabilized cell is contacted with a vector having a nucleic acid encoding a gene of interest under conditions that allow homologous recombination between the nucleic acid in the vector and the corresponding nucleic acid in the genome of the chromatin mass, resulting in the alteration of the genome of the chromatin mass. Due to the lack of an intact plasma membrane and the lack of a nuclear membrane, a chromatin mass in a permeabilized cell may be easier to genetically modify than a naturally-occuring cell. Preferably, the chromatin mass or nucleus is purified from the reprogramming media prior to insertion into the recipient cell or cytoplast, or the reprogrammed cell is purified prior to administration into the mammal. Preferably, the donor or permeabilized cell is haploid (DNA content of n), diploid (2n), or tetraploid (4n), and the recipient cell is hypodiploid (DNA content of less than 2n), haploid, or enucleated.

Preferred donor cells, permeabilized cells, recipient cells, reprogrammed cells, and sources of cytoplasts include differentiated cells, such as epithelial cells, neural cells, epidermal cells, keratinocytes, hematopoietic cells, melanocytes, chondrocytes, B-cells, T-cells, erythrocytes, macrophages, monocytes, fibroblasts, and muscle cells; and undifferentiated cells, such as embryonic or adult stem cells. In another preferred embodiment, the donor or permeabilized cell is a differentiated cell, and the reprogrammed cell is a differentiated cell of another cell type. In yet another preferred embodiment, the donor or permeabilized cell is an undifferentiated cell, and the reprogrammed cell is a differentiated cell. In still another preferred embodiment, the donor or permeabilized cell is a differentiated cell, and the reprogrammed cell is an undifferentiated cell. If desired, an undifferentiated reprogrammed cell may be induced to differentiate into a desired cell type in vitro using standard methods, such as by exposure to certain growth factors, hormones, interleukins, cytokines, or other cells. In another preferred embodiment, the undifferentiated reprogrammed cell differentiates into a desired cell type in vivo after administration to a mammal. In yet another preferred embodiment, the donor or permeabilized cell is a B-cell, Jurkat cell, endothelial cell, epithelial cell, or fibroblast, and the reprogrammed cell is a T-cell. It is also contemplated that the nucleus or chromatin mass may be inserted into a recipient cell or cytoplast of the desired cell type or of the same cell type as the donor or permeabilized cell. In still another preferred embodiment, the donor cell, permeabilized cell, recipient cell, or recipient cytoplast is from a human or non-human mammal. In yet another preferred embodiment, the donor nucleus or chromatin mass is from a transgenic cell or mammal or contains a mutation not found in the donor cell or not found in a naturally-occurring cell. The donor or permeabilized cell can be non-immortalized or naturally, spontaneously, or genetically immortalized. The donor cell, permeabilized cell, recipient cell, or cytoplast can be from a source of any age, such as an embryo, fetus, youth, or adult mammal. Cells from younger sources may have acquired fewer spontaneous mutations and may have a longer life-span in vitro or after transplantation in vivo.

Preferably, a disease-causing mutation in a regulatory region, promoter, untranslated region, or coding region of a gene in a donor nucleus or chromatin mass is modified to replace the mutant sequence with a sequence that is not associated with the disease. Alternatively, a nucleic acid is inserted into the donor nucleus or chromatin mass that includes a promoter operably-linked to a sequence of the gene that does not contain a mutation associated with a disease. Preferably, the sequence of the gene is substantially identical to that of a naturally-occurring gene that does, not contain a polymorphism or mutation associated with a disease. Examples of mutations that may be rescued using these methods include mutations in the cystic fibrosis gene; mutations associated with Dunningan's disease such as the R482W, R482Q, and R584H mutations in the lamin A gene; and mutations associated with the autosomal-dominant form of Emery Deyfuss muscular dystrophy such as the R249Q, R453W, and Q6STOP mutations in the lamin A gene. In the Q6STOP mutation, the codon for Gln6 is mutated to a stop codon.

Preferred transgenic donor nuclei, chromosomes, or chromatin masses encode a heterologous MHC Class I protein having an amino acid sequence substantially identical to the sequence of an MHC Class I protein found in the mammal to whom the reprogrammed cells will be administered for therapeutic applications. Alternatively, the donor nuclei or chromatin masses may encode a heterologous MHC Class 1 protein having an amino acid sequence substantially identical to the sequence of an MHC Class 1 protein found in another mammal of the same genus or species as the recipient mammal. Reprogrammed cells that express such MHC proteins are less likely to elicit an adverse immune response when administered to the mammal. Other preferred donor nuclei or chromatin masses are modified to express a heterologous protein that inhibits the complement pathway of the recipient mammal, such as the human complement inhibitor CD59 or the human complement regulator decay accelerating factor (h-DAF) (see, for example, Ramirez et al., Transplantation 15:989-998, 2000; Costa et al., Xenotransplantation 6:6-16, 1999). In yet another preferred embodiment, the donor nucleus or chromatin mass has a mutation that reduces or eliminates the expression or activity of a galactosyltransferase, such as alpha(1,3)-galactosyltransferase (Tearle et al., Transplantation 61:13-19, 1996; Sandrin, Immunol. Rev. 141:169-190, 1994; Costa et al., Xenotransplantation 6:6-16, 1999). This enzyme modifies cell surface molecules with a carbohydrate that elicits an adverse immune response when cells expressing this galactose alpha(1,3)-galactose epitope are administered to humans. Thus, reprogrammed cells that have a lower level of expression of this epitope may have a lower incidence of rejection by the recipient mammal.

With respect to the therapeutic methods of the invention, it is not intended that the administration of reprogrammed cells to a mammal be limited to a particular mode of administration, dosage, or frequency of dosing; the present invention contemplates all modes of administration, including intramuscular, intravenous, intraarticular, intralesional, subcutaneous, or any other route sufficient to provide a dose adequate to prevent or treat a disease. Preferably, the cells are administered to the mammal from which the donor or permeabilized cell is obtained. Alternatively, the donor or permeabilized cell may be obtained from a different donor mammal of the same or a different genus or species as the recipient mammal. Examples of preferred donor mammals include humans, cows, sheep, big-horn sheep, goats, buffalos, antelopes, oxen, horses, donkeys, mule, deer, elk, caribou, water buffalo, camels, llama, alpaca, rabbits, pigs, mice, rats, guinea pigs, hamsters, dogs, cats, and primates such as monkeys. The cells may be administered to the mammal in a single dose or multiple doses. When multiple doses are administered, the doses may be separated from one another by, for example, one week, one month, one year, or ten years. One or more growth factors, hormones, interleukins, cytokines, or other cells may also be administered before, during, or after administration of the cells to further bias them towards a particular cell type. Additionally, one or more immunosuppressive agents, such as cyclosporin, may be administered to inhibit rejection of the transplanted cells. It is to be understood that, for any particular subject, specific dosage regimes should be adjusted over time according to the individual need and the professional judgment of the person administering or supervising the administration of the compositions. If desired, conventional treatments such as chemotherapeutic agents, antibiotics, appetite suppressants, diet, and exercise may be used in combination with the reprogrammed cells of the present invention.

It is also contemplated that a T-cell reactive with an antigen of interest can be generated without reprogramming a donor cell, chromatin mass, or nucleus. For example, a T-cell can be obtained from a patient, and the endogenous nucleic acid encoding a TCR can be replaced using standard homologous replacement methods by a nucleic acid encoding a TCR reactive with the antigen of interest (see, for example, U.S. Pat. No. 5,631,153; filed Jun. 5, 1995).

As used herein, by "chromatin mass" is meant more than one chromosome not enclosed by a membrane. Preferably, the chromatin mass contains all of the chromosomes of a cell. A chromatin mass containing condensed chromosomes may be formed by exposure of a nucleus to a mitotic reprogramming media (e.g., a mitotic extract), or a chromatin mass may be isolated from mitotic cells as described herein. Alternatively, a chromatin mass containing decondensed or partially condensed chromosomes may be generated by exposure of a nucleus to one of the following, as described herein: a mitotic reprogramming media (e.g., a mitotic extract) in the presence of an anti-NuMA antibody, a detergent and salt solution, or a protein kinase solution.

A chromatin mass may be formed naturally or artificially induced. An exemplary naturally-occurring chromatin mass includes a set of metaphase chromosomes, which are partially or maximally condensed chromosomes that are not surrounded by a membrane and that are found in, or isolated from, a mitotic cell. Preferably, the metaphase chromosomes are discrete chromosomes that are not physically touching each other. Exemplary artificially induced chromatin masses are formed from exposure to a reprogramming media, such as a solution containing factors that promote chromosome condensation, a mitotic extract, a detergent and salt solution, or a protein kinase solution. Artificially induced chromatin masses may contain discrete chromosomes that are not physically touching each other or may contain two or more chromosomes that are in physical contact.

If desired, the level of chromosome condensation may be determined using standard methods by measuring the intensity of staining with the DNA stain, DAPI. As chromosomes condense, this staining intensity increases. Thus, the staining intensity of the chromosomes may be compared to the staining intensity for decondensed chromosomes in interphase (designated 0% condensed) and maximally condensed chromosomes in mitosis (designated 100% condensed). Based on this comparison, the percent of maximal condensation may be determined. Preferred condensed chromatin masses are at least 50, 60, 70, 80, 90, or 100% condensed. Preferred decondensed or partially condensed chromatin masses are less than 50, 40, 30, 20, or 10% condensed.

By "nucleus" is meant a membrane-bounded organelle containing most or all of the DNA of a cell. The DNA is packaged into chromosomes in a decondensed form. Preferably, the membrane encapsulating the DNA includes one or two lipid bilayers or has nucleoporins.

By "donor cell" is meant a cell from which a nucleus or chromatin mass is derived.

By "cytoplast" is meant a membrane-enclosed cytoplasm. Preferably, the cytoplast does not contain a nucleus, chromatin mass, or chromosome. Cytoplasts may be formed using standard procedures. For example, cytoplasts may be derived from nucleated or enucleated cells. Alternatively, cytoplasts may be generated using methods that do not require an intact cell to be used as the source of the cytoplasm or as the source of the membrane. In one such method, cytoplasts are produced by the formation of a membrane in the presence of cytoplasm under conditions that allow encapsulation of the cytoplasm by the membrane.

By "permeabilization" is meant the formation of pores in the plasma membrane or the partial or complete removal of the plasma membrane.

By "reprogramming media" is meant a solution that allows the removal of a factor from a nucleus, chromatin mass, or chromosome or the addition of a factor from the solution to the nucleus, chromatin mass, or chromosome. Preferably, the addition or removal of a factor increases or decreases the level of expression of an mRNA or protein in the donor cell, chromatin mass, or nucleus or in a cell containing the reprogrammed chromatin mass or nucleus. In another embodiment, incubating a permeabilized cell, chromatin mass, or nucleus in the reprogramming media alters a phenotype of the permeabilized cell or a cell containing the reprogrammed chromatin mass or nucleus relative to the phenotype of the donor cell. In yet another embodiment, incubating a permeabilized cell, chromatin mass, or nucleus in the reprogramming media causes the permeabilized cell or a cell containing the reprogrammed chromatin mass or nucleus to gain or loss an activity relative to the donor cell.

Exemplary reprogramming medias include solutions, such as buffers, that do not contain biological molecules such as proteins or nucleic acids. Such solutions are useful for the removal of one or more factors from a nucleus, chromatin mass, or chromosome. Other preferred reprogramming medias are extracts, such as cellular extracts from cell nuclei, cell cytoplasm, or a combination thereof. Yet other reprogramming medias are solutions or extracts to which one or more naturally-occurring or recombinant factors (e.g., nucleic acids or proteins such as T-cell receptors or other surface signaling molecules, DNA methyltransferases, histone deacetylases, histones, nuclear lamins, transcription factors, activators, repressors, growth factors, hormones, or cytokines) have been added, or extracts from which one or more factors have been removed. Still other reprogramming medias include detergent and salt solutions and protein kinase solutions. In some embodiments, the reprogramming media contains an anti-NuMA antibody. By "interphase reprogramming media" is meant a media (e.g., an interphase cell extract) that induces chromatin decondensation and nuclear envelope formation. By "mitotic reprogramming media" is meant a media (e.g., a mitotic cell extract) that induces chromatin condensation and nuclear envelope breakdown. If desired, multiple reprogramming media may be used simultaneously or sequentially to reprogram a donor cell, nucleus, or chromatin mass.

By "addition of a factor" is meant the binding of a factor to chromatin, a chromosome, or a component of the nuclear envelope, such as the nuclear membrane or nuclear matrix. Alternatively, the factor is imported into the nucleus so that it is bounded or encapsulated by the nuclear envelope. Preferably, the amount of factor that is bound to a chromosome or located in the nucleus increases by at least 25, 50, 75, 100, 200, or 500%.

By "removal of factor" is meant the dissociation of a factor from chromatin, a chromosome, or a component of the nuclear envelope, such as the nuclear membrane or nuclear matrix. Alternatively, the factor is exported out of the nucleus so that it is no longer bounded or encapsulated by the nuclear envelope. Preferably, the amount of factor that is bound to a chromosome or located in the nucleus decreases by at least 25, 50, 75, 100, 200, or 500%.

By "enrichment or depletion of a factor" is meant the addition or removal of a naturally-occurring or recombinant factor by at least 20, 40, 60, 80, or 100% of the amount of the factor originally present in the reprogramming media. Alternatively, a naturally-occurring or recombinant factor that is not naturally present in the reprogramming media may be added. Preferred factors include proteins such as T-cell receptors or other signaling surface molecules, DNA methyltransferases, histone deacetylases, histones, nuclear lamins, transcription factors, activators, repressors, growth factors, cytokines, and hormones; membrane vesicles; and organelles. In one preferred embodiment, the factor is purified prior to being added to the reprogramming media, as described below. Alternatively, one of the purification methods described below may be used to remove an undesired factor from the reprogramming media.

By "purified" is meant separated from other components that naturally accompany it. Typically, a factor is substantially pure when it is at least 50%, by weight, free from proteins, antibodies, and naturally-occurring organic molecules with which it is naturally associated. Preferably, the factor is at least 75%, more preferably, at least 90%, and most preferably, at least 99%, by weight, pure. A substantially pure factor may be obtained by chemical synthesis, separation of the factor from natural sources, or production of the factor in a recombinant host cell that does not naturally produce the factor. Proteins, vesicles, chromosomes, nuclei, and other organelles may be purified by one skilled in the art using standard techniques such as those described by Ausubel et al. (Current Protocols in Molecular Biology, John Wiley & Sons, New York, 2000). The factor is preferably at least 2, 5, or 10 times as pure as the starting material, as measured using polyacrylamide gel electrophoresis, column chromatography, optical density, HPLC analysis, or western analysis (Ausubel et al., supra). Preferred methods of purification include immunoprecipitation, column chromatography such as immunoaffinity chromatography, magnetic bead immunoaffinity purification, and panning with a plate-bound antibody.

By "mRNA or protein specific for one cell type" is meant an mRNA or protein that is expressed in one cell type at a level that is at least 10, 20, 50, 75, or 100 fold greater than the expression level in all other cell types. Preferably, the mRNA or protein is only expressed in one cell type.

By "T-cell receptor (TCR) specific for an antigen" is meant a TCR which recognizes and binds an antigen of interest, but which does not substantially recognize and bind other molecules in a sample, e.g., a biological sample, which naturally includes other proteins or cells. The signal in a standard ELISA assay for the binding of the TCR to an antigen of interest is desirably at least 2, 3, 4, 5, 10, 15, 20, 30, 40, 50, 60, 70, 80, 90, 100, 150, 200, or 500 times greater than that for (i) the binding of a control cell that does not express the TCR (e.g., a cell that does not express a TCR or that expresses a TCR with less than 80, 70, 60, 50, 40, 30, or 20% sequence identity to the TCR of interest) to the antigen or (ii) the binding of the TCR to a control molecule that has less than 80, 70, 60, 50, 40, 30, or 20% sequence identity to the antigen of interest.

By "mutation" is meant an alteration in a naturally-occurring or reference nucleic acid sequence, such as an insertion, deletion, frameshift mutation, silent mutation, nonsense mutation, or missense mutation. Preferably, the amino acid sequence encoded by the nucleic acid sequence has at least one amino acid alteration from a naturally-occurring sequence. Examples of recombinant DNA techniques for altering the genomic sequence of a cell, embryo, fetus, or mammal include inserting a DNA sequence from another organism (e.g., a human) into the genome, deleting one or more DNA sequences, and introducing one or more base mutations (e.g., site-directed or random mutations) into a target DNA sequence. Examples of methods for producing these modifications include retroviral insertion, artificial chromosome techniques, gene insertion, random insertion with tissue specific promoters, homologous recombination, gene targeting, transposable elements, and any other method for introducing foreign DNA. All of these techniques are well known to those skilled in the art of molecular biology (see, for example, Ausubel et al., supra). Chromatin masses, chromosomes, and nuclei from transgenic cells, tissues, organs, or mammals containing modified DNA may be used in the methods of the invention.

By "substantially identical" is meant having a sequence that is at least 60, 70, 80, 90, or 100% identical to that of another sequence or to a naturally-occurring sequence. Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications.

By "immortalized" is meant capable of undergoing at least 25, 50, 75, 90, or 95% more cell divisions than a naturally-occurring control cell of the same cell type, genus, and species as the immortalized cell or than the donor cell from which the immortalized cell was derived. Preferably, an immortalized cell is capable of undergoing at least 2, 5, 10, or 20-fold more cell divisions than the control cell. More preferably, the immortalized cell is capable of undergoing an unlimited number of cell divisions. Examples of immortalized cells include cells that naturally acquire a mutation in vivo or in vitro that alters their normal growth-regulating process. Other preferred immortalized cells include hybridoma cells which are generated using standard techniques for fusion of a myeloma with a B-cell (Mocikat, J. Immunol. Methods 225:185-189, 1999; Jonak et al., Hum. Antibodies Hybridomas 3:177-185, 1992; Srikumaran et al., Science 220:522, 1983). Still other preferred immortalized cells include cells that have been genetically modified to express an oncogene, such as ras, myc, abl, bcl2, or neu, or that have been infected with a transforming DNA or RNA virus, such as Epstein Barr virus or SV40 virus (Kumar et al., Immunol. Lett. 65:153-159, 1999; Knight et al., Proc. Nat. Acad. Sci. USA 85:3130-3134, 1988; Shammah et al., J. Immunol. Methods 160-19-25, 1993; Gustafsson and Hinkula, Hum. Antibodies Hybridomas 5:98-104, 1994; Kataoka et al., Differentiation 62:201-211, 1997; Chatelut et al., Scand. J. Immunol. 48:659-666, 1998). Cells can also be genetically modified to express the telomerase gene (Roques et al., Cancer Res. 61:8405-8507, 2001).

By "non-immortalized" is meant not immortalized as described above.

By "treating, stabilizing, or preventing a disease, disorder, or condition" is meant preventing or delaying an initial or subsequent occurrence of a disease, disorder, or condition; increasing the disease-free survival time between the disappearance of a condition and its reoccurrence; stabilizing or reducing an adverse symptom associated with a condition; or inhibiting or stabilizing the progression of a condition. Preferably, at least 20, 40, 60, 80, 90, or 95% of the treated subjects have a complete remission in which all evidence of the disease disappears. In another preferred embodiment, the length of time a patient survives after being diagnosed with a condition and treated with a reprogrammed cell of the invention is at least 20, 40, 60, 80, 100, 200, or even 500% greater than (i) the average amount of time an untreated patient survives or (ii) the average amount of time a patient treated with another therapy survives.

By "treating, stabilizing, or preventing cancer" is meant causing a reduction in the size of a tumor, slowing or preventing an increase in the size of a tumor, increasing the disease-free survival time between the disappearance of a tumor and its reappearance, preventing an initial or subsequent occurrence of a tumor, or reducing or stabilizing an adverse symptom associated with a tumor. In one preferred embodiment, the percent of cancerous cells surviving the treatment is at least 20, 40, 60, 80, or 100% lower than the initial number of cancerous cells, as measured using any standard assay. Preferably, the decrease in the number of cancerous cells induced by administration of a reprogrammed cell of the invention is at least 2, 5, 10, 20, or 50-fold greater than the decrease in the number of non-cancerous cells. In yet another preferred embodiment, the number of cancerous cells present after administration of a reprogrammed cell is at least 2, 5, 10, 20, or 50-fold lower than the number of cancerous cells present after administration of a vehicle control. Preferably, the methods of the present invention result in a decrease of 20, 40, 60, 80, or 100% in the size of a tumor as determined using standard methods. Preferably, at least 20, 40, 60, 80, 90, or 95% of the treated subjects have a complete remission in which all evidence of the cancer disappears. Preferably, the cancer does not reappear or reappears after at least 5, 10, 15, or 20 years. In another preferred embodiment, the length of time a patient survives after being diagnosed with cancer and treated with a reprogrammed cell of the invention is at least 20, 40, 60, 80, 100, 200, or even 500% greater than (i) the average amount of time an untreated patient survives or (ii) the average amount of time a patient treated with another therapy survives.

By "treating, stabilizing, or preventing a higher than desired total body weight or higher than desired percentage of body fat" is meant preventing or delaying an initial or subsequent occurrence of a higher than desired weight or percentage of body fat, or stabilizing or reducing a subject's total body weight or percentage of body fat. Obesity is typically classified as mild (i.e., 20 to 40% overweight based on the midpoint of the weight range for the subject's height on a standard height-weight table), moderate (i.e., 41 to 100% overweight), or severe (i.e., over 100% overweight). In some embodiments, the subject's body mass index is greater than 20, 25, 30, 35, 40, or 45 kg/M$^2$. In certain embodiments, the subject has an increased body weight or an increased percentage of body fat due to, at least in part, a hormonal or metabolic disorder (e.g., a thyroid disorder), brain damage (e.g., damage to the hypothalamus), an adverse side-effect from a medication, or a genetic factor. In some embodiments, the subject has a binge eating disorder, bulimia nervosa, or anorexia nervosa.

Desirably, administration of the reprogrammed cells of the present invention (e.g., cells reactive with one or more antigens expressed on fat cells) to the subject results in a decrease of at least 5, 10, 20, 30, 40, 50, or 60% in the subject's total body weight or weight due to body fat. Preferably, the decrease in muscle mass is less than 50, 40, 30, 20, 10, 5, or 3%. In other preferred embodiments, the decrease in body fat or total body weight leads to a decrease in blood pressure, incidence or severity of diabetes, or incidence or severity of coronary artery disease (e.g., heart attacks).

By "autoimmune disease" is meant a disease in which an immune system response is generated against self epitopes. Some examples of autoimmune diseases include insulin dependent diabetes mellitus, rheumatoid arthritis, pemphigus vulgaris, multiple sclerosis, and myasthenia gravis.

By "bacterial infection" is meant the invasion of a host mammal by pathogenic bacteria. For example, the infection may include the excessive growth of bacteria that are normally present in or on the body of a mammal or growth of bacteria that are not normally present in or on the mammal. More generally, a bacterial infection can be any situation in which the presence of a bacterial population(s) is damaging to a host mammal. Thus, a mammal is "suffering" from a bacterial infection when an excessive amount of a bacterial population is present in or on the mammal's body, or when the presence of a bacterial population(s) is damaging the cells or other tissue of the mammal. In one embodiment, the number of a particular genus or species of bacteria is at least 2, 4, 6, or 8 times the number normally found in the mammal. The bacterial infection may be due to gram positive and/or gram negative bacteria.

By "mammal in need of a cell type" is meant a mammal in which a disease, disorder, or condition is treated, stabilized, or prevented by the administration of a reprogrammed cell of the invention. Exemplary mammals include mammals that have a reduced amount of functional cells of a particular cell type. Other examples of mammals include those with cancer, an infection, an autoimmune disease, or excess fat.

The present invention provides a number of advantages related to the alteration of cell fate. For example, these methods may be generally applied to produce large numbers of cells of any desired cell type, (e.g., T-cells expressing a TCR specific for an antigen of interest). Because these methods involve incubating a nucleus, a chromatin mass, or a permeabilized cell in a reprogramming media (e.g., a T-cell extract) to allow reprogramming, the efficiency of reprogramming may be enhanced by adding factors to the reprogramming media that facilitate reprogramming or by removing factors that inhibit reprogramming. These reprogrammed cells may be transplanted into mammals for the treatment or prevention of conditions involving damage or deficiency of a particular cell type or conditions in which increased levels of a specific cell type are desirable (e.g., conditions such as cancer or conditions in which replacement and/or increasing numbers of T-cells are desirable, such as common variable immuno deficiency (CVI), aquired immuno deficiency syndrom (AIDS), and other related immune dysfunction conditions). Additionally, reprogrammed cells that express a TCR that binds an antigen on fat cells are useful for reducing or stabilizing the amount of body fat in a mammal. These methods are desirable because they may be used to obtain a significant, long-term reduction in body fat. Reprogrammed cells that express a TCR specific for an autoimmune generated cell or an autoantibody are also useful for the prevention or treatment of autoimmune disease. If desired, the reprogrammed cells may be manipulated using standard molecular biology techniques to correct a disease-causing mutation before administering the cells to a recipient mammal.

Moreover, reprogrammed cells that are transplanted into the mammal from which the donor cells were obtained are unlikely to express foreign antigens and thus are unlikely to induce an adverse immune response that results in rejection of the transplanted cells. In contrast, in many traditional allogenic transplantation methods, foreign class I and II MHC molecules are present on the surfaces of the transplanted cells. These molecules are polymorphic and may not match the recipient. The foreign antigens are processed by antigen-presenting cells and presented to naive T-cells. These stimulated T-cells proliferate and differentiate into helper and cytotoxic effector T-cells that kill the transplanted cells and stimulate B-cells to produce antibodies that are reactive with the foreign antigens.

Other features and advantages of the invention will be apparent from the following detailed description and from the claims.

BRIEF DESCRIPTION OF THE DRAWINGS

The application file contains drawings executed in color (FIGS. 13, 14A, 14B, 14C, 15, 17A, and 23A-23E). Copies of this patent or patent application with color drawings will be provided by the Office upon request and payment of the necessary fee.

FIG. 8A is a picture of nuclei purified from quiescent T-cells ("Input nuclei") and incubated in stimulated extract for 30 minutes. Nuclear integrity was assessed by phase contrast microscopy and membrane labeling with 10 µg/ml of the lipophilic dye $DiOC_6$ (bar, 10 µm). FIG. 8B is a picture of an immunoblot showing the relative levels of NFAT, AP-1, NFκB, Oct-1, Erk, and an exogenous BSA-NLS conjugate in input resting T-cell nuclei ("Input nuclei"), input unstimulated extract, and input stimulated extract. Nuclear uptake of these factors was examined in nuclei exposed to stimulated extract, unstimulated extract, or stimulated extract containing the nuclear pore blocking antibody mAb414. Blots were also probed using anti-histone H4 antibodies as a gel loading control. FIG. 8C is a graph of the immunoblotting analysis of intranuclear anchoring of imported transcription factors in nuclei exposed to unstimulated extract or stimulated extract. Intranuclear anchoring was assessed using a nuclear retention assay and immunoblotting analysis of Triton X-100 insoluble ("bound") fractions. The percentage (mean±SD) of bound factors was determined by densitometric analysis of duplicate blots. FIG. 8D is a picture of immunoblotting analysis of nuclear matrix ("Mtx") and chromatin ("Chr") fractions prepared from nuclei exposed to stimulated extract. NuMA and RNA Pol IIo were used as markers of the nuclear matrix and chromatin, respectively. Anti-NuMA antibodies and anti-Pol IIo mAb CC3 were gifts from D. Compton (Dartmouth Medical School, Hanover, N.H., USA) and M. Vincent (Université Laval, Quebec, Canada), respectively.

FIG. 9A is a gel showing the anchoring of the chromatin remodeling complex SWI/SNF in nuclei exposed to stimulated extract. Purified quiescent T-cell nuclei ("Input nuclei") were incubated in cell lysis buffer ("Buffer"), unstimulated extract, or stimulated extract for 30 minutes, and sedimented through sucrose. Free and bound SWI/SNF fractions were assessed using the nuclear retention assay and immunoblotting with anti-BRG1 antibodies. FIG. 9B is a graph of the percentage of bound SWI/SNF, as determined using the nuclear retention assay during incubation of nuclei in stimulated extract or unstimulated extract. FIG. 9C is a gel showing nuclear retention of SWI/SNF in cultured stimulated T-cells. T-cells were stimulated with anti-CD3 antibodies and after 30 minutes, intranuclear bound and free fractions of SWI/SNF were assessed as in FIG. 9A. FIG. 9D is a graph of the ATPase activity of the SWI/SNF complex. After incubation of resting T-cell nuclei in stimulated extract or unstimulated extract for 30 minutes, SWI/SNF was immunoprecipitated from nuclear lysates using anti-BRG1 antibodies and hydrolysis of 1 nM exogenous ATP ("ATP+") by the immune precipitate ("BRG1-IP") was determined in a luminometric assay. Control precipitations were carried out using pre-immune IgGs ("Pre-I IgG"). Top rows show an anti-BRG1 immunoblot of the BRG1-IPs. Where indicated, BRG1-IP was treated with 100 μg/ml DNAse I for 15 minutes prior to the assay ("DNAse+"). Relative ATPase activities are expressed as mean (±SD) relative light units (RLU) in the assay subtracted to the RLU of the control pre-immune precipitate (RLU=2, 700, set to zero). FIG. 9E is a gel showing the hyperacetylation of the IL-2 promoter in T-cell nuclei in culture and in vitro. Microccocal nuclease-soluble chromatin ("Input") was prepared from unstimulated ("Unstim.") and anti-CD3-stimulated ("Stim.") T-cells. AcH4 was immunoprecipitated, and DNA isolated from anti-acH4 precipitates ("Bound") and supernatant ("Unbound") fractions. DNA was dot-blotted and hybridized with an IL-2 promoter-specific probe and a control β-actin probe.

FIG. 10A is a gel showing transcription by resting T-cell nuclei ("Input nuclei") incubated in stimulated extract ("Nuclei-SE") or unstimulated extract ("Nuclei-USE"). As controls, nuclei were incubated in stimulated extract containing either 100 μg/ml RNAse A, 100 μg/ml DNAse I, mAb414, or wheat germ agglutinin ("WGA"). At the end of the incubation, total RNA was isolated from the reaction mix, and 15 ng was used as the template for RT-PCR using IL-2-specific primers. Input stimulated extract and stimulated extract containing 1.2 μg total RNA isolated from IL-2 producing T-cells ("Pos. control SE") were analyzed as controls. FIG. 10B is a picture of a gel showing that IL-2 mRNA synthesis in vitro is RNA Pol II-dependent. Resting T-cell nuclei were exposed to stimulated extract containing 0, 5, 10, 50, 100 or 500 nM of the RNA Pol II inhibitor, actinomycin D. IL-2 mRNA synthesis was analyzed by RT-PCR at the end of incubation. FIG. 10C is a gel showing transcription by nuclei from primary HUVEC cells, NT2 cells, and Hela cells that were reprogrammed for 2 hours in stimulated extract or unstimulated extract. As controls, nuclei were incubated in stimulated extract containing either 100 μg/ml RNAse A, mAb414, or 50 nM actinomycin D ("ActD"). Total RNA was isolated, and IL-2 RNA synthesis was examined by RT-PCR. FIG. 10D is a picture of a gel showing transcription by resting T-cell nuclei that were incubated for two hours in stimulated extract, or in extracts from 293T, HeLa, or BjaB-cells, all prepared after treating each cell type with anti-CD3 and cross-linking antibodies to mimic T-cell stimulation. IL-2 mRNA synthesis in each extract was analyzed by RT-PCR.

FIG. 11A is a picture of nuclei purified from 293T fibroblasts (0 min) and incubated in stimulated T-cell extract. Uptake of NFAT was examined by immunofluorescence (bar, 10 μm). FIG. 11B is a picture of immunoblotting analysis showing nuclear uptake of NFAT, AP-1, NFκB, Oct-1, and BSA-NLS in input 293T nuclei and 293T nuclei exposed to either stimulated T-cell extract, unstimulated T-cell extract, or stimulated T-cell extract and mAb414. Anti-histone H4 antibodies were used as a loading control. FIG. 11C is a picture of an immunoblot showing nuclear matrix ("Mtx") and chromatin ("Chr") fractions prepared from 293T nuclei treated with stimulated T-cell extract.

FIGS. 12A-2E demonstrate chromatin remodeling and activation of the IL-2 gene in stimulated T-cell extract. FIG. 12A is a gel showing intranucleuear anchoring of the human SWI/SNF complex. In the left section of the immunoblot, nuclei were isolated from resting ("−") or anti-CD3-stimulated ("α-CD3") T-cells, and intranuclear free and bound SWI/SNF assessed by immunoblotting of detergent-soluble and insoluble nuclear fractions using anti-BRG1 antibodies. In the right section of the immunoblot, free and bound SWI/SNF fractions were visualized in 293T nuclei incubated in stimulated T-cell extract and sedimented through sucrose.

FIG. 14A is a picture of 293t cells exposed to a control 293T extract (top row) or a stimulated Jurkat-TAg extract (middle row), and Jurkat-TAg cells (bottom row) and analyzed by immunofluorescence using indicated FITC-conjugated antibodies. CD3, CD4, CD8 were detected at four days post-reprogramming; CD45 was detected at 11 days post-reprogramming. The Cγ subunit of PKA ("PKA-Cγ") was examined as a positive control. FIG. 14B is a picture of the immunofluorescence analysis of the cells using anti-TCRαβ antibodies at 11 days post-reprogramming. DNA was labeled with propidium iodide. FIG. 14C is a picture of each cell type stimulated with anti-CD3 antibodies and PMA for 24 hours, starting at two days post-reprogramming. Stimulated and unstimulated cells were analyzed by immunofluorescence using anti-IL-2Rβ (green) and anti-IL-2Rα (red) antibodies. Stimulation of Jurkat cells and Jurkat extract-treated 293T fibroblasts elicited IL-2-Rα synthesis. DNA (blue) was labeled with Hoechst 33342. Merged images are shown (bars, 10 μm).

FIG. 20 is a table of exemplary autoantibodies that can be targeted by the reprogrammed cells of the invention that express a TCR.

FIG. 21 is a table of exemplary antigens from pathogens that can be targeted by the reprogrammed cells of the invention that express a TCR.

DETAILED DESCRIPTION

Figure 1:
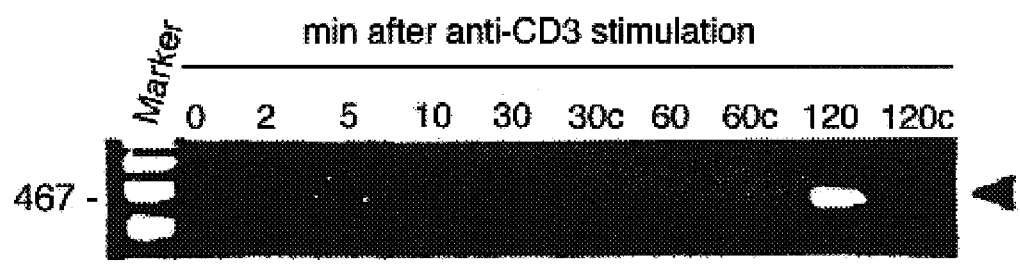
FIG. 1 is an illustration of a gel showing the amount of IL-2 mRNA synthesized by human T-cells stimulated with anti-CD3 antibodies for the indicated lengths of time. Lanes "30c," "60c," and "120c" refer to mock-stimulated T-cells.
Figure 2:
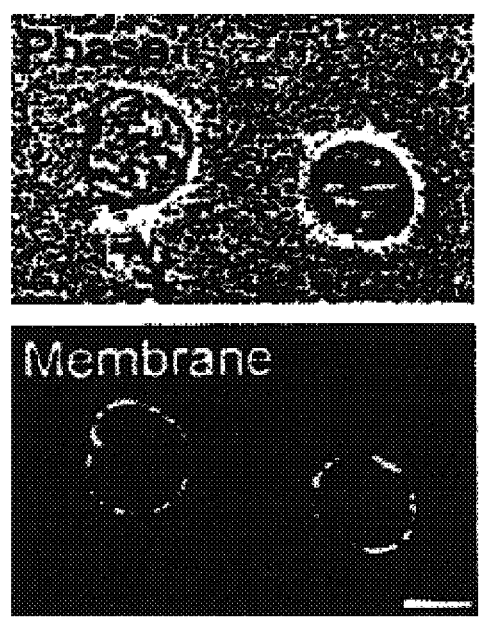
FIG. 2 is an illustration of nuclei purified from resting T-cells.

We have developed novel methods of reprogramming cells by exposing them or their genetic material to a reprogramming media (e.g., a T-cell extract). This reprogramming refers to decreasing or eliminating the expression of genes specific for the donor cell or increasing the expression of genes specific for another cell type (e.g., genes specific for T-cells). Preferred reprogramming methods involve the incubation of a nucleus, chromatin mass, or permeabilized cell with a reprogramming media containing factors expressed by T-cells (e.g., a T-cell extract), as described further below. In some embodiments, a nucleic acid encoding a T-cell receptor (TCR) specific for an antigen of interest (e.g., an antigen from a tumor cell, fat cell, autoimmune generated cell, autoantibody, or infectious pathogen) is inserted into the nucleus, chromatin mass, or permeabilized cell before, during, or after incubation in the extract. In other embodiments, the reprogrammed cells express multiple TCRs, and cells expressing the desired TCR are selected by specifically expanding the desired cells by incubating them in the presence of the antigen of interest. The antigen stimulates the proliferation of only the desired cells. The selected reprogrammed cell expresses the TCR and can be administered to a mammal (e.g., a human) to enhance the mammal's immune response against cells (e.g., tumor cells, fat cells, or autoimmune generated cells) or pathogens expressing the antigen. Thus, these reprogrammed cells are useful for the treatment or prevention of cancers, infections, obesity, and autoimmune diseases.

We have shown that incubation of nuclei from resting T-cells, B-cells, or fibroblasts in an extract from stimulated T-cells results in migration of a T-cell specific transcription factor from the extract into the nuclei. Additionally, the reprogramming of nuclei from resting T-cells, fibroblasts, endothelial (HUVEC), differentiated epithelial (HeLa), and neuronal precursor (NT2) cells induced expression of the IL-2 gene, a gene that is otherwise repressed by the nuclei. Reprogramming of resting T-cell and fibroblast nuclei also induced hyperacetylation of the IL-2 gene and intranuclear anchoring of a chromatin remodeling complex. Thus, reprogramming media such as extracts may be used to alter the expression profile of the genetic material of a donor cell such that it resembles that of the cells used to prepare the reprogramming media.

In one such reprogramming method, a nucleus from an interphase donor cell is incubated in a reprogramming media prepared from interphase cells (e.g., an interphase T-cell extract) under conditions that allow export of factors, such as transcription regulatory factors, from the nucleus and the import of factors from the reprogramming media into the nucleus. The nucleus is then inserted into a recipient cell or cytoplast, forming a reprogrammed cell. Preferably, the cells used to prepare the interphase reprogramming media are the cell type one wishes the reprogrammed cell to become (e.g., a T-cell). Due to the different factors in the nucleus of the reprogrammed cell compared to that of the donor cell, the reprogrammed cell expresses a different set of mRNA and protein molecules and thus has a different phenotype than that of the donor cell. To achieve optimum reprogramming efficiency, 2, 3, 5, or more rounds of reprogramming may be performed. The reprogrammed cells may also be cultured under conditions promoting sustained changes in cell function. For example, the cells may be cultured with additional components such as antigens, interleukins, growth factors, cytokines, or other cells. The reprogrammed cells can also be transplanted into a host animal or patient in the organ or region (e.g., the bloodstream) where they are supposed to function. Local environment cues may facilitate reprogramming.

In a related method, the nucleus from a donor interphase cell is incubated in a mitotic reprogramming media (e.g., a mitotic cell extract), a detergent and salt solution, or a protein kinase solution to promote nuclear envelope dissolution and possibly chromatin condensation, forming a chromatin mass. This nuclear envelope breakdown and chromatin condensation facilitate the release of factors from the chromatin mass. Alternatively, a chromatin mass may be isolated from a donor mitotic cell. In one embodiment of this method, the chromatin mass is inserted into a recipient cell or cytoplast of the desired cell type (e.g., a T-cell). After this nuclear transfer, a nucleus is reformed from the donor chromatin mass. Additionally, desired factors from the cytoplasm of the recipient cell or cytoplast migrate into the nucleus and bind the exogenous chromosomes, resulting in the expression of desired genes by the reprogrammed cell. To promote the sustained expression of the desired genes, 2, 3, 5, or more rounds of reprogramming may be performed, and the reprogrammed cells may also be cultured with additional components such as antigens, interleukins, growth factors, cytokines, or other cells.

In another embodiment of this method, the chromatin mass is first incubated in an interphase reprogramming media (e.g., an interphase cell extract) as described above to further promote the release of undesirable factors from the chromatin mass and the binding of desirable factors from the interphase reprogramming media to the chromatin mass. The incubation in the interphase reprogramming media also results in the formation of a nuclear membrane, encapsulating the chromatin mass and desired factors from the reprogramming media. The reformed nucleus is then inserted into a recipient cell or cytoplast of the desired cell type or of any other cell type.

As an alternative to isolating nuclei or chromatin masses from donor cells for subsequent incubation in a reprogramming media, donor cells may be gently permeabilized and incubated in the reprogramming media (e.g., a T-cell extract). Permeabilization of the plasma membrane allows factors to enter and leave the cell. The cells may either be incubated in an interphase reprogramming media to allow the nucleus to remain membrane-bounded or with a mitotic reprogramming media to allow the dissolution of the nuclear membrane and formation of a chromatin mass. After incubation in the reprogramming media, the plasma membrane may be resealed, trapping desired factors from the reprogramming media inside the cell. If desired, this reprogramming method can be repeated 1, 2, 3, 4, 5, or more times. For example, after the resealed cell is cultured for a certain length of time (e.g., after 2 days, 7 days, 14 days, 3 weeks, 4 weeks, 8 weeks, or longer) in the presence or absence of factors such as antigens, interleukins, growth factors, cytokines, or other cells to promote reprogramming, the cells are permeabilized and subjected to an additional round of reprogramming. Additional cycles of reprogramming may result in more stable and heritable epigenetic changes and in prolonged expression of the phenotype or proteins of interest from the reprogrammed cells.

This whole cell reprogramming method was utilized to reprogram permeabilized, human fibroblast cells using an extract from the lymphoblastic leukemia cell line, Jurkat-TAg (hereafter referred to as Jurkat), resulting in the remodeling of chromatin, activation of lymphoid-specific genes, and establishment of a T-cell-specific activity. For example, T-cell-specific antigens such as the CD3-T-cell receptor (TCR) complex were expressed by the reprogrammed cells, and the IL-2 receptor was assembled in response to CD3-TCR stimulation of these cells. After exposure to an NT2 neuronal precursor cell extract, permeabilized fibroblasts expressed a neurofilament protein and extended neurite-like outgrowths in culture. Fibroblasts were also reprogrammed into cells resembling embryonic stem cells.

In addition to forming T-cells that express a desired TCR, these reprogramming methods may be used to form a cell of any desired cell type. For example, the methods for reprogramming a cell that are described herein may be used to convert a cell into another cell-type that is closely related by origin or character. In particular, members of the connective-tissue family, such as fibroblasts, smooth muscle cells, osteoblasts, adipocytes, and chondrocytes, may be interconverted using these methods. Additionally, hepatocytes may be converted into insulin-producing B-cells because both of these cell types express many of the same genes. Alternatively, a cell may be converted into a desired cell type that is distantly related to the donor cell and thus shares few or no characteristics or functions with the donor cell.

Reprogrammed cells generated from these methods may be used to replace cells in a mammal in need of a particular cell type. The reprogramming methods may be used to either directly produce cells of the desired cell type or to produce undifferentiated cells which may be subsequently differentiated into the desired cell type. For example, stem cells may be differentiated in vitro by culturing them under the appropriate conditions or differentiated in vivo after administration to an appropriate region in a mammal. In particular, hormonal stimulation or co-culture has shown to induce the differentiation of myoblasts into adipocytes (Hu et al., Proc. Natl. Acad. Sci. U.S.A 92:9856-9860,1995), pancreatic cells into hepatocytes (Shen et al., Nat. Cell Biol. 2:879-887, 2000), keratocytes into myoblasts (Funderburgh et al., J. Biol. Chem. 276:44173-44178, 2001) and endothelial cells into cardiomyocytes (Condorelli et al., Proc. Natl. Acad. Sci. U.S.A. 98:10733-10738, 2001). To optimize phenotypic and functional changes, reprogrammed cells can be transplanted into the organ (e.g., a heart) or region where they are intended to function in an animal model or in human patients shortly after reprogramming (e.g., after 1, 2, 3, 5, 7, or more days). Reprogrammed cells implanted in an organ may be reprogrammed to a greater extent than cells grown in culture prior to transplantation. Cells implanted in an animal organ may be removed from the organ and transplanted into a recipient mammal such as a human, or the animal organ may be transplanted into the recipient.

To increase the length of time the cell, nuclei, or chromatin mass may be reprogrammed in vitro prior to administration to a mammal for the treatment of disease, the donor cell may be preferably modified by the transient transfection of a plasmid containing an oncogene flanked by loxP sites for the Cre recombinase and containing a nucleic acid encoding the Cre recombinase under the control of an inducible promoter (Cheng et al., Nucleic Acids Res. 28(24):E108, 2000). The insertion of this plasmid results in the controlled immortalization of the cell. After the cell is reprogrammed into the desired cell-type and is ready to be administered to a mammal, the loxP-oncogene-loxP cassette may be removed from the plasmid by the induction of the Cre recombinase which causes site-specific recombination and loss of the cassette from the plasmid. Due to the removal of the cassette containing the oncogene, the cell is no longer immortalized and may be administered to the mammal without causing the formation of a cancerous tumor.

Reprogrammed cells that express a TCR that is reactive with an antigen from a tumor cell can be administered to a mammal (e.g., a human) using any standard method (e.g., intravenous administration) to treat, stabilize, or prevent cancer. Preferably, the cancerous cells in the mammal express the antigen that the TCR binds. Because the TCR is specific for cancerous cells, the administered reprogrammed cells destroy cancerous cells without harming the healthy cells in the mammal. Preferably, the reprogrammed cells also stimulate B-cells to produce antibodies against the cancerous cells, leading to a further reduction in the number and/or activity of cancerous cells.

To treat, stabilize, or prevent infections, a reprogrammed cell that expresses a TCR reactive with an antigen from a pathogen can be administered to the mammal. The reprogrammed cells preferably destroy infected cells or infectious pathogens without harming healthy cells and preferably induce B-cells to produce antibodies that bind infected cells or pathogens.

Reprogrammed cells that expresses a TCR reactive with an antigen from a fat cell (e.g., an adipocyte) can be used to reduce the number of fat cells or to prevent an increase in the number of fat cells in a mammal. Single or multiple administrations of these reprogrammed cells allow a mammal to reach a desired weight and to maintain that weight. Reprogrammed cells that expresses a TCR reactive with an antigen from an autoimmune generated cell or autoantibody can be used to treat or prevent autoimmune disease.

Other examples of medical applications for reprogrammed cells include the administration of neuronal cells to an appropriate area in the human nervous system to treat, prevent, or stabilize a neurological disease such as Alzheimer's disease, Parkinson's disease, Huntington's disease, or ALS; or a spinal cord injury. In particular, degenerating or injured neuronal cells may be replaced by the corresponding cells from a mammal. This transplantation method may also be used to treat, prevent, or stabilize autoimmune diseases including, but not limited to, insulin dependent diabetes mellitus, rheumatoid arthritis, pemphigus vulgaris, multiple sclerosis, and myasthenia gravis. In these procedures, the cells that are attacked by the recipient's own immune system may be replaced by transplanted cells. In particular, insulin-producing cells may be administered to the mammal for the treatment or prevention of diabetes, or oligodendroglial precursor cells may be transplanted for the treatment or prevention of multiple sclerosis. For the treatment or prevention of endocrine conditions, reprogrammed cells that produce a hormone, such as a growth factor, thyroid hormone, thyroid-stimulating hormone, parathyroid hormone, steroid, serotonin, epinephrine, or norepinephrine may be administered to a mammal. Additionally, reprogrammed epithelial cells may be administered to repair damage to the lining of a body cavity or organ, such as a lung, gut, exocrine gland, or urogenital tract. It is also contemplated that reprogrammed cells may be administered to a mammal to treat damage or deficiency of cells in an organ such as the bladder, brain, esophagus, fallopian tube, heart, intestines, gallbladder, kidney, liver, lung, ovaries, pancreas, prostate, spinal cord, spleen, stomach, testes, thymus, thyroid, trachea, ureter, urethra, or uterus.

Reprogrammed cells may also be combined with a matrix to form a tissue or organ in vitro or in vivo that may be used to repair or replace a tissue or organ in a recipient mammal. For example, reprogrammed cells may be cultured in vitro in the presence of a matrix to produce a tissue or organ of the urogenital system, such as the bladder, clitoris, corpus cavermosum, kidney, testis, ureter, uretal valve, or urethra, which may then be transplanted into a mammal (Atala, Curr. Opin. Urol. 9(6):517-526, 1999). In another transplant application, synthetic blood vessels are formed in vitro by culturing reprogrammed cells in the presence of an appropriate matrix, and then the vessels are transplanted into a mammal for the treatment or prevention of a cardiovascular or circulatory condition. For the generation of donor cartilage or bone tissue, reprogrammed cells such as chondrocytes or osteocytes are cultured in vitro in the presence of a matrix under conditions that allow the formation of cartilage or bone, and then the matrix containing the donor tissue is administered to a mammal. Alternatively, a mixture of the cells and a matrix may be administered to a mammal for the formation of the desired tissue in vivo. Preferably, the cells are attached to the surface of the matrix or encapsulated by the matrix. Examples of matrices that may be used for the formation of donor tissues or organs include collagen matrices, carbon fibers, polyvinyl alcohol sponges, acrylateamide sponges, fibrin-thrombin gels, hyaluronic acid-based polymers, and synthetic polymer matrices containing polyanhydride, polyorthoester, polyglycolic acid, or a combination thereof (see, for example, U.S. Pat. Nos. 4,846,835; 4,642,120; 5,786,217; and 5,041,138).

These methods are described further below. It is noted that any of the methods described below can be performed with reprogramming media other than cell extracts. For example, a reprogramming media can be formed by adding one or more naturally-occurring or recombinant factors (e.g., nucleic acids or proteins such as T-cell receptors or other signaling surface molecules, DNA methyltransferases, hi stone deacetylases, histones, nuclear lamins, transcription factors, activators, repressors, growth factors, hormones, or cytokines) to a solution, such as a buffer. Preferably, one or more of the factors are specific for the cell type one wishes the donor cell to become.

EXAMPLE 1

One-Step In Vitro Reprogramming Method

In the following method for reprogramming cells, nuclei are isolated from interphase cells and incubated in an interphase reprogramming media (e.g., an interphase cell extract) under conditions that allow the addition of factors from the reprogramming media to the nuclei or the removal of factors from the nuclei. Preferably, the nuclei remain membrane-bounded during this incubation. The reprogrammed nuclei are then isolated from the reprogramming media and inserted into recipient cells or cytoplasts.

Isolation of Nuclei

Preferably, cells from the subject who will receive the reprogrammed cells are used as the source of donor nuclei. However, cells from other members of the same species or members of a different species or genus may be used. As many as several million nuclei may be isolated from synchronized or unsynchronized cell populations in culture. The cell populations may be synchronized naturally or chemically. Preferably, at least 40, 60, 80, 90, or 100% of the cells in a population are arrested in interphase, such as in one or more of the following phases of the cell cycle: $G_o$, $G_1$, S, or $G_2$, using standard procedures.

To accomplish this, cells may be incubated, for example, in low serum, such as 5%, 2%, or 0% serum, for 1, 2, 3, or more days to increase the percentage of cells in $G_o$ phase. To synchronize cells in $G_1$, the cells may be grown to confluence as attached cells and then incubated in 0.5-1 μg/ml nocodazole (Sigma Chemicals, St. Louis, Mo.) for 17-20 hours, as described previously (see, for example, Collas et al., 1999 and references therein). The flasks containing the attached cells are shaken vigorously by repeatedly tapping the flasks with one hand, resulting in the detachment of mitotic cells and $G_1$ phase doublets. The $G_1$ phase doublets are pairs of elongated cells at the end of the division process that are still connected by a thin bridge. Detached $G_1$ phase doublets may be isolated from the media based on this characteristic doublet structure. The $G_1$ phase doublets may remain attached or may divide into two separate cells after isolation.

To increase the percentage of cells in S phase, the cells may be cultured in the presence of aphidicolin which inhibits DNA polymerase-α and thus inhibits DNA synthesis and arrests cells in S phase. Alternatively, cells may be incubated in the presence of excess thymidine. The resulting high intracellular concentration of thymidine relative to that of other nucleotides also inhibits DNA polymerase.

Cells may be synchronized in $G_2$ by incubating the cells in the presence of aphidicolin to arrest them in S phase and then washing the cells three times by repeated centrifugation and resuspension in phosphate buffered saline (PBS), as described herein. The cells are then incubated for a length of time sufficient for cells to enter $G_2$ phase. For example, cells with a doubling time of approximately 24 hours, may be incubated for between 6 and 12 hours to allow them to enter $G_2$ phase. For cells with shorter or longer doubling times, the incubation time may be adjusted accordingly.

The synchronized or unsynchronized cells are harvested in PBS using standard procedures, and several washing steps are performed to transfer the cells from their original media into a hypotonic buffer (10 mM Hepes, pH 7.5, 2 mM $MgCl_2$, 25 mM KCl, 1 mM DTT, 10 μM aprotinin, 10 μM leupeptin, 10 μM pepstatin A, 10 μM soybean trypsin inhibitor, and 100 μM PMSF). For example, the cells may be washed with 50 ml of PBS and pelleted by centrifugation at 500×g for 10 minutes at 4° C. The PBS supernatant is decanted, and the pelleted cells are resuspended in 50 ml of PBS and centrifuged, as described above. After this centrifugation, the pelleted cells are resuspended in 20-50 volumes of ice-cold hypotonic buffer and centrifuged at 500×g for 10 minutes at 4° C. The supernatant is again discarded and approximately 20 volumes of hypotonic buffer are added to the cell pellet. The cells are carefully resuspended in this buffer and incubated on ice for at least one hour, resulting in the gradual swelling of the cells.

To allow isolation of the nuclei from the cells, the cells are lysed using standard procedures. For example, 2-5 ml of the cell suspension may be transferred to a glass homogenizer and Dounce homogenized using an initial 10-20 strokes of a tight-fitting pestle. Alternatively, the cell suspension is homogenized using a motorized mixer (e.g., Ultraturrax). If desired, cell lysis may be monitored using phase contrast microscopy at 40-fold magnification. During this homogenization, the nuclei should remain intact and most or preferably all of the originally attached cytoplasmic components such as vesicles, organelles, and proteins should be released from the nuclei. If necessary, 1-20 μg/ml of the cytoskeletal inhibitors, cytochalasin B or cytochalasin D, may be added to the aforementioned hypotonic buffer to facilitate this process. Homogenization is continued as long as necessary to lyse the cells and release cytoplasmic components from the nuclei. For some cell types, as many as 100, 150, or more strokes may be required. The lysate is then transferred into a 15 ml conical tube on ice, and the cell lysis procedure is repeated with the remainder of the suspension of swollen cells. Sucrose from a 2 M stock solution made in hypotonic buffer is added to the cell lysate, resulting in a final concentration of 250 mM sucrose. This solution is mixed by inversion, and the nuclei are pelleted by centrifugation at 400×g in a swing out rotor for 10 to 40 minutes at 4° C. The supernatant is then discarded, and the pelleted nuclei are resuspended in 10-20 volumes of nuclear buffer (10 mM Hepes, pH 7.5, 2 mM $MgCl_2$, 250 mM sucrose, 25 mM KCl, 1 mM DTT, 10 μM aprotinin, 10 μM leupeptin, 10 μM pepstatin A, 10 μM soybean trypsin inhibitor, and 100 μM PMSF). The nuclei are sedimented and resuspended in 1-2 volumes of nuclear buffer, as described above. The freshly isolated nuclei may either be used immediately for in vitro reprogramming and nuclear transfer into recipient cells or cytoplasts as described below or stored for later use. For storage, the nuclei are diluted in nuclear buffer to a concentration of approximately $10^6$/ml. Glycerol (2.4 volumes of 100% glycerol) is added and mixed well by gentle pipetting. The suspension is aliquoted into 100-500 μl volumes in 1.5-ml tubes on ice, immediately frozen in a methanol-dry ice bath, and stored at −80° C. Prior to use, aliquots of the nuclei are thawed on ice or at room temperature. One volume of ice cold nuclear buffer is added, and the solution is centrifuged at 1,000×g for 15 minutes in a swing out rotor. The pelleted nuclei are resuspended in 100-500 μl nuclear buffer and centrifuged as described above. The pelleted nuclei are then resuspended in a minimal volume of nuclear buffer and stored on ice until use.

Preparation of the Reprogramming Extract

Interphase cultured cells as harvested using standard methods and washed by centrifugation at 500×g for 10 minutes in a 10 ml conical tube at 4° C. Preferably, the cells are of the desired cell type that one wishes the recipient cell or cytoplast to become. The supernatant is discarded, and the cell pellet is resuspended in a total volume of 50 ml of cold PBS. The cells are centrifuged at 500×g for 10 minutes at 4° C. This washing step is repeated, and the cell pellet is resuspended in approximately 20 volumes of ice-cold interphase cell lysis buffer (20 mM Hepes, pH 8.2, 5 mM $MgCl_2$, 1 mM DTT, 10 μM aprotinin, 10 μM leupeptin, 10 μM pepstatin A, 10 μM soybean trypsin inhibitor, 100 μM PMSF, and preferably 20 μg/ml cytochalasin B). The cells are sedimented by centrifugation at 800×g for 10 minutes at 4° C. The supernatant is discarded, and the cell pellet is carefully resuspended in no more than one volume of interphase cell lysis buffer. The cells are incubated on ice for one hour to allow swelling of the cells. The cells are lysed by either sonication using a tip sonicator or Dounce homogenization using a glass mortar and pestle. Cell lysis is performed until at least 90% of the cells and nuclei are lysed, which may be assessed using phase contrast microscopy. The sonication time required to lyse at least 90% of the cells and nuclei may vary depending on the type of cell used to prepare the extract.

The cell lysate is placed in a 1.5-ml centrifuge tube and centrifuged at 10,000 to 15,000×g for 15 minutes at 4° C. using a table top centrifuge. The tubes are removed from the centrifuge and immediately placed on ice. The supernatant is carefully collected using a 200 μl pipette tip, and the supernatant from several tubes is pooled and placed on ice. This supernatant is the "interphase cytoplasmic" or "IS15" extract. This cell extract may be aliquoted into 20 μl volumes of extract per tube on ice and immediately flash-frozen on liquid nitrogen and stored at −80° C. until use. Alternatively, the cell extract is placed in an ultracentrifuge tube on ice (e.g., fitted for an SW55 Ti rotor; Beckman). If necessary, the tube is overlayed with mineral oil to the top. The extract is centrifuged at 200,000×g for three hours at 4° C. to sediment membrane vesicles contained in the IS15 extract. At the end of centrifugation, the oil is discarded. The supernatant is carefully collected, pooled if necessary, and placed in a cold 1.5 ml tube on ice. This supernatant is referred to as "IS200" or "interphase cytosolic" extract. The extract is aliquoted and frozen as described for the IS15 extract.

If desired, the extract can be enriched with additional nuclear factors. For example, nuclei can be purified from cells of the cell type from which the reprogramming extract is derived and lysed by sonication as described above. The nuclear factors are extracted by a 10-60 minute incubation in nuclear buffer containing NaCl or KCl at a concentration of 0.15-800 mM under agitation. The lysate is centrifuged to sediment unextractable components. The supernatant containing the extracted factors of interest is dialyzed to eliminate the NaCl or KCl. The dialyzed nuclear extract is aliquoted and stored frozen. This nuclear extract is added at various concentrations to the whole cell extract described above prior to adding the nuclei for reprogramming.

As an alternative to a cell extract, a reprogramming media can also be formed by adding one or more naturally-occurring or recombinant factors (e.g., nucleic acids or proteins such as T-cell receptors or other signaling surface molecules, DNA methyltransferases, histone deacetylases, histones, nuclear lamins, transcription factors, activators, repressors, growth factors, hormones, or cytokines) to a solution, such as a buffer. Preferably, one or more of the factors are specific for the cell type one wishes the donor cell to become.

Reprogramming of Nuclei in the Extract

Figure 3A:
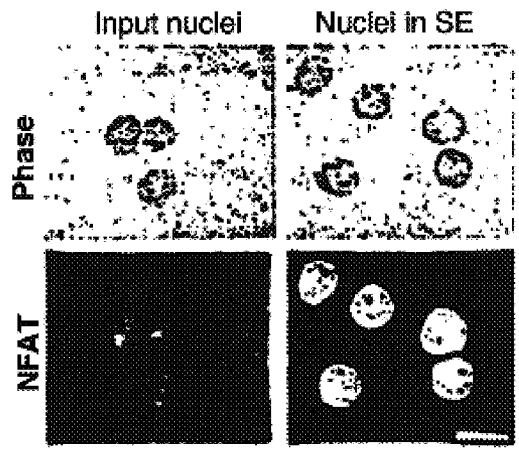
FIG. 3A is the immunofluorescence analysis of nuclear uptake and binding of the T-cell specific transcription factor NFAT in cell-free reprogramming extracts. For this assay, nuclei purified from resting T-cells ("Input" nuclei) were incubated with reprogramming extract from stimulated T-cells for 30 minutes.
Figure 6A:
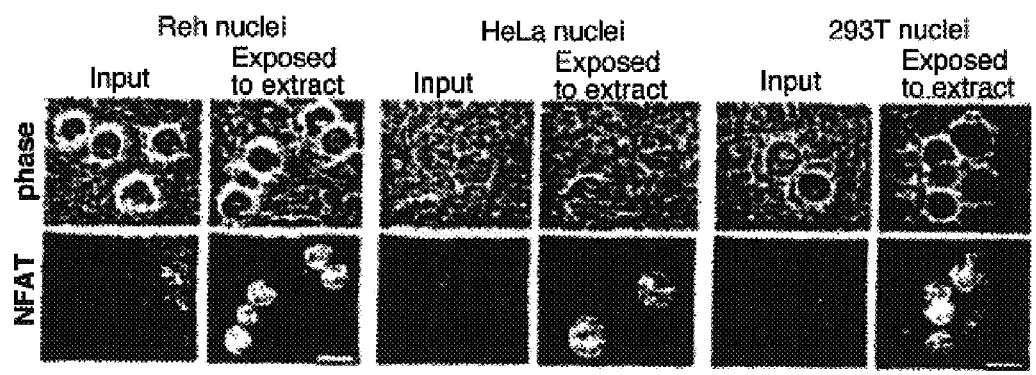
FIG. 6A is the immunofluorescence analysis -showing nuclear uptake and binding of the T-cell specific transcription factor NFAT by nuclei from the B-cell line Reh, 293T fibroblasts, or HeLa cells that have been incubated with the stimulated T-cell extract, as described for FIG. 3A.

Either freshly isolated or thawed purified nuclei are resuspended in the reprogramming media described in the previous section at a concentration of 4,000-5,000 nuclei/μl. An ATP generating system (1 mM ATP, 10 mM creatine phosphate, 25 μg/ml creatine kinase) and 100 μM GTP are added to the interphase extract to promote active uptake of nuclear components by the exogenous nuclei. The reaction is incubated at 30° C. for up to two hours. Uptake of specific nuclear components may be monitored by immunofluorescence analysis of the nuclei, as shown in FIGS. 3A and 6A.

Purification of Reprogrammed Nuclei Out of the Extract

The reprogrammed nuclei are centrifuged at 1,000×g for 10-30 minutes through a 1 M sucrose cushion prepared in nuclear buffer at 4° C. The nuclei are washed by resuspending them in 500 μl cold nuclear buffer and centrifuging at 1,000×g for 10 minutes at 4° C. The nuclei are resuspended in nuclear buffer and held on ice until use for nuclear transfer into the cytoplasm of recipient cells or cytoplasts.

Enucleation of Recipient Cells

Preferably, part or all of the DNA in the recipient cell is removed or inactivated. This destruction or removal of the DNA in the recipient cell prevents the genetic material of the cell from contributing to the characteristics and function of the reprogrammed cell. One method for destroying the nucleus of the cell is exposure to ultraviolet light (Gurdon, in *Methods in Cell Biology, Xenopus Laevis:—Practical Uses in cell and Molecular Biology*, Kay and Peng, eds., Academic Press, California, volume 36:pages 299-309, 1991). Alternatively, the nucleus may be surgically removed by any standard technique (see, for example, McGrath and Solter, Science 220:1300-1319, 1983). In one possible method, a needle is placed into the cell, and the nucleus is aspirated into the inner space of the needle. The needle may then be removed from the cell without rupturing the plasma membrane (U.S. Pat. Nos. 4,994,384 and 5,057,420).

Introduction of Reprogrammed Nuclei into Recipient Cells or Cytoplasts

The nuclei are introduced into recipient cells or cytoplasts of either the desired cell type or of any other cell type using standard methods, such as microinjection or electrofusion (see, for example, U.S. Pat. Nos. 4,997,384 and 5,945,577).

The reconstituted cells are placed back in culture and allowed to recover, divide, and differentiate according to the reprogrammed pathway. Gene expression by the reprogrammed cells may be monitored using standard Northern analysis to measure expression of mRNA molecules, preferably mRNA molecules that are specific for the donor cell, recipient cell, or the desired cell type (Ausubel et al., supra). Expression of specific mRNA molecules may also be detected using standard reverse-transcription polymerase chain reaction (RT-PCR) assays with primers designed to specifically bind an mRNA molecule of interest. Alternatively, the expression of multiple cell specific mRNA molecules may be monitored using standard DNA chip technology with cDNA arrays (Marrack et al., Current Opinion in Immunology 12, 206-209, 2000; Harkin, Oncologist. 5:501-507, 2000; Pelizzari et al., Nucleic Acids Res. 2;28(22):4577-4581, 2000; Marx, Science 289(5485):1670-1672, 2000). The cells may be analyzed for a reduction in expression of genes specific for the cell type of the donor cell, recipient cell, or recipient cytoplast. Additionally, cells may be assayed for an increase in expression of genes specific for the desired cell type. Examples of mRNA molecules that are indicative of reprogramming to generate a stem cell include H-19, SSEA-3, SSEA-4, TRA-1-60, TRA-1-81, GCTM-2, Oct-4, Genesis, GCNF, GDF-3, and TDGF-1. Neural cell specific mRNA molecules include, but are not limited to, NGF, NF-H, NeuN, NSE, and CD11b. For analyzing the conversion to an adipocyte cell fate, expression of mRNA molecules such as leptin, PPARλ1, PPARλ2, SREBP1C, IR, and TNFα may be monitored. IGF-1 and IR are indicative of insulin producing cells. Additionally, the cells may be analyzed for expression of particular proteins using standard Western or immunofluorescence analysis (Ausubel et al., supra).

Examples of other characteristics of the reprogrammed cell that may be analyzed to determine whether it has been converted into the desired cell type include the size of the cell, cell morphology, ability to grow as an adherent cell, ability to grow as an attached cell, volume of cytoplasm, and location of a centrosome. The functions of the reprogrammed cells may also be tested, such as the ability of red blood cells to transport $O_2$ and $CO_2$, the ability of B-cells to make antibodies, and the ability of neutrophiles to phagocytose and destroy invading bacteria. Additionally, the production of lipids by adipocytes may be determined using standard microscopy to visualize lipid droplets in the cells.

EXAMPLE 2

Two-Step In Vitro Reprogramming Method

In another method for reprogramming cells, nuclei are isolated from interphase cells and incubated in a mitotic extract, a detergent and salt solution, or a protein kinase solution to induce nuclear envelope breakdown and the formation of chromatin masses. This incubation causes the release of factors from the chromatin masses. Alternatively, chromatin masses may be isolated from mitotic cells. Preferably, the chromatin masses are then incubated in an interphase reprogramming extract to promote the formation of nuclear membranes and the addition of desired factors from the extract to the resulting nuclei. The reprogrammed nuclei are then isolated from the extract and inserted into recipient cells or cytoplasts of the desired cell type or of any other cell type.

Alternatively, the chromatin masses may be directly inserted into recipient cells or cytoplasts without first being induced to reform nuclei. For this embodiment, recipient cells or cytoplasts of the desired cell type are used so that desired factors from the cytoplasm of the recipient cells or cytoplasts may bind the exogenous chromosomes from the donor chromatin masses and further promote the expression of desired mRNA and protein molecules.

Preparation of Mitotic Cell Extract

A mitotic cytoplasmic (MS15) or mitotic cytosolic (MS200) extract may be prepared as described above for interphase IS15 or IS200 extract, except that mitotic cells are used instead of interphase cells and that 10 mM EDTA is added to the cell lysis buffer. If desired, the extract can be enriched with additional nuclear factors as described in Example 1. For the isolation of mitotic cells, somatic cells are synchronized in mitosis by incubating them in 0.5-1 µg/ml nocodazole for 17-20 hours, and the mitotic cells are detached by vigorous shaking, as described above. The detached $G_1$ phase doublets may be discarded, or they may be allowed to remain with the mitotic cells which constitute the majority (over 80%) of the detached cells. The harvested detached cells are centrifuged at 500×g for 10 minutes in a 10 ml conical tube at 4° C.

Chromosome Condensation Reaction in Mitotic Extract for Removal of Endogenous Nuclear Components An aliquot of MS15 or MS200 extract is thawed on ice. An ATP-generating system (0.6 µl) and GTP are added to 20 µl of extract and mixed by vortexing, resulting in final concentrations of 1 mM ATP, 10 mM creatine phosphate, 25 µg/ml creatine kinase, and 100 µM GTP.

Nuclei are isolated from donor cells as described above. The nuclei suspension is added to the extract at a concentration of 1 µl nuclei per 10 µl of extract, mixed well by pipetting, and incubated in a 30, 33, 35, 37, or 39° C. water bath. The tube containing the mixture is tapped gently at regular intervals to prevent chromosomes from clumping at the bottom of the tube. Nuclear envelope breakdown and chromosome condensation is monitored at regular intervals, such as every 15 minutes, under a microscope. When the nuclear envelope has broken down and chromosomes have started to condense, the procedure for recovery of chromatin masses from the extract is started.

Formation of Decondensed Chromatin Masses by Exposure of Nuclei to Mitotic Extract and Anti-NuMA Antibodies Alternatively, chromatin masses that are not condensed or only partially condensed may be formed by performing the above procedure after pre-loading the isolated nuclei with an antibody to the nuclear matrix protein NuMA (Steen et al., J. Cell Biol. 149, 531-536, 2000). This procedure allows the removal of nuclear components from chromatin by the dissolution of the nuclear membrane surrounding the donor nuclei; however, the condensation step is inhibited by addition of the anti-NuMA antibody. Preventing chromosome condensation may reduce the risk of chromosome breakage or loss while the chromosomes are incubated in the mitotic extract.

For this procedure, purified cell nuclei (2,000 nuclei/µl) are permeabilized in 500 µl nuclear buffer containing 0.75 µg/ml lysolecithin for 15 minutes at room temperature. Excess lysolecithin is quenched by adding 1 ml of 3% BSA made in nuclear buffer and incubating for 5 minutes on ice. The nuclei are then sedimented and washed once in nuclear buffer. The nuclei are resuspended at, 2,000 nuclei/µl in 100 µl nuclear buffer containing an anti-NuMA antibody (1:40 dilution; Transduction Laboratories). After a one hour incubation on ice with gentle agitation, the nuclei are sedimented at 500×g through 1 M sucrose for 20 minutes. The nuclei are then resuspended in nuclear buffer and added to a mitotic extract containing an ATP regenerating system, as described in the previous section. Preferably, the anti-NuMA antibody may be added to the extract to further prevent chromosome condensation.

Formation of Decondensed Chromatin Masses by Exposure of Nuclei to a Detergent or Protein Kinase Chromatin masses that are not condensed or only partially condensed may also be formed by exposure to a detergent or protein kinase. A detergent may be used to solubilize nuclear components that are either unbound or loosely bound to the chromosomes in the nucleus, resulting in the removal of the nuclear envelope. For this procedure, purified cell nuclei (2,000-10,000 nuclei/µl) are incubated in nuclear buffer supplemented with a detergent, such as 0.1% to 0.5% Triton X-100 or NP-40. To facilitate removal of the nuclear envelope, additional salt, such as NaCl, may be added to the buffer at a concentration of approximately 0.1, 0.15, 0.25, 0.5, 0.75, or 1 M. After a 30-60 minute incubation on ice with gentle shaking, the nuclei are sedimented by centrifugation at 1,000×g in a swing-out rotor for 10-30 minutes, depending on the total volume. The pelleted nuclei are resuspended in 0.5 to 1 ml nuclear buffer and sedimented as described above. This washing procedure is repeated twice to ensure complete removal of the detergent and extra salt.

Alternatively, the nuclear envelope may be removed using recombinant or naturally-occurring protein kinases, alone or in combination. Preferably, the protein kinases are purified using standard procedures or obtained in purified form from commercial sources. These kinases may phosphorylate components of the nuclear membrane, nuclear matrix, or chromatin, resulting in removal of the nuclear envelope (see, for example, Collas and Courvalin, Trends Cell Biol. 10: 5-8, 2000). Preferred kinases include cyclin-dependent kinase 1 (CDK1), protein kinase C (PKC), protein kinase A (PKA), MAP kinase, and calcium/calmodulin-dependent kinase (CamKII). For this method, approximately 20,000 purified nuclei are incubated in 20 µl of phosphorylation buffer at room temperature in a 1.5 ml centrifuge tube. A preferred phosphorylation buffer for CDK1 (Upstate Biotechnology) contains 200 mM NaCl, 50 mM Tris-HCl (pH 7.2-7.6), 10 mM $MgSO_4$, 80 mM β-glycerophosphate, 5 mM EGTA, 100 µM ATP, and 1 mM DTT. For PKC, a preferred buffer contains 200 mM NaCl, 50 mM Tris-HCl (pH 7.2-7.6), 10 mM $MgSO_4$, 100 µM $CaCl_2$, 40 µg/ml phosphatidylserine, 20 µM diacylglycerol, 100 µM ATP, and 1 mM DTT. If both PKC and CDK1 are used simultaneously, the CDK1 phosphorylation buffer supplemented with 40 µg/ml phosphatidylserine and 20 µM diacylglycerol is used. A preferred phosphorylation buffer for PKA includes 200 mM NaCl, 10 mM MgSO4, 10 mM Tris, pH 7.0, 1 mM EDTA, and 100 µM ATP. For MAP kinase, the PKA phosphorylation buffer supplemented with 10 mM $CaCl_2$, and 1 mM DTT may be used. For CamKII, either PKA buffer supplemented with 1 mM DTT or a Cam Kinase assay kit from Upstate Biotechnology (Venema et al. J. Biol. Chem 272: 28187-90, 1997) is used.

The phosphorylation reaction is initiated by adding a protein kinase to a final amount of 25-100 ng. The reaction is incubated at room temperature for up to one hour. Nuclear envelope breakdown may be monitored by microscopy during this incubation, such as at 15 minute intervals. After nuclear envelope breakdown, nuclei are washed three times, as described above for the removal of the detergent solution.

Recovery of Chromatin Masses from the Extract Detergent and Salt Solution, or Protein Kinase Solution The extract or solution containing the condensed, partially condensed, or not condensed chromatin masses is placed under an equal volume of 1 M sucrose solution made in nuclear buffer. The chromatin masses are sedimented by centrifugation at 1,000×g for 10-30 minutes depending on the sample volume in a swing out rotor at 4° C. The supernatant is discarded and the pelleted chromatin masses are carefully resuspended by pipetting in 0.1-1.0 ml nuclear buffer and centrifuged at 1,000×g for 10-30 minutes. The supernatant is discarded, and the pelleted chromatin masses are resuspended in nuclear buffer and stored on ice until use.

Isolation of Chromatin Masses from Mitotic Cells

As an alternative to generating chromatin masses by exposure of nuclei to a mitotic extract, a detergent and salt solution, or a protein kinase solution, chromatin masses may be obtained by lysis of cells synchronized in mitosis and centrifugation of the cell lysate as described herein.

Preparation of Membrane Vesicles for Nuclear Reassembly In Vitro

The pellet generated from the 200,000×g centrifugation during the preparation of the MS2000 mitotic extract is used as a source of mitotic membrane vesicles. This pellet is resuspended in membrane wash buffer (250 mM sucrose, 50 mM KCl, 2.5 mM $MgCl_2$, 50 mM Hepes, pH 7.5, 1 mM DTT, 1 mM ATP, 10 µM aprotinin, 10 µM leupeptin, 10 µM pepstatin A, 10 µM soybean trypsin inhibitor, and 100 µM PMSF), centrifuged at 100,000×g for 30 minutes, aliquoted, frozen in liquid nitrogen, and stored at −80° C.

Nuclear Reassembly Assay

If desired, nuclei may be reassembled from condensed, partially condensed, or decondensed chromatin masses as described below. The reformation of the nuclear membrane around the chromosomes may encapsulate factors from the extract used for reassembly allowing them to be transferred as part of the reformed nucleus into the recipient cell or cytoplast. The chromatin masses are recovered by sedimentation through a 1 M sucrose cushion and are resuspended in interphase extract at a concentration of 4,000-5,000 chromatin masses/µl. Preferably, this interphase extract is formed from cells of the cell type that is desired, as described above. The extract is supplemented with membrane vesicles prepared as described above to provide membranes which are required for nuclear envelope assembly. The membranes are added at a concentration of 1 µl thawed membranes per 10 µt extract and mixed by vortexing. An ATP generating system (2 mM ATP, 20 mM creatine phosphate, 50 µg/ml creatine kinase) and 100 µM GTP are added to the interphase extract to promote chromatin decondensation, binding of nuclear membrane vesicles to chromatin, and vesicle fusion to form an intact nuclear membrane. The reaction is incubated at 30° C. for up to two hours, and nuclear reassembly is monitored by phase contract microscopy.

Purification of Reprogrammed Nuclei Out of the Extract

Reprogrammed nuclei are centrifuged at 1,000×g for 10-30 minutes through a 1 M sucrose cushion prepared in nuclear buffer at 4° C. The nuclei are washed by resuspending them in 500 µl cold nuclear buffer and sedimentation at 1,000×g for 10 minutes at 4° C. Then, the nuclei are resuspended in nuclear buffer and held on ice until use for nuclear transfer into the cytoplasm of recipient cells or cytoplasts.

Introduction of Reprogrammed Nuclei or Chromatin Masses into Recipient Cells or Cytoplasts The chromatin masses or nuclei formed from the chromatin masses are inserted into recipient cells or cytoplasts using standard methods, and gene expression is monitored, as described above.

EXAMPLE 3

Reprogramming of Permeabilized Cells without Nuclear Transfer

Cells may also be reprogrammed without requiring the isolation of nuclei or chromatin masses from the cells. In this method, interphase or mitotic cells are permeabilized and then incubated in an interphase or mitotic reprogramming extract under conditions that allow the exchange of factors between the extract and the cells. If an interphase extract is used, the nuclei in the cells remain membrane-bounded; if a mitotic extract is used, nuclear envelope breakdown and chromatin condensation may occur. After the nuclei are reprogrammed by incubation in this extract, the plasma membrane is preferably resealed, forming an intact reprogrammed cell that contains desired factors from the extract. If desired, the extract can be enriched with additional nuclear factors as described in Example 1.

Permeabilization of Cells

Cells that may be reprogrammed using this procedure include unsynchronized cells and cells synchronized in $G_o$, $G_1$, S, $G_2$, or M phase or a combination of these phases. The cells are permeabilized using any standard procedure, such as permeabilization with digitonin or Streptolysin O. Briefly, cells are harvested using standard procedures and washed with PBS. For digitonin permeabilization, cells are resuspended in culture medium containing digitonin at a concentration of approximately 0.001-0.1% and incubated on ice for 10 minutes. For permeabilization with Streptolysin O, cells are incubated in Streptolysin O solution (see, for example, Maghazachi et al., 1997 and references therein) for 15-30 minutes at room temperature. After either incubation, the cells are washed by centrifugation at 400×g for 10 minutes. This washing step is repeated twice by resuspension and sedimentation in PBS. Cells are kept in PBS at room temperature until use. Alternatively, the cells can be permeabilized while placed on coverslips as described in Example 6 to minimize the handling of the cells and to eliminate the centrifugation of the cells, thereby maximizing the viability of the cells. Preferably, the cells are immediately added to the interphase or mitotic extract for reprogramming, as described below.

Reprogramming of Cells in Extract

An interphase or mitotic extract is prepared as described above, preferably using cells of the cell type that one desires the permeabilized cells to become. The permeabilized cells are suspended in the reprogramming extract at a concentration of approximately 100-1,000 cells/µl. The ATP generating system and GTP are added to the extract as described above, and the reaction is incubated at 30-37° C. for up to two hours to promote translocation of factors from the extract into the cell and active nuclear uptake or chromosome-binding of factors. The reprogrammed cells are centrifuged at 800×g, washed by resuspension, and centrifugation at 400×g in PBS. The cells are resuspended in culture medium containing 20-30% fetal calf serum (FCS) and incubated for 1-3 hours at 37° C. in a regular cell culture incubator to allow resealing of the cell membrane. The cells are then washed in regular warm culture medium (10% FCS) and cultured further using standard culturing conditions.

EXAMPLE 4

Reprogramming Using an Activated T-Cell Extract

This reprogramming study using an activated T-cell extract is based on functional differences between resting and activated T-cells. Antigen-mediated activation of resting peripheral blood T-cells by stimulation of the T-cell antigen receptor-CD3 (TCR-CD3) complex and the CD28 co-stimulatory receptor induces chromatin remodeling and activation of numerous genes. One such gene is the T-cell-specific growth factor interleukin-2 (IL-2) gene. IL-2 regulation involves the stimulation-dependent activators NFAT, NFκB, AP-1, the constitutive transcription factor Oct-1, and the mitogen-activated protein kinase, Erk.

Cell extracts from activated human T-cells were used to induce nuclear localization of transcription factors in unactivated human T-cells, B-cells, human fibroblasts, and HeLa cells. Additionally, this incubation promoted DNA-binding of the chromatin remodeling SWI/SNF complex, hyperacetylation of the IL-2 gene and promoter, and expression of IL-2 mRNA in unactivated T-cells. Expression of IL-2 was also induced in primary vascular endothelial cells, epithelial cells, and neuronal precursor cells.

To demonstrate that activation of intact T-cells induces expression of IL-2, human T-cells were purified from peripheral blood, cultured overnight, and stimulated with anti-CD3 antibodies (clone SpvT3d obtained from A. M. Rasmussen, Norwegian Radium Hospital, Montebello, Norway). In particular, T-cells were purified from peripheral blood from healthy donors (Skalhegg et al., Science 263:84-87, 1994). Cells were cultured for 20 hours and incubated on ice for 15 minutes at $5$-$10 \times 10^7$ cells/ml in RPMI 1640 (Gibco BRL). The TCR-CD3 complex was stimulated with 5 µg/ml anti-CD3 antibodies, and the cells were incubated on ice for 30 minutes. Cells were spun at 400×g at 4° C. for 7 minutes, washed, and resuspended to $5 \times 10^7$ cells/ml in ice-cold RPMI1600. An anti-mouse Fab fragment (10 µg/ml) was added as a cross-linker, and the cells were incubated at 37° C. (t=0 min post-stimulation). At the indicated time points, cells were diluted with ice-cold PBS, snap-frozen in liquid nitrogen, thawed, and washed in PBS. Total RNA was isolated, and RT-PCR was performed using IL-2-specific primers. As illustrated in FIG. 1, IL-2 mRNA is expressed in activated T-cells but not expressed in mock-treated T-cells ("30c," "60c," and "120c" denote mock-treated cells).

To determine whether extract from activated T-cells can increase nuclear localization of transcription factors in other cells, T-cells were activated by incubation in the presence of an anti-CD3 antibody (Skalhegg, et al., Science 263:84-87, 1994), and then the cells were washed to remove the unbound antibody. Stimulated T-cell extracts (SE) were prepared 5-10 minutes after anti-CD3 stimulation (i.e., 2 hours before onset of transcription of the IL-2 gene). This timing for preparation of the extract allowed unequivocal detection of IL-2 transcription in the reprogrammed nuclei because the stimulated extract did not contain any endogenous IL-2 mRNA. To halt all reactions, cells were snap-frozen in liquid nitrogen at 5-10 minutes post-stimulation, thawed, washed in ice-cold PBS and in lysis buffer (10 mM Hepes, pH 8.2, 50 mM NaCl, 5 mM $MgCl_2$, 1 mM DTT, and protease inhibitors), and sedimented. The pellets were resuspended in two volumes of lysis buffer.

A stimulated T-cell extract was prepared by lysing these T-cells, centrifuging them at 15,000×g, isolating the supernatant, and adding an ATP-generating system to the supernatant. In particular, cells were disrupted with a tip sonicator until over 90% of the cells and nuclei were lysed. The lysate was cleared at 15,000×g for 15 minutes at 4° C. The supernatant was used fresh or aliquoted, frozen in liquid nitrogen, and stored at −80° C. This simple method does not require dialysis, and therefore the extract remains concentrated (~25 mg/ml protein), and the procedure minimizes risks of proteolysis. Extract from unstimulated T-cells (USE) were prepared from mock ($H_2O$)-stimulated T-cells. A reprogramming reaction consisted of 20 µl or multiples thereof of stimulated extract or unstimulated extract containing $10^5$ nuclei and an ATP generating system (1 mM ATP, 10 mM creatine phosphate, 25 µg/ml creatine kinase, and 100 µM GTP).

Figure 8A:
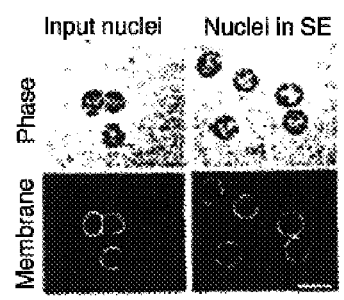
FIGS. 8A-8D are pictures and graphs that illustrate nuclear uptake and chromatin binding of transcriptional activators of the IL-2 gene in stimulated T-cell extract.

To generate donor nuclei, resting peripheral blood T-cells were washed and resuspended in 20 volumes of ice-cold hypotonic nuclear buffer (10 mM Hepes, pH 7.5, 2 mM $MgCl_2$, 25 mM KCl, 1 mM DTT, and protease inhibitors). Nuclei were isolated by careful Dounce-homogenization, sedimented at 400×g and washed in nuclear buffer (hypotonic nuclear buffer/250 mM sucrose). HUVEC, HeLa, and NT2 nuclei were isolated similarly. Nuclear integrity prior to, and after, incubation in the extract was monitored by phase contrast microscopy and by nuclear membrane labeling with 10 µg/ml of the lipophilic dye, $DiOC_6$ (FIG. 8A). Nuclei purified from resting T-cells, from the B-cell line Reh, 293T fibroblasts, or HeLa cells were incubated in this extract for 30 minutes at a concentration of approximately 5,000 nuclei per µl of extract and at 30° C. unless otherwise indicated. Then, the nuclei were purified by sedimentation for 10 minutes through a 1 M sucrose cushion. Alternatively, RNA was extracted from the reaction mix for RT-PCR. As demonstrated by immunofluorescence analysis, the T-cell specific transcription factor NFAT was imported into the nuclei exposed to the stimulated extract (FIGS. 3A and 6A).

Figure 3B:
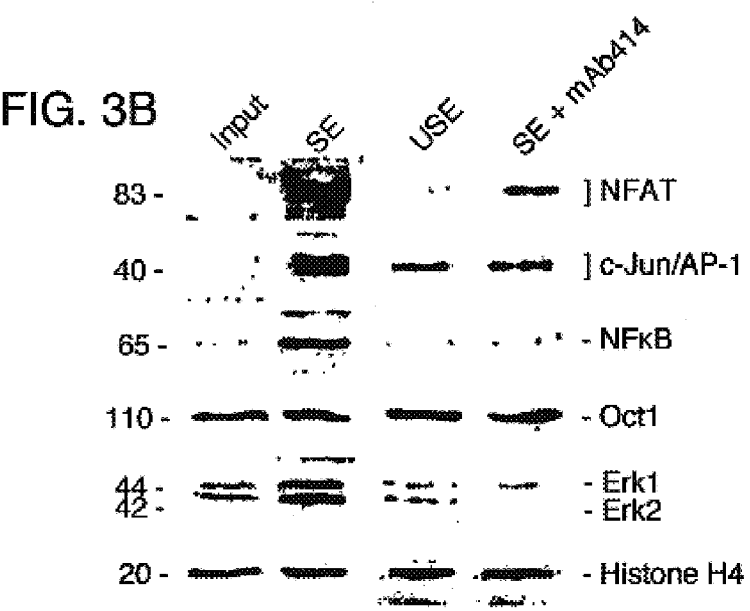
FIG. 3B in an illustration of an immunoblot showing the nuclear uptake of NFAT, c-Jun/AP1, NFκB, Oct1, and MAP kinase (Erk1 and Erk2). Input nuclei ("Input") and nuclei incubated in either a stimulated extract ("SE"), a control extract prepared from unstimulated T-cells (denoted "USE" for unstimulated extract), or a stimulated extract containing a monoclonal antibody against nucleoporins ("SE+mAb414") were analyzed.
Figure 8B:
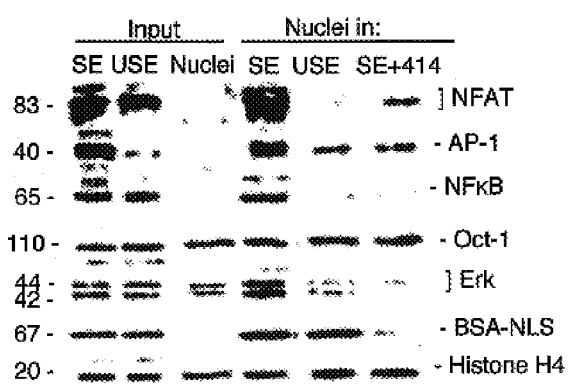

The ability of other transcription factors from the extract to migrate into the nuclei of T-cells, B-cells, fibroblasts, and HeLa cells was also determined. For this assay, input donor nuclei ("Input") from unstimulated T-cells were incubated in either stimulated extract ("SE"), control extract prepared from unstimulated T-cells (denoted "USE" for unstimulated extract), or stimulated extract containing a monoclonal antibody against nucleoporins which sterically blocks nuclear import ("SE+mAb414"). The nuclei were then purified from the extract by centrifugation and resuspension. As expected for a whole cell extract, NFAT, AP-1, or NFκB, Oct-1 and Erk (1 and 2) were detected on Western blots of input stimulated extract prior to incubation of the nuclei (FIG. 8B). Virtually no AP-1 was seen in input unstimulated extract likely because the complex is not assembled in unstimulated T-cells, and no NFAT, AP-1, NFκB and little Erk were detected in input nuclei (FIG. 8B). As illustrated in FIGS. 3B and 8B, T-cell nuclei incubated in the stimulated extract had increased levels of NFAT, c-Jun/AP 1, NFκB, and MAP kinase (Erk1 and Erk2), as measured using standard Western blot analysis with an anti-histone H4 antibody as a loading control and with antibodies to each factor (e.g., the anti-Erk antibody obtained from Dr J. Kubiak, CNRS, Paris, France). The AP-1 transcription complex was also assembled in the nuclei (FIG. 8B), presumably as a result of Jun-Fos association. And Erk was imported into nuclei exposed to stimulated extract (FIG. 8B). Nuclear import of all factors was verified by immunofluorescence analysis. Nuclear uptake of these factors in resting T-cell nuclei occurred actively through nuclear pore complexes because import was inhibited by substituting ATP or GTP with ATPγS, AMP-PNP, or GTPγS in the extract, or by functional inhibition of nuclear pores with mAb414, an antibody against several nucleoporins obtained from M. Rout, Rockefeller University, New York (FIG. 8B, SE+414) (Davies and Blobel, Cell 45:699-709, 1986). The ubiquitous transcription factor Oct-1 was detected in similar amounts in input nuclei and nuclei exposed to stimulated extract or unstimulated extract (FIG. 8B, Oct-1). Incubation of the nuclei in the unstimulated extract had negligible effect on the level of these transcription factors.

Additionally, NFAT, c-Jun/AP1, and NFκB levels were increased in nuclei from Reh B-cells, 293T fibroblasts, and HeLa cells after incubation in the stimulated T-cell extract (FIG. 6A). For example, immunological analyses of purified 293T fibroblast nuclei showed that the stimulated T-cell extract, but not the control unstimulated T-cell extract, supported nuclear uptake of NFAT, NFκB, and assembly of the AP-1 transcription complex (FIGS. 1A and 11B). Notably, the unstimulated extract supported nuclear import of BSA conjugated to nuclear localization signals in resting T-cell nuclei and fibroblast nuclei to the same extent as the stimulated extract (FIG. 8B BSA-NLS, and 11B), demonstrating specificity of import and assembly of transcriptional activators of the IL-2 gene for the stimulated extract.

Figure 3C:
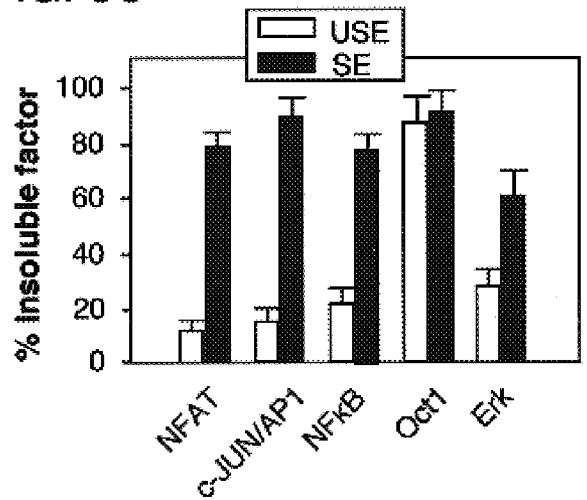
FIG. 3C is a bar graph showing the percentage of transcription factors bound to DNA, reported as the mean±the standard deviation.

For T-cell nuclei exposed to either the stimulated or unstimulated extract, DNA-binding by these transcription factors was assessed using a standard nuclear retention assay. This assay involves extraction of nuclei with 0.1% Triton X-100 to dissolve the nuclear membrane and sedimentation at 15,000×g or extraction with 0.5% Triton X-100 for one hour and sedimentation at 10,000×g for 10 minutes (Zhao et al., Cell 95:625-636, 1998). Soluble chromatin fractions were prepared from purified nuclei by micrococcal nuclease digestion and EDTA extraction (O'Neill and Turner, Methods Enzymol. 274:189-197, 1996). Nuclear matrices, defined as Triton X-100, DNAse, and RNAse extraction-resistant structures were isolated as described previously (Steen et al., J. Cell Biol. 149:531-536, 2000). Immunoblot analysis was performed on the pellet, which contains transcription factors that are bound to DNA, and the supernatant, which contains the unbound transcription factors. In particular, insoluble material was dissolved in SDS, and proteins in the soluble fraction were precipitated and dissolved in SDS. Equal protein amounts of both fractions (30 µg) were analyzed by immunoblotting. The percentage of DNA-bound transcription factors were determined by densitometric analysis of duplicate blots. The data is reported as the mean±the standard deviation (FIG. 3C).

Figure 8C:
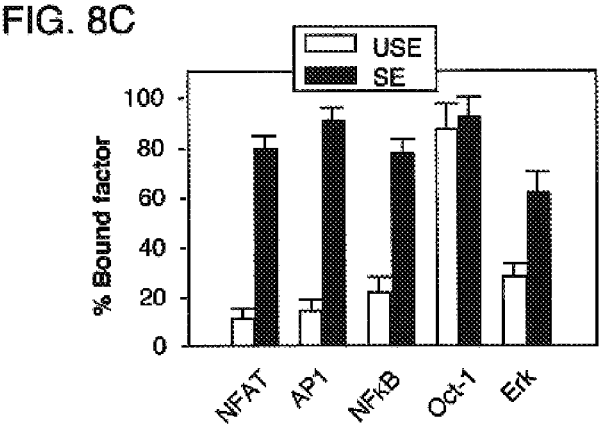
Figure 8D:
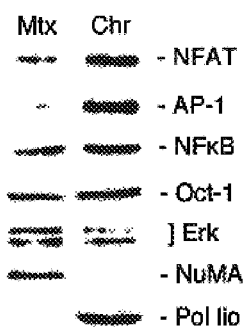

The results of this nuclear retention assay also support the increased nuclear import and DNA-binding of NFAT, c-Jun/AP1, NFκB, and MAP kinase transcription factors in reprogrammed T-cell nuclei. For example, an increase of up to 8.5-fold in intranuclear bound NFAT, AP-1, and NFκB was detected in nuclei exposed to the stimulated extract compared to nuclei exposed to the unstimulated extract (FIG. 8C). Bound Oct-1 was detected in nuclei exposed to unstimulated extract or stimulated extract (FIG. 8C) consistent with its DNA-binding ability in T-cell and non-T-cell nuclei. A two-fold increase in bound Erk also occurred in nuclei exposed to stimulated extract (FIG. 8C). Immunoblotting of soluble chromatin and nuclear matrix fractions prepared from nuclei exposed to stimulated extract indicated that NFAT, AP-1, NFκB, and Oct-1 were primarily bound to chromatin, whereas most of insoluble Erk was associated with the matrix (FIG. 8D).

Figure 4A:
FIG. 4A is an illustration of an immunoblot showing the DNA-binding of the chromatin remodeling SWI/SNF complex in T-cell nuclei exposed to a buffer control, an unstimulated extract, or a stimulated extract for 30 minutes and sedimented through sucrose.
Figure 4B:
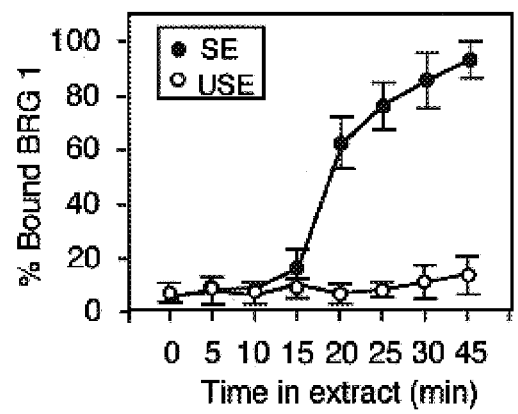
FIG. 4B is a graph showing the percentage of DNA bound and unbound SWI/SNF complex in nuclei incubated in extract for the indicated lengths of time, as assessed using a nuclear retention assay. The SWI/SNF complex was visualized on Western blots using anti-BRG1 antibodies.
Figure 4C:
FIG. 4C is an illustration of an immunoblot showing the nuclear retention of the SWI/SNF complex in stimulated T-cells in vivo. For this assay, T-cells were stimulated with anti-CD3 antibodies for 30 minutes, and the soluble and DNA bound fractions of the SWI/SNF complex were assessed as described for FIG. 4A.
Figure 4D:
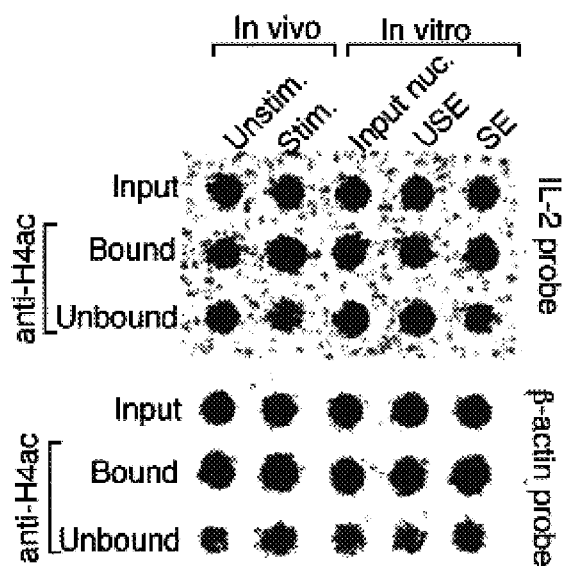
FIG. 4D is an illustration of an immunoblot showing hyperacetylation of the IL-2 gene of T-cell nuclei in vivo and in vitro. An MNAse-soluble chromatin fraction was prepared from resting and anti-CD3-stimulated T-cells. The immunoblot shows the binding of an IL-2 probe and a control β-actin probe to DNA from the immunoprecipitate of the chromatin fraction with an anti-acetylated histone H4 (H4ac) probe ("bound") and the binding to DNA in the supernatant ("unbound") fractions.
Figure 9A:
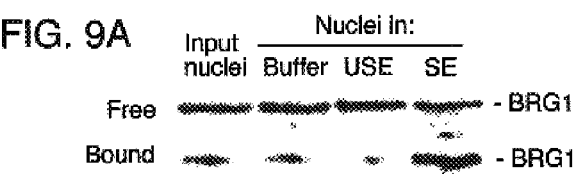
FIGS. 9A-9E illustrate chromatin remodeling in resting T-cell nuclei exposed to a stimulated T-cell extract.
Figure 9B:
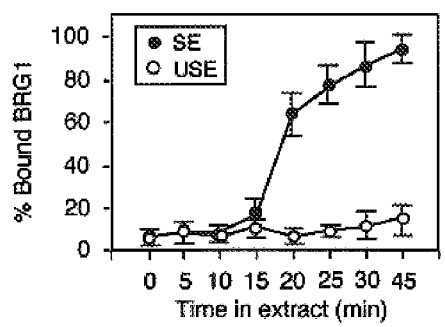
Figure 9C:
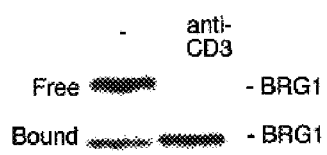

For demonstration of the effect of exposing T-cell nuclei to the stimulated extract on the DNA-binding of the chromatin remodeling SWI/SNF complex, resting T-cell nuclei were incubated in cell lysis buffer, the unstimulated extract, or the stimulated extract, each containing an ATP-generating system, for 30 minutes and sedimented through sucrose. The percentage of DNA-bound and unbound human SWI/SNF after various incubation times was assessed using the above nuclear retention assay with anti-BRG1 antibodies to visualize the SWI/SNF complex (FIGS. 4B, 4C, 9A) (Collas et al., J. Cell Biol. 147:1167-1180, 1999). In particular, BRG1 was immunoprecipitated from micrococcal nuclease-soluble chromatin pre-cleared with rabbit IgGs using a 1:40 dilution of anti-BRG1 antibodies for 2.5 hours. The immune complex was precipitated using protein A-sepharose beads, washed in immunoprecipitation buffer, and dissolved in SDS sample buffer (Collas et al., J. Cell Biol. 147:1167-1180, 1999). Exposure of the nuclei to the stimulated extract increased the amount of DNA-bound SWI/SNF, suggesting that reprogramming of the nuclei was occurring. For example, densitometric analysis of blots using antibodies to BRG 1, a marker of the SWI/SNF complex (Zhao et al., Cell 95:625-636, 1998), showed that over 80% of SWI/SNF was in an insoluble (bound) form in nuclei exposed to the stimulated extract, while SWI/SNF remained mostly soluble in input nuclei or nuclei exposed to unstimulated extract (FIGS. 9A and 9B). Intranuclear binding of SWI/SNF took place within 30 minutes (FIG. 9B). The physiological relevance of SWI/SNF binding in vitro was illustrated by intranuclear anchoring of SWI/SNF within 30 minutes of anti-CD3 stimulation of human peripheral blood T-cells (FIG. 9C).

Figure 9D:
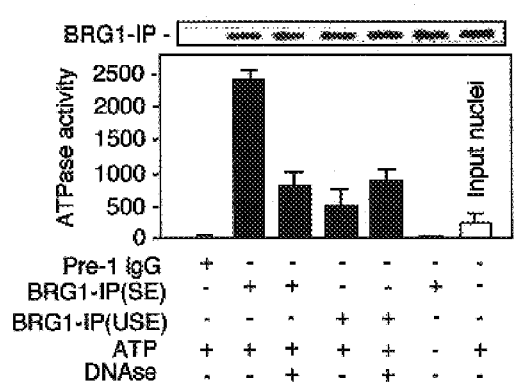

The potential activity of SWI/SNF was evaluated by measuring its relative ATPase activity in input nuclei and nuclei exposed to stimulated extract or unstimulated extract. Similar amounts of SWI/SNF were immunoprecipitated from purified nuclear lysates using anti-BRG1 antibodies (FIG. 9D). Hydrolysis of 1 nM exogenous ATP by each immune precipitate ("BRG1-IP") was determined in a luciferin-luciferase assay. Control precipitates using pre-immune IgGs were used as a reference (FIG. 9D, Pre-I IgG). ATPase activity was expressed as relative light units in the assay after subtraction of the pre-immune IgG reference value of 2,700. BRG1-IP purified from input nuclei or nuclei exposed to unstimulated extract displayed no or little ATPase activity. However, BRG1-IP isolated from nuclei exposed to stimulated extract showed an 8-fold increase in ATPase activity compared to input nuclei (FIG. 9D). Furthermore, stimulated extract-induced ATPase activity was reduced close to basal levels when BRG 1-IP was treated with DNAse I prior to the assay (FIG. 9D). These results indicate that intranuclear bound SWI/SNF complex exhibits DNA-dependent ATPase activity specific for the stimulated T-cell extract.

To measure hyperacetylation of the IL-2 gene of T-cell nuclei in vivo and in vitro, micrococcal nuclease was used to digest the chromatin from resting T-cells, anti-CD3-stimulated T-cells, T-cell nuclei exposed to an unstimulated extract, and T-cell nuclei exposed to a stimulated extract, forming soluble chromatin fragments. Acetylated histone H4 ("H4ac") was immunoprecipitated from the soluble chromatin fraction, and DNA was isolated from immune precipitate ("bound") and supernatant ("unbound") fractions. The DNA was dot-blotted on duplicate Hybon N filters and hybridized to either a fluoresceinated IL-2 probe to the IL-2 coding region or a carp β-actin probe. Hybridization was detected using alkaline phosphatase-conjugated anti-fluorescein antibodies. Hyperacetylation of the IL-2 gene, but not the control β-actin gene, was observed in nuclei exposed to the stimulated extract, further suggesting that the nuclei were being reprogrammed to express genes usually repressed by the nuclei.

Acetylation of histone H4 in the IL-2 promoter after T-cell stimulation in culture and in quiescent T-cell nuclei exposed to unstimulated extract or stimulated extract was also measured by chromatin immunoprecipitation analysis, using anti-H4 and H4ac antibodies from Serotec. Hyperacetylation of the IL-2 promoter was examined by chromatin immunoprecipitation from mock ($H_2O$) and anti-CD3-stimulated T-cells after solubilization with 0.1 U micrococcal nuclease per µg DNA to from mono- and di-nucleosomes. An anti-pan-acetylated histone H4 (acH4) antibody was used to detect acetylated histones (O'Neill and Turner, Methods Enzymol. 274: 189-197, 1996). DNA was isolated by phenol-chloroform extraction from input, antibody-bound, and unbound chromatin fractions, and IL-2 was identified by dot blot analysis using an IL-2 probe. The IL-2 promoter probe was synthesized by random prime labeling with fluoresceinated nucleotides (Gene Images CDP-Star, Amersham), using as the template a cloned 430 base pair insert corresponding to the 360 base pairs of the promoter/enhancer regions proximal to the start site and the first 70 base pairs of the IL-2 coding region (exon I). Primers used were 5'-GCTATTCACATGT-TCAGTGTAG-3' (SEQ ID NO: 1) to hybridize the promoter region and 5'-GACAGGAGTTGCATCCTGTACA-3' (SEQ ID NO: 2) to hybridize to exon I. The β-actin probe was synthesized as described above using a cloned SalI-NcoI 1.3-kb insert of β-actin intron I as a template (Collas et al., J. Cell Sci. 112:1045-1054, 1999b). Hybridization was detected by chemiluminescence using alkaline phosphatase-conjugated anti-fluorescein antibodies (Collas et al., J. Cell Sci. 112:1045-1054, 1999b).

Figure 9E:
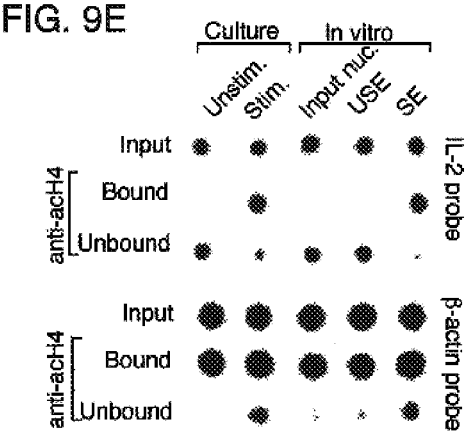

In unstimulated T-cells, the IL-2 promoter was entirely detected in the anti-acH4 unbound fraction, suggesting hypoacetylation or absence of H4 acetylation of the IL-2 promoter (FIG. 9E, "Culture"). T-cell stimulation, however, elicited hyperactetylation of the IL-2 promoter, as demonstrated by its high enrichment in the anti-acH4-bound fraction (FIG. 9E, "Culture"). Significantly, the IL-2 promoter was also highly enriched in H4 hyperacetylated chromatin after incubation of nuclei in stimulated extract, but not in unstimulated extract (FIG. 9E, "In vitro"). These results are in agreement with reports showing that chromatin configuration changes occurring in the IL-2 promoter upon T-cell activation are confined to the minimal enhancer region from −300 base pairs to the transcription start codon (Ward et al., Nucleic. Acids. Res. 26:2923-2934, 1998; Rao et al., J. Immunol. 167:4494-4503, 2001). Altogether, these data provide strong evidence for chromatin remodeling of the IL-2 proximal promoter region in resting T-cell nuclei exposed to the stimulated T-cell extract.

Figure 5A:
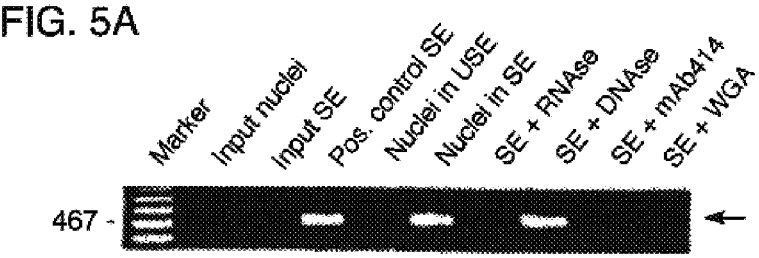
FIG. 5A is a gel showing the synthesis of IL-2 mRNA in cell-free extracts. Resting T-cell nuclei ("Input nuclei") were incubated for 30 minutes at 30° C. in an unstimulated extract or a stimulated extract. As controls, nuclei were incubated in a stimulated extract containing either 100 µg/ml RNAse A, 100 µg/ml DNAse I, mAb414 antibodies, or the lectin WGA.
Figure 7:
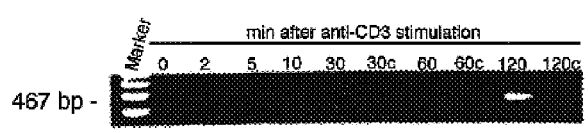
FIG. 7 is a picture of a gel showing RT-PCR analysis of IL-2 mRNA synthesis in human peripheral blood T-cells stimulated with anti-CD3 antibodies. At indicated time points, cells were lysed, and total RNA was isolated for RT-PCR analysis using IL-2-specific primers. Mock ($H_2O$)-stimulated cells were analyzed at 30, 60, and 120 minute time points ("30c," "60c," "120c")
Figure 10A:
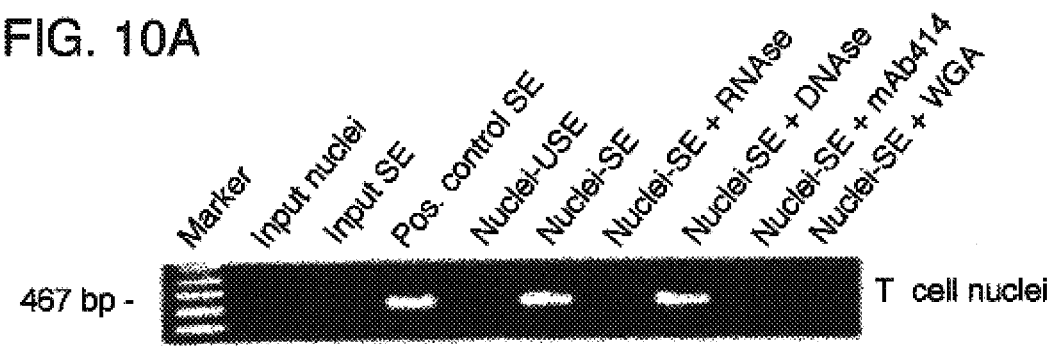
FIGS. 10A-10D are gels showing the transcription of IL-2 mRNA by T-cell and non-T-cell nuclei in cell-free extracts.

To demonstrate the ability of the stimulated extract to induce expression of IL-2, resting T-cell nuclei were incubated for 30 minutes at 30° C. in unstimulated extract or stimulated extract. As controls, nuclei were incubated in stimulated extract containing either 100 µg/ml RNAse A, 100 µg/ml DNAse I, mAb414 antibodies, or the lectin WGA. After 30 minutes at 30° C., nuclei were lysed in the extracts by sonication and 3 µl extract aliquots were removed for RT-PCR analysis using IL-2-specific primers. In particular, total RNA was isolated using the Qiagen RNeasy kit, and 15 ng RNA was used as the template for RT-PCR using the Promega Access RT-PCR System. A 467-bp IL-2 cDNA was amplified using the IL-2-specific primers 5'-ATGTACAGGATG-CAACTCCTGTCTT-3' (SEQ ID NO: 3) and 5'-GTTAGT-GTTGAGATGATGCTTTGAC-3' (SEQ ID NO:4). PCR conditions were 30 cycles of denaturation at 94° C. for one minute, annealing at 60° C. for two minutes, and extension at 72° C. for three minutes. Input stimulated extract and a control stimulated extract containing 1.2 µg total RNA isolated from IL-2-producing T-cells were also analyzed (FIGS. 5A and 10A). These results indicate that IL-2 expression was induced by incubation of T-cell nuclei in the stimulated extract but not by incubation in any of the control extracts. The PCR product of the expected size (467 base pairs) was absent from input nuclei and input stimulated extract (as expected from FIG. 7), nuclei exposed to unstimulated extract (Nuclei-USE), and nuclei exposed to stimulated extract followed by treatment with 100 µg/ml RNAse A, but not 100 µg/ml DNAse I, prior to RT-PCR. Thus, detection of IL-2 mRNA was the result of IL-2 transcription and not of RNA contamination in input nuclei or in the extract. IL-2 transcription required active nuclear import because IL-2 transcription was abolished when nuclear pore function was blocked in the stimulated extract with the mAb414 antibody or 0.5 mg/ml wheat germ agglutinin (FIG. 10A).

Figure 5B:
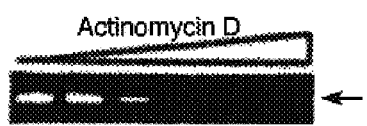
FIG. 5B is a gel showing that IL-2 mRNA production in vitro is dependent on PolII transcription. Nuclei were exposed for 30 minutes to a stimulated extract containing increasing concentrations of the RNA PolII inhibitor actinomycin D (0, 5, 10, 50, 100 and 500 nM), and IL-2 mRNA synthesis was analyzed by reverse transcription-polymerase chain reaction (RT-PCR).
Figure 5C:
FIG. 5C is an illustration of a gel showing that IL-2 mRNA production was induced in nuclei exposed to a T-cell extract treated with anti-CD3 antibodies but not induced by exposure to extracts treated with anti-CD3 antibodies from the B-cell line Reh, human 293T fibroblasts, or HeLa cells. The arrows in the illustration point to the 467 base pair IL-2 RT-PCR product.
Figure 10B:
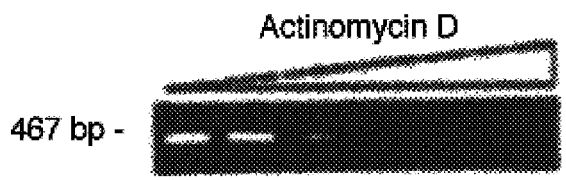

As illustrated in FIGS. 5B and 10B, this in vitro IL-2 mRNA production is dependent on PolII transcription. For this assay, nuclei were exposed for 30 minutes to stimulated extract containing increasing concentrations of the RNA PolII inhibitor actinomycin D (0, 5, 10, 50, 100 and 500 nM), and IL-2 mRNA synthesis was analyzed by RT-PCR. As a control, extracts from anti-CD3 stimulated B-cells, fibroblasts, and HeLa cells, which do not express IL-2, were tested for their ability to induce IL-2 expression in nuclei from resting T-cells. As expected, these extract failed to induce IL-2 expression. Arrows in FIGS. 5A-5C point to the 458 base pair IL-2 RT-PCR product.

Figure 10C:
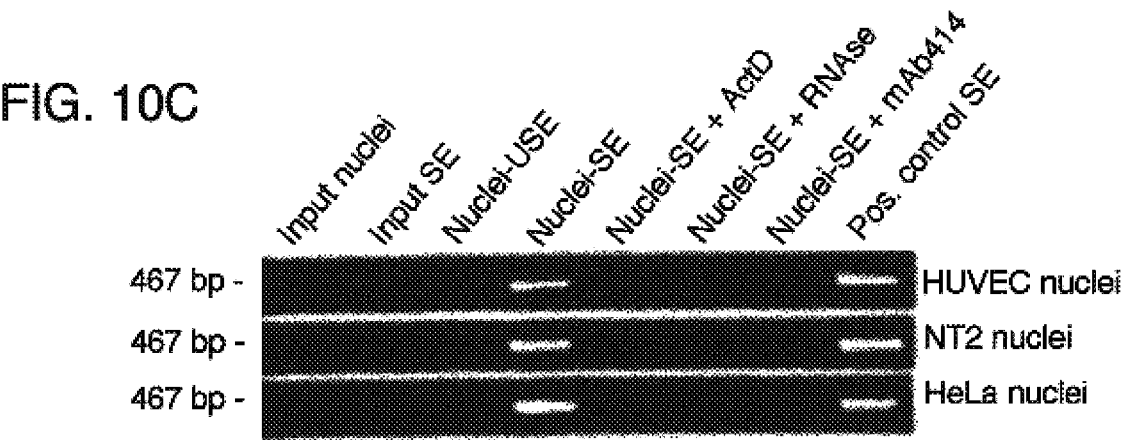
Figure 10D:
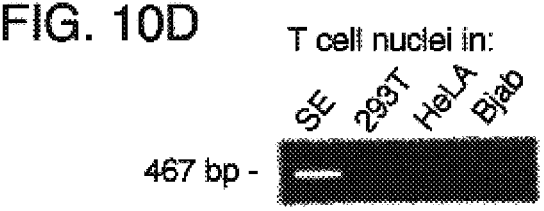

As a more stringent indicator of nuclear reprogramming, activation of the IL-2 gene was monitored in nuclei purified from primary human umbilical vein endothelial cells (HU-VEC), NT2 neuronal precursors, and HeLa cells after a two hour incubation in the stimulated extract. RT-PCR analysis indicated that the stimulated extract activated the IL-2 gene in the nuclei of all of these cell types; in contrast, the unstimulated extract was ineffective at inducing IL-2 transcription (FIG. 10C). IL-2 activation was dependent on RNA Pol II activity and nuclear import, based on its elimination by 50 nM actinomycin D and mAb414, respectively (FIG. 10C). Lastly, the specificity of IL-2 induction for the stimulated extract was demonstrated by IL-2 remaining repressed in resting T-cell nuclei exposed to control extracts from 293T fibroblasts, HeLa endothelial cells, or Bjab B-cells that had been treated with anti-CD3 and cross-linking antibodies to mimic T-cell stimulation (FIG. 10D).

In summary, these results demonstrate that nuclear reprogramming, as evidenced by transcriptional activation of a silent gene, can be induced in purified intact nuclei. Expression of the IL-2 gene was coincident with physiological nuclear uptake and assembly of transcriptional regulatory proteins. It is noteworthy that NFAT, NFκB, and AP-1 are transcription factors that reflect a proliferative response rather than a differentiation response per se. Remodeling of chromatin was demonstrated by intranuclear anchoring and DNA-dependent ATP hydrolysis activity of the SWI/SNF complex. The SWI/SNF complex uses energy of ATP hydrolysis to alter nucleosomal conformation. Notably, the stimulated extract elicited an 8-fold enhancement of ATPase activity over that of input resting T-cell nuclei, from equivalent amounts of immunoprecipitated BRG1. Thus, increased ATPase activity is the result of activation of SWI/SNF rather than a consequence of higher amounts of precipitated BRG1 in nuclei exposed to stimulated extract. Histone H4 hyperacetylation of the IL-2 proximal promoter region, which involves a complex targeting acetyltransferases to their site of action, further indicates active chromatin remodeling. While not meant to limit the invention to any particular mechanism, H4 acetylation in the IL-2 promoter may stimulate binding of transcriptional activators that would otherwise be excluded from repressed chromatin, or transcription factor binding may promote alterations in chromatin structure. The results described herein indicate nuclear reprogramming can take place in intact nuclei in vitro. The results also demonstrate that the process involves the active intranuclear assembly of protein complexes that remodel chromatin as well as the binding of transcriptional regulators.

EXAMPLE 5

Reprogramming of Fibroblasts Using an Activated T-Cell Extract

As demonstrated in Example 4, a stimulated T-cell extract increased nuclear localization of T-cell specific transcription factors in 293T fibroblasts. The ability of fibroblasts to be reprogrammed into T-cells is characterized further below.

For this study, T-cells were purified from peripheral blood from healthy donors, as described in Example 4 (Skalhegg et al., Science 263:84-87, 1994). To prepare reprogramming extracts from stimulated T-cells, cells were frozen in liquid nitrogen at 5-10 minutes post-stimulation, thawed, washed in ice-cold lysis buffer (Collas et al., J. Cell Bio. 147:1167-1180, 1999), and sedimented at 400×g. The pellets were resuspended in two volumes of lysis buffer. Cells and nuclei were disrupted with a tip sonicator, and the lysate was cleared by centrifugation at 15,000×g for 15 minutes at 4° C. The supernatant was used immediately or was frozen in liquid nitrogen and stored at −80° C. Unstimulated T-cell extracts were prepared from mock ($H_2O$)-stimulated T-cells.

Nuclear reprogramming reactions consisted of 20 μl or multiples thereof of stimulated T-cell extract or unstimulated T-cell extract containing 100,000 nuclei and an ATP generating system (1 mM ATP, 10 mM creatine phosphate, 25 μg/ml creatine kinase, and 100 μM GTP). Reactions were incubated at 30° C. for 30 minutes unless indicated otherwise. At the end of incubation, nuclei were purified by sedimentation through 1 M sucrose. Alternatively, total RNA was extracted from the reaction mix for RT-PCR.

The active uptake of transcription factors in fibroblast nuclei exposed to the stimulated T-cell extract was further demonstrated by the ability of a monoclonal antibody that reacts with nucleoporins and inhibits nuclear pore function (obtained from M. Rout, Rockefeller University, New York, N.Y., USA) to reduce nuclear import of these factors (FIG. 11B, mAb414). Oct-1 was detected in 293T input nuclei and nuclei exposed to stimulated T-cell extract or control unstimulated T-cell extract (FIG. 11B), consistent with its DNA-binding property in several cell types. Immunoblotting of chromatin and nuclear matrices of 293T nuclei treated with the stimulated T-cell extract indicated that NFAT, AP-1, NFκB, and Oct-1 were primarily bound to chromatin (FIG. 11C). Altogether, these data demonstrate physiological uptake of transcriptional regulators by the fibroblast nuclei from the extract.

Figure 12A:
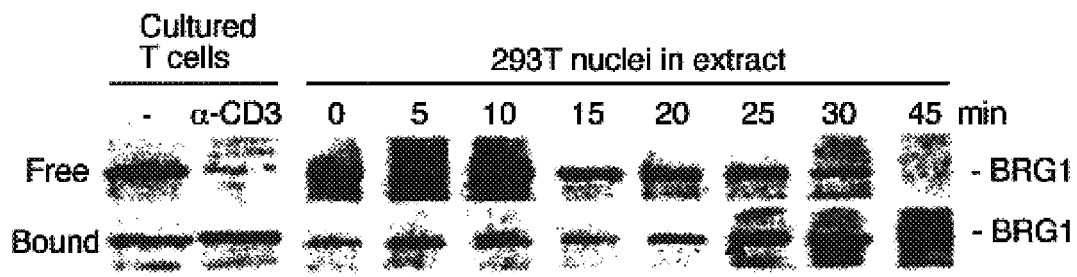

Intranuclear anchoring of the human nucleosome remodeling complex SWI/SNF was also investigated. Anti-CD3 stimulation of T-cells elicited intranuclear anchoring of the SWI/SNF complex, as determined by immunoblotting of Triton X-100-soluble and insoluble nuclear fractions with an antibody against BRG1, a marker of the SWI/SNF complex (FIG. 12A). In particular, BRG1 was immunoprecipitated from micrococcal nuclease (MNase)-soluble chromatin precleared with rabbit IgGs, using anti-BRG1 antibodies (1:40 dilution) for 2.5 hours. The immune complex was precipitated using protein A-sepharose beads, washed three times in immunoprecipitation buffer (Collas et al., J. Cell Bio. 147:1167-1180, 1999), and dissolved in SDS sample buffer. Western blots were performed using antibody dilutions of 1:500 (Collas et al., J. Cell Bio. 147:1167-1180, 1999). Over 80% of SWI/SNF was detected in a bound form within 20 minutes in stimulated T-cell extract-treated 293T nuclei; in contrast, SWI/SNF remained soluble in nuclei exposed to unstimulated T-cell extract (FIG. 12A).

Figure 12B:
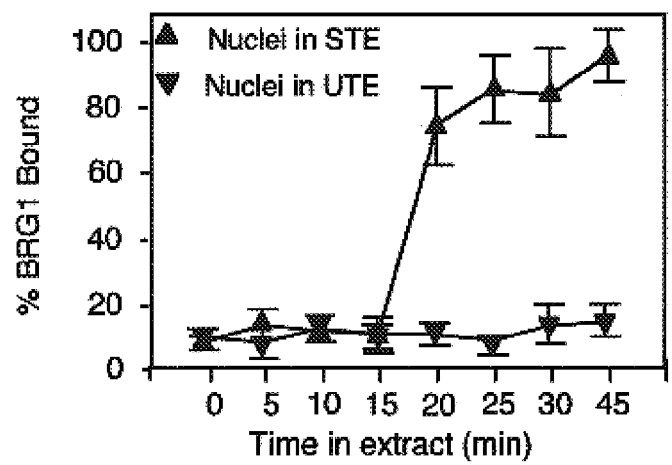
FIG. 12B is a graph of the percent of bound SWI/SNF in 293T nuclei exposed to stimulated T-cell extract or unstimulated T-cell extract, based on densitometric analysis of duplicate blots.

Additionally, ATPase activity of the SWI/SNF complex was determined in a standard luciferin-luciferase assay after immunoprecipitation of the complex using anti-BRG1 antibodies. BRG1 immune precipitates ("BRG1-IPs") purified from 293T input nuclei or unstimulated T-cell extract-treated nuclei displayed no or little ATPase, based on elevated ATP levels in the assay (FIG. 12B). However, BRG1-IP isolated from nuclei treated with the stimulated T-cell extract displayed an ~8-fold increase in ATPase activity, reducing the ATP level in the assay from 2,500 to 300 RLU. No activity was detected in control precipitates using pre-immune IgGs (FIG. 12B). These results indicate that the stimulated T-cell extract promotes intranuclear anchoring of the SWI/SNF nucleosome remodeling complex and ATPase activity of the bound complex in 293T nuclei.

Potential for gene expression often correlates with hyperacetylation of histone H4. As an additional marker of nuclear reprogramming, changes in H4 acetylation at the IL-2 locus in stimulated T-cell extract- and unstimulated T-cell extract-treated 293T nuclei were measured. Chromatin immunoprecipitation (ChIP) experiments were performed using an antibody against all forms of acetylated H4 ("acH4," FIG. 12C). In particular, intact nuclei were isolated from 293T, NT2, and unstimulated peripheral blood T-cells by Dounce-homogenization and stored frozen (Collas et al., J. Cell Bio. 147:1167-1180, 1999). Soluble chromatin was prepared from purified nuclei by MNase digestion (O'Neill and Turner, Methods Enzymol. 274:189-197, 1996), and nuclear matrices, defined as Triton X-100, DNAse, and RNAse extraction-resistant structures, were isolated as described (Steen et al., J. Cell Biol. 149:531-536, 2000). ChIP was performed after solubilization of chromatin with 0.1 U MNase per μg DNA using an anti-pan-acetylated histone H4 antibody (O'Neill and Turner, Methods Enzymol. 274:189-197, 1996). DNA was isolated by phenol-chloroform extraction from antibody-bound and unbound fractions, and the IL-2 locus was identified by dot blot analysis. An IL-2 probe was synthesized and fluoresceinated by random priming (Amersham) using as a template a 467-bp IL-2 PCR product amplified from genomic DNA by PCR as described above. Hybridization was detected by chemiluminescence (Collas et al., J. Cell Sci. 112:1045-1054, 1999). The β-actin probe was synthesized and labeled as described (Collas et al., J. Cell Sci. 112:1045-1054, 1999).

Figure 12C:
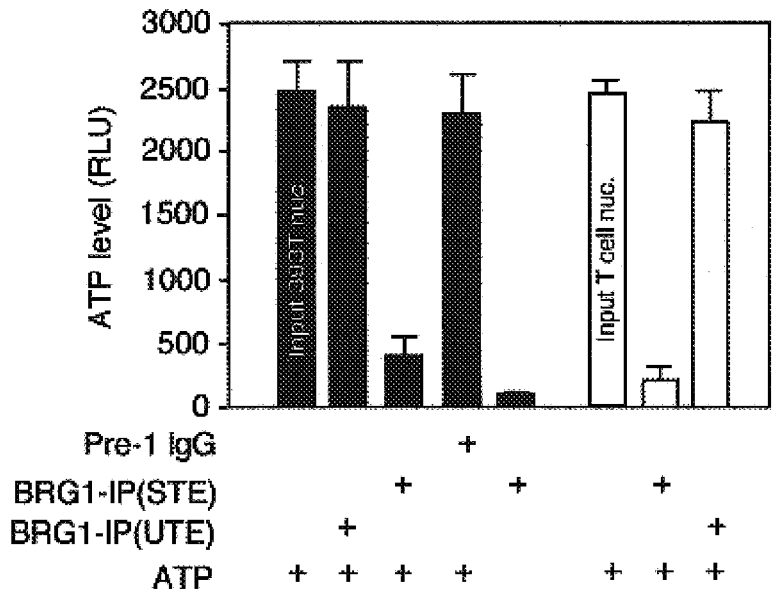
FIG. 12C is a graph of the ATPase activity of the SWI/SNF complex. Following exposure of 293T nuclei to stimulated T-cell extract or unstimulated T-cell extract, SWI/SNF was immunoprecipitated from nuclear lysates using anti-BRG1 antibodies and hydrolysis of 1 nM exogenous ATP ("ATP+") by the immune precipitate ("BRG1-IP") was determined in a luminometric assay. Control precipitations were carried out using pre-immune IgGs ("Pre-I IgG"). ATP levels are expressed as mean (±SD) relative light units (RLU). Elevated ATP levels reflect low ATPase activity of the BRG1-IP.

In input nuclei and nuclei incubated in unstimulated T-cell extract, IL-2 was detected exclusively in anti-acH4 unbound chromatin, suggesting hypoacetylation of H4 in the IL-2 locus (FIG. 12C). In contrast, IL-2 was detected in anti-acH4 bound chromatin of nuclei treated with stimulated T-cell extract, reflecting enhanced H4 acetylation at the IL-2 locus in these nuclei (FIG. 12C). As anticipated, reprobing filters with a probe against the constitutively expressed β-actin gene revealed hyperacetylated H4 at the β-actin locus (FIG. 12C).

Thus, stimulated T-cell extract elicits enhanced H4 acetylation at the IL-2 locus in 293T nuclei, providing evidence for physiological chromatin remodeling.

Figure 12D:
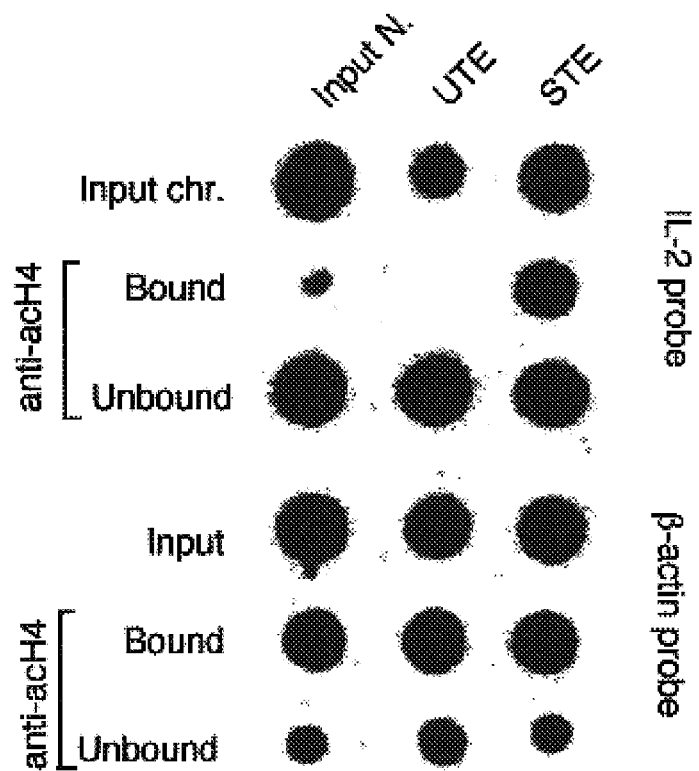
FIG. 12D is an immunoblot showing the hyperacetylation of the IL-2 locus in 293T nuclei. MNase-soluble chromatin was prepared from input 293T nuclei ("Input N"), and the nuclei were exposed to unstimulated T-cell extract or stimulated T-cell extract. Acetylated H4 was immunoprecipitated, and DNA was isolated from anti-acH4 precipitate ("Bound") and supernatant ("Unbound") fractions. DNA was dot-blotted and-hybridized to an IL-2 probe (top rows) and a control β-actin probe (bottom rows).
Figure 12E:
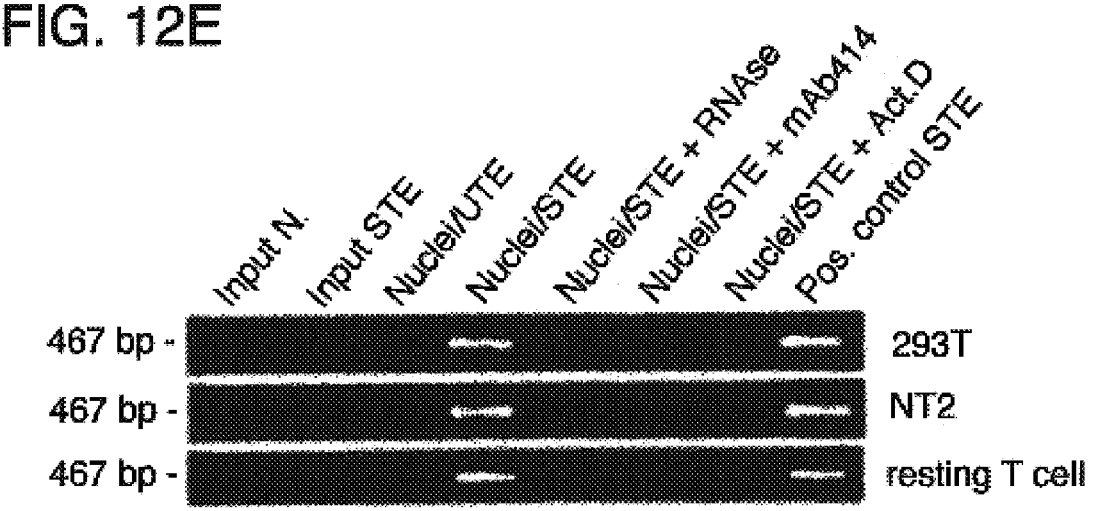
FIG. 12E is a picture of a set of gels showing transcription of the IL-2 gene. Nuclei from 293T, NT2, and resting T-cells were incubated for two hours in unstimulated T-cell extract ("Nuclei/UTE") or stimulated T-cell extract ("Nuclei/STE"). As controls, nuclei were incubated in stimulated T-cell extract containing either 100 μg/ml RNAse A, mAb414, or 50 nM actinomycin D ("ActD"). RNA was isolated from the reaction mix, and IL-2 transcription was examined by RT-PCR.

Another and more stringent indicator of nuclear reprogramming was induction of IL-2 transcription in 293T fibroblast nuclei exposed to stimulated T-cell extract (FIG. 12D). Total RNA was isolated using the Qiagen RNeasy kit, and 15 ng RNA was used as the template for RT-PCR using the Promega Access RT-PCR System. A 467-bp product was amplified using the IL-2-specific primers 5'-ATGTACAGGATGCAACTCCTGTCTT-3' (SEQ ID NO: 5) and 5'-GTTAGTGTTGAGATGATGCTTTGAC-3' (SEQ ID NO: 6) by 30 cycles of denaturation at 94° C. for 30 seconds, annealing at 60° C. for one minute, and extension at 72° C. for one minute. RT-PCR analysis indicated that the IL-2 gene was activated in the stimulated T-cell extract, but not in the unstimulated T-cell extract. As expected from the above results, the IL-2 transcript was absent from input nuclei, input stimulated T-cell extract, and nuclei exposed to stimulated T-cell extract containing either 100 pg/ml RNAse A, mAb414, or 50 nM of the RNA polymerase II (Pol II) inhibitor, actinomycin D (FIG. 12D). Similar results were obtained with neuronal precursor NT2 nuclei and resting T-cell nuclei (FIG. 12D). Collectively, these data indicate that the stimulated T-cell extract supports chromatin remodeling and RNA Pol II-dependent activation of the repressed IL-2 gene in T-cell and non-T-cell nuclei.

EXAMPLE 6

Reprogramming of Permeabilized Cells

The ability to reprogram whole cells, in addition to purified nuclei, was demonstrated as described below. 293T fibroblasts grown on coverslips were reversibly permeabilized with the bacterial toxin Streptolysin O, exposed to extract of readily available stimulated Jurkat cells or neuronal precursor cells, resealed with 2 mM $CaCl_2$, and expanded in culture. Reprogramming into T-cells was evaluated by alterations in gene expression, expression of T-cell-specific proteins, and induction of a T-cell-specific function in the reprogrammed 293T fibroblasts. Reprogrammed 293T fibroblasts exposed to neuronal extracts were analyzed for expression of neuronal proteins.

For these studies, 293T fibroblasts were grown on 16-mm poly-L-lysine-coated coverslips in RPMI1640 to 100,000 cells/coverslip in 12-well plates. Cells were permeabilized in 200 ng/ml streptolysin O in $Ca^{2+}$-free Hanks Balanced Salt Solution (Gibco-BRL) for 50 minutes at 37° C. in regular atmosphere. Over 80% of 293T cells were permeabilized under these conditions, as judged by propidium iodide uptake. Streptolysin O was aspirated; coverslips overlaid with 80 µl of either 293T, Jurkat-Tag, or NT2 extract; and incubated for one hour at 37° C. in $CO_2$ atmosphere. Each extract contained the ATP generating system and 1 mM each of ATP, CTP, GTP and UTP. Extracts from Jurkat-TAg cells were prepared as described above after co-stimulation for 1-2 hours with 40 ng/ml anti-CD3 antibodies (clone SpvT3d obtained from A. M. Rasmussen, Norwegian Radium Hospital, Montebello, Norway) and 0.1 µM PMA. The neuronal precursor NT2 extract was prepared from confluent NT2 cells (Stratagene) by sonication and sedimentation as described above. To reseal plasma membranes, RPMI1640 containing 2 mM $CaCl_2$ (added from a 1 M stock in $H_2O$) was added to the wells, and the cells were incubated for two hours at 37° C. This procedure resealed ~100% of the permeabilized cells. $Ca^{2+}$-containing RPMI was replaced by RPMI, and the cells were expanded for several weeks.

Transcription levels in reprogrammed fibroblasts exposed to the Jurkat extract were compared to those of 293T cells exposed to a 293T extract ('control cells') 10 days post-reprogramming reaction. A human cytokine expression array containing 375 cDNAs was used to monitor changes in gene expression. In particular, mRNA was isolated (mRNA Direct™, Dynal) from 'reprogrammed' and control cell pellets frozen in liquid nitrogen at 10 days post-reprogramming. One µg mRNA was used as the template for cDNA synthesis (cDNA Labeling and Hybridization Kit, R&D Systems) with $\alpha$-$^{33}$P-dCTP and cytokine-specific primers (R&D Systems) according to the manufacturer's protocol. Purified probes were hybridized to Human Cytokine Expression Arrays (R&D Systems) under recommended conditions. Arrays were exposed to a phosphorscreen for six days. Hybridization was quantified on a phosphorimager and analyzed using the Phoretix Array V.2 analysis software.

Figure 13:
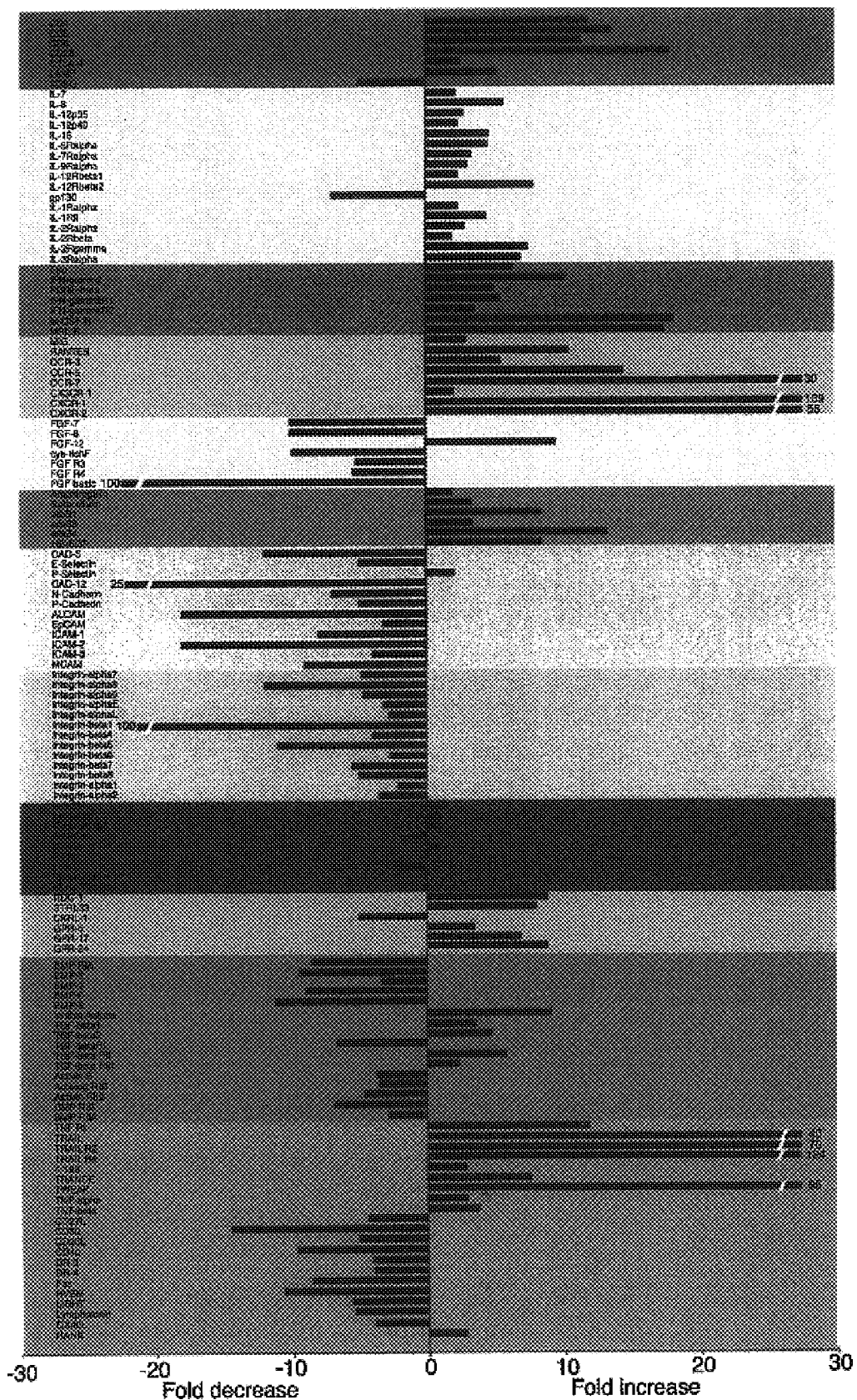
FIG. 13 is a graph demonstrating that 293T fibroblasts reprogrammed in the Jurkat-TAg extract display altered gene expression. Relative mRNA levels in 293t cells incubated in stimulated Jurkat-TAg extract or in control 293T extract were compared using a cytokine gene expression array. Bars represent fold increase or decrease in transcription of indicated genes in Jurkat extract-treated cells, measured as the ratio of reprogrammed/control probe hybridization signal strength. Genes with an over two-fold increase or decrease in expression level are shown. Different color backgrounds separate the following distinct gene groups: cell surface molecules, interleukins and receptors, cytokines and receptors, FGFs, EGFs, adhesion molecules, integrins, housekeeping gens, orphan receptors, TGF family proteins, and TNF family proteins.

Over 120 genes were up- or down-regulated as a result of reprogramming (FIG. 13; only transcripts up- or down-regulated more than two-fold are shown). Subsets of genes encoding hematopoietic cell surface antigens, interleukins and interleukin receptors, cytokines and cytokine receptors, chemokines and chemokine receptors, epidermal growth factors, and orphan receptors were up-regulated. Several genes of the FGF, adhesion molecule, and integrin families were down-regulated. Several genes of the TGFβ and TNF families were also either up- or down-regulated. No neutrophic factor transcripts were affected, nor was expression of house keeping genes affected (FIG. 13). Similar results were obtained in duplicate arrays from separate reactions examined at 13 days post-reprogramming. Thus, hematopoietic genes are turned on or up-regulated in 293t cells exposed to a Jurkat extract, whereas genes for FGFs, adhesion molecules, and cytoskeletal components are down-regulated or repressed.

Figure 14A:
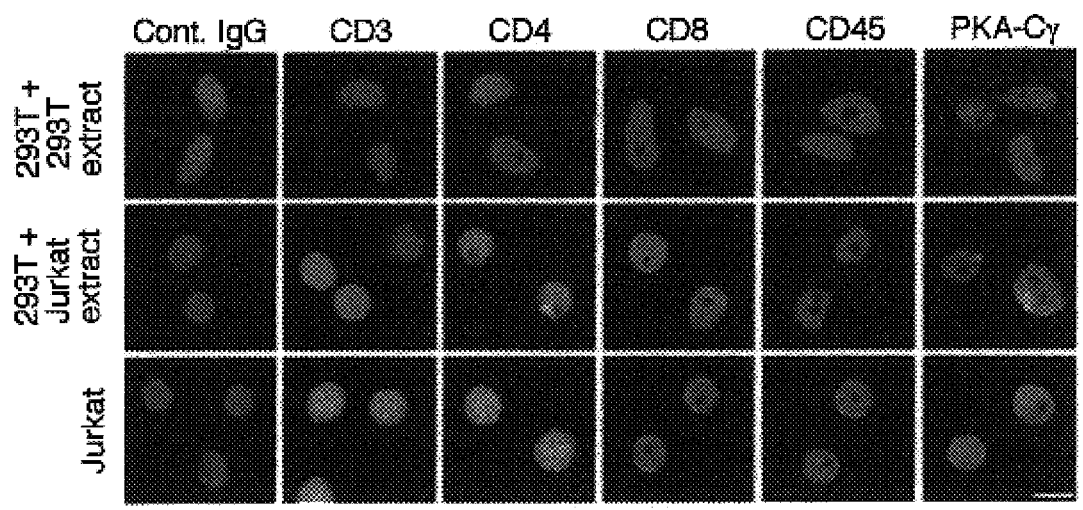
FIGS. 14A-14C demonstrate that 293T fibroblasts reprogrammed in Jurkat-TAg extract exhibit hematopoietic cell markers and function.
Figure 14B:
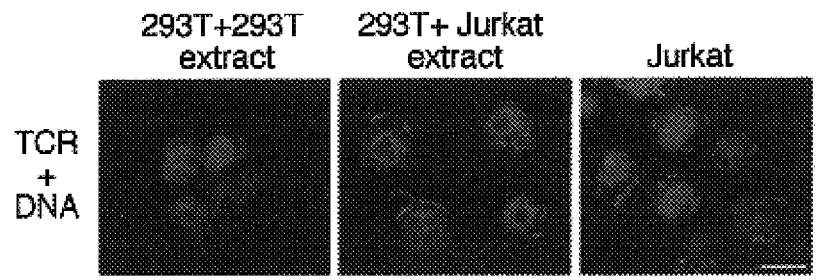

Expression of hematopoietic cell-specific surface antigens in reprogrammed fibroblasts was also evaluated. Immunofluorescence analysis of IL-2Rα and β was performed as described (Collas et al., J. Cell Bio. 147:1167-1180, 1999; anti-IL-2Rα and IL-2Rβ antibodies were obtained from R&D Systems). Analysis of other surface antigens was performed using FITC- or TRITC-conjugated primary antibodies (FITC-conjugated anti-CD3, CD4, CD8, and CD45 antibodies from Diatec and FITC-conjugated anti-TCRαβ antibody from Pharmingen). Immunofluorescence analysis showed that CD3, CD4 and CD8 were detected by 4 days post-reprogramming, and the CD45 tyrosine phosphatase was detected by 11 days post-reprogramming in most reprogrammed cells but not in control cells (FIG. 14A). Furthermore, the α and β chains of the TCR complex were expressed in the reprogrammed fibroblasts, based on immunofluorescence labeling with an antibody against TCRαβ (FIG. 14B).

Figure 14C:
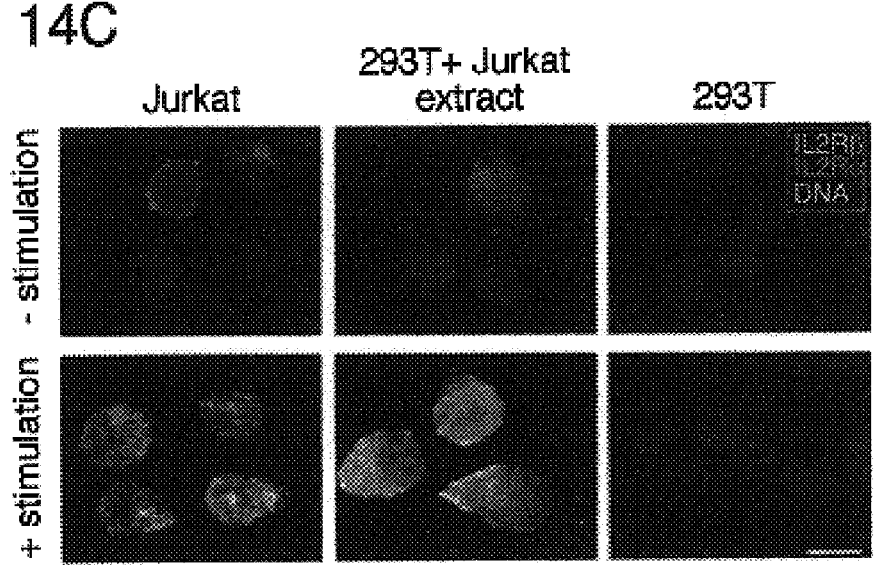

Expression of immune cell surface receptors in reprogrammed fibroblasts prompted investigation of functional reprogramming. Unstimulated T-cells express the low affinity IL-2 receptor β (IL-2Rβ). High affinity IL-2R requires induction of IL-2Rα by TCR-CD3 complex stimulation. TCR-CD3-dependent induction of IL-2Rα is indicative of normal TCR function. FIG. 14C illustrates that reprogrammed fibroblasts expressed IL-2Rβ, but not IL-2Rα, in the absence of stimulation. Furthermore, in reprogrammed cells, anti-CD3 and phorbolmyristylacetate (PMA) stimulation elicited expression of IL-2Rα that co-localized with IL-2Rβ, as shown in overlay images (FIG. 14C, "+Stimulation"). Similar results were observed with the Jurkat cells that were used to prepare the extract (FIG. 14C). As expected, stimulation of control fibroblasts did not significantly induce IL-2Rα. Altogether, these results indicate the expression of functional immune-specific receptors in the reprogrammed cells.

Figure 15:
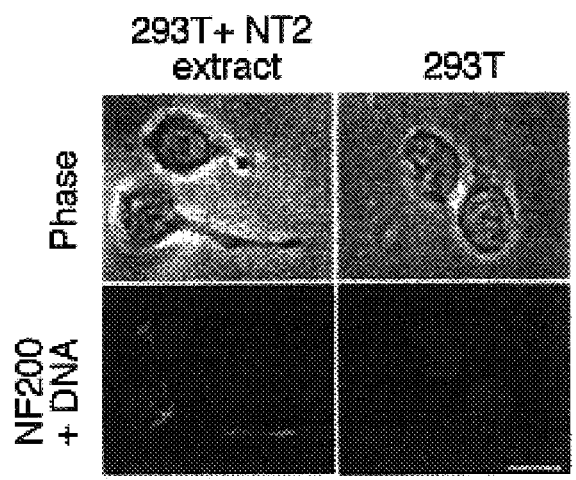
FIG. 15 is a picture of the immunofluorescence analysis of 293T fibroblasts reprogrammed in NT2 extract, demonstrating that the reprogrammed cells express the neurofilament protein NF-200. NT2 or control 293T extract-treated fibroblasts were examined by immunofluorescence using anti-NF200 antibodies at 15 days post-reprogramming. DNA was labeled with Hoechst 33342 (bar, 10 μm).

To demonstrate the general applicability of in vitro cell reprogramming, permeabilized fibroblasts were exposed to an NT2 cytoplasmic and nuclear extract for one hour at 37° C. as described above for Jurkat extracts. The cells were resealed and cultured for 15 days in low confluency in RPMI1640. Then, the expression of neurofilament protein NF200 (Debus et al., Differentiation 25:193-203, 1983) was examined by immunofluorescence. NF200 was strongly expressed in fibroblasts exposed to the NT2 extract, but not to a control 293T fibroblast extract (FIG. 15). Furthermore, NF200 appeared restricted to polarized outgrowths from the fibroblasts resembling elongating neurites, which occasionally contacted neighboring cells in culture. These data indicate that neuron-specific proteins can be expressed in fibroblasts under these reprogramming conditions.

In summary, these results demonstrate functional reprogramming of a somatic cell using a nuclear and cytoplasmic extract derived from another somatic cell type. These experiments illustrate activation of repressed genes and synthesis of proteins specific for another cell type in somatic fibroblasts by exposure to extracts from heterologous somatic cell types. Reprogramming fibroblast genome function in a T-cell or Jurkat-TAg extract is demonstrated by physiological nuclear uptake and assembly of transcriptional regulatory proteins, chromatin remodeling, activation of lymphoid-specific genes, down-regulation of selective sets of genes, expression of T-cell-specific antigens including CD3 and TCR, and establishment of the IL-2R assembly pathway in response to CD3-TCR stimulation. Moreover, a neurofilament protein was expressed in fibroblasts exposed to a neuronal precursor cell extract. In vitro reprogramming of differentiated somatic cells from primary cultures creates a wide range of possibilities to produce isogenic or substantially isogenic replacement cells for therapeutic applications.

EXAMPLE 7

Reprogramming of Permeabilized Cells Using T-Cell Extracts

As discussed above, functional reprogramming of a somatic cell can be achieved using a nuclear and cytoplasmic extract derived from another somatic cell type. Reprogramming of 293T fibroblasts in an extract from T-cells was evidenced by nuclear uptake and assembly of transcription factors, induction of activity of a chromatin remodeling complex, changes in chromatin composition, and activation of lymphoid cell-specific genes. The reprogrammed cells expressed T-cell-specific surface molecules and demonstrated a complex regulatory function (Håkelien et al., Nature Biotechnology 20:460-466, 2002; Landsverk et al., EMBO Reports 3:384-389, 2002).

As an alternative to using transformed T-cells (e.g., Jurkat TAg), T-cells purified from human blood were used to prepare a reprogramming extract. T-cells were isolated as described previously (Håkelien et al., 2002, supra) and cultured overnight. The extract was prepared from non-stimulated T-cells as described previously (15,000×g supernatant of a total cell lysate; Håkelien et al., 2002, supra). The protein concentration of the extract ranged from 18-25 mg/ml; and the pH was 6.7-7. Other extract preparations that may be used include 200,000×g supernatant fractions of the 15,000-g extract, which are intended to lack membrane vesicles (microsomes) that may otherwise inhibit reprogramming by blocking the pores in the plasma membrane of the permeabilized cells. Nuclear extracts can also be used instead of whole cell extracts to enrich for transcription regulators. To prepare these extracts, nuclei are isolated from T-cells by a five-minute extraction with 0.5% NP-40 (Sigma), three washes in the cell lysis buffer described above, and resuspension in 1-2 volumes of cell lysis buffer. Nuclei are lysed by sonication as described above and the lysate is sedimented at 15,000×g or at higher speeds up to 200,000×g. Alternatively, protein extracts are made from 200,000-g whole cell lysates or nuclear lysates. Lysate proteins are precipitated with ammonium sulfate and dissolved in a minimum volume of cell lysis buffer.

Figure 22:
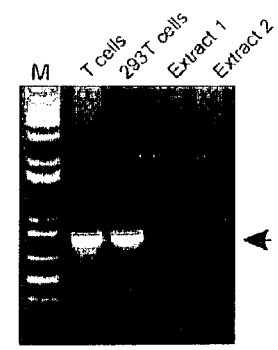
FIG. 22 is a picture of a gel illustrating the PCR analysis of the presence of T-cell DNA in reprogramming extracts. No IL-2-specific DNA fragment (arrow) is amplified from two separate extracts.
Figure 24:
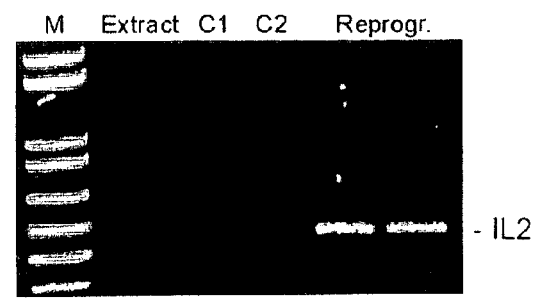
FIG. 24 is a picture of a gel of the RT-PCR analysis of transcription of the IL-2 gene by the reprogrammed cells.

Permeabilized fibroblasts that were reprogrammed in a 15,000-g extract from human blood T-cells and that were cultured as described above secreted small amounts of interleukin-2 (IL-2) in the culture medium as a result of their stimulation by the anti-CD3/anti-CD28 antibody-coated beads. IL-2 levels in the culture were approximately threefold higher than levels of IL-2 secreted by control cells or fibroblasts and approximately 14-fold lower than levels of IL-2 secreted by normal, stimulated T-cells. This secretion of IL-2 was detected in three batches of reprogrammed cells. IL-2 secretion was verified by transcriptional data from RT-PCR analysis of the reprogrammed cells (FIG. 24). Jurkat T-cell extracts were analyzed to determine whether they contained any DNA that could encode IL-2 or other markers expressed by the reprogrammed cells. No such DNA was detected in the Jurkat extracts. PCR analysis using IL-2 gene-specific primers to detect any DNA potentially present in the Jurkat extract did not yield any product after 35 PCR cycles, strongly suggesting that no detectable IL-2 DNA was present in the extract (FIG. 22). Absence of detectable DNA in the Jurkat extract was confirmed using primers for the human beta-actin gene. Because there is no exogenous IL-2 in the culture medium, the IL-2 is secreted by the reprogrammed cells.

Figures 23A, 23B, 23C, 23D, 23E:
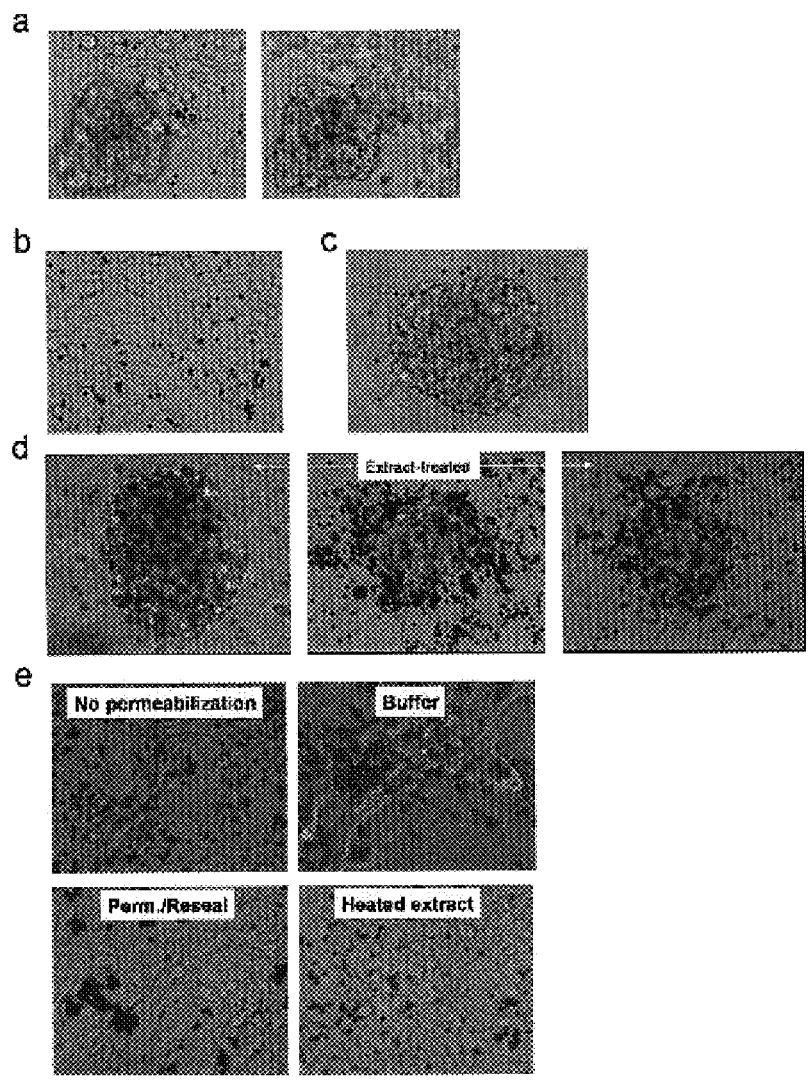
FIGS. 23A-23E illustrate changes in growth characteristics and the formation of a cluster of reprogrammed cells. Pictures in FIG. 23A are taken on two different focal planes. The dark spots are the anti-CD3 and anti-CD28 antibody-bearing beads.

To further analyze the changes in growth characteristics due to reprogramming, reprogrammed cells were cultured in RPMI1640, supplemented as described previously, in the presence of magnetic beads with anti-CD3 and anti-CD28 antibodies. These antibodies only bind to cells that express CD3 and CD28 as a consequence of reprogramming. The antibodies also stimulate the reprogrammed cells and promote their expansion. The beads were added to the culture immediately after the membrane resealing reaction was completed, at a concentration of three beads per cell. Beads were continuously present in the culture: new beads were added to the medium each time the culture medium was changed approximately every five days. As a result of these culture conditions, the reprogrammed cells formed clusters that lifted off the culture dish approximately seven days after reprogramming (FIG. 23A). The clusters grew over time, indicating cell expansion within the cluster (FIG. 23B-23D). Cells numbers within clusters were estimated to be in the hundreds. Clusters persisted for at least three weeks; longer time points were not tested because the cells were used for other analyses. One in three experiment lead to morphological changes in the cells, and approximately one in five experiment resulted in IL2 secretion. Control reprogramming reactions did not lead to cluster formation or the binding of the cells to the antibody-coated beads (FIG. 23E). The control cells also had growth characteristics similar to fibroblasts (FIG. 23B).

Additionally, expression of surface molecules was verified by flow cytometry. The data indicate that only a minor proportion (5-10%) of the extract-treated cells expressed surface receptors such as CD3, TCR, CD4, IL2 and receptor β. If desired, affinity columns can be used to selectively purify the cells expressing these markers. Using these columns, cells bearing a specific antigen (e.g., CD3) are retained on the column, while other cells are washed through the column and eluted. After the column is washed sufficiently to remove the cells with little or no expression of the desired antigen, the antigen-expressing, bound cells are eluted (e.g., eluted with free antibody or a change in salt concentration or pH).

Figure 25:
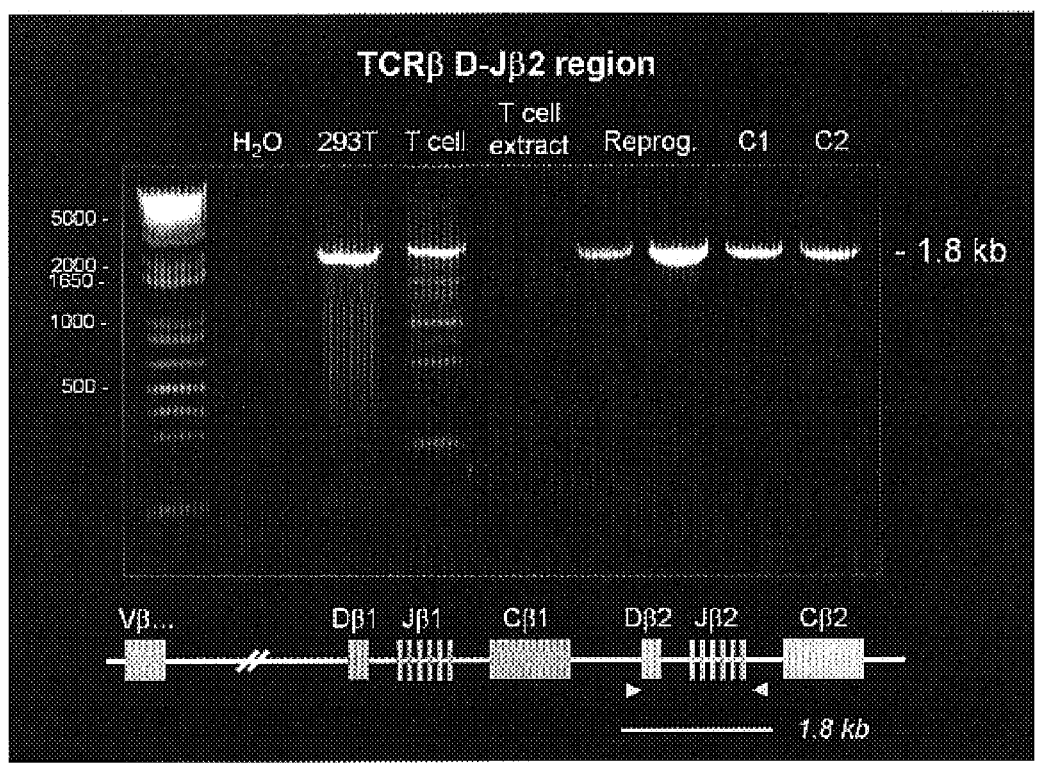
FIG. 25 is a picture of a gel illustrating the PCR analysis of TCR gene rearrangement in reprogrammed cells.

The TCR is thought to only be expressed following rearrangement of the locus at the DNA level. This rearrangement is detectable by PCR analysis of genomic DNA (see Tada et al., Curr. Biol. 11:1553-1558, 2001). To determine the origin of the TCR detected on the surface of the reprogrammed cells, DNA was purified and analyzed by PCR using primers specific for the TCRβ D-Jβ2 region (FIG. 25). When unrearranged, the PCR product is 1.8 kb in size (FIG. 25). In 293T fibroblasts, a 1.8-kb product was obtained, as expected. In normal T-cells, several bands corresponding to products of various sizes as a result of rearrangement (combinations of D with any J segment) were obtained, as expected. As reported above, no TCR DNA was detected in the T-cell extract.

In two sets of reprogrammed cells, the 1.8-kb product was also detected, with no sign of rearrangement. This result was also observed in two controls: intact cells exposed to extract (FIG. 25, C1) and cells permeabilized, washed in buffer, and resealed (FIG. 25, C2). This finding indicates that the TCR locus has not been rearranged to a detectable extent in the reprogrammed cells. According to the current understanding of TCR expression, the TCR gene of the reprogrammed cells has not been activated for functional rearrangement and expression of TCR transcripts. Thus, the TCR detected on the surface of the reprogrammed cells may result from uptake of TCR RNA and/or protein from the extract. The TCR protein from the extract may be transported within the reprogrammed cells and inserted in the cell membrane. Alternatively, extract vesicles bearing TCR protein may be fused with the reprogrammed cells, resulting in expression of TCR protein from the extract on the surface of the reprogrammed cells.

Thus, to enhance reprogramming, RNA and/or protein for a TCR of interest may be added to the reprogramming extract, or the cells used to generate the reprogramming extract may be genetically modified to express TCR RNA and protein of interest. In desirable embodiments, at least 1 ng/ml, 10 ng/ml, 100 ng/ml, 500 ng/ml, 1 μg/ml, 10 μg/ml, 100 μg/ml, 500 μg/ml, 1 mg/ml, 10 mg/ml, 20 mg/ml, 50 mg/ml, or 100 mg/ml RNA encoding a TCR of interest is added to, or expressed by, the extract. The concentration of exogenous or endogenous TCR mRNA is desirably at least 1 nM, 10 nM, 100 nM, 500 nM, 1 μM, 10 μM, 100 μM, 500 μM, 1 mM, 10 mM, 100 mM, 200 mM, or 500 mM. The concentration of TCR alpha and/or beta protein subunits added to, or expressed by, the extract is desirably at least 1 ng/ml, 10 ng/ml, 100 ng/ml, 500 ng/ml, 1 μg/ml, 10 μg/ml, 100 μg/ml, 500 μg/ml, 1 mg/ml, 10 mg/ml, 20 mg/ml, 50 mg/ml, or 100 mg/ml. The TCR protein subunits are either (i) added separately in the extract to be taken up as separate units and bind within the cell to be reprogrammed prior to insertion into the membrane or (ii) mixed in a binding buffer (e.g., 100 mM Tris at pH 7.5 or 50 mM Hepes at pH 7.5, 50 mM NaCl or 50 mM KCl, 1 mM DTT, and a cocktail of protease inhibitors) and then added as an alpha-beta complex to the extract or medium.

EXAMPLE 8

Reprogramming to Generate T-Cells Reactive with a Tumor Antigen

To generate reprogrammed T-cells reactive with a specific tumor antigen, donor cells (e.g., fibroblasts) are collected from a patient and reprogrammed in a T-cell extract as described above. Then, undesired CD4$^+$ and CD4$^+$/CD8$^+$ cells are preferably eliminated (for example, as described below). The remaining CD8$^+$ T-cells are optionally cultured in the presence of one or more tumor antigens to expand the reprogrammed T-cells expressing a TCR reactive with the tumor antigen. Alternatively, a nucleic acid encoding a TCR reactive with the antigen is inserted into the cells before, during, or after reprogramming. The resulting reprogrammed T-cells are administered to a subject (e.g., the subject from whom the donor cells were obtained). These methods may also be used to establish a cell bank of reprogrammed T-cells that are useful to treat any potential tumor a mammal (e.g., a human) may have. These methods are described further below.

Exemplary Conditions for Reprogramming and Incubating Cells

To reprogram donor cells such as fibroblasts, a reprogramming extract is prepared from peripheral blood T-cells obtained from several buffey coats purchased from a blood bank. A 0.5-liter buffey coat preparation gives 30-100 million CD8$^+$ T-cells. The extract is prepared as described herein. Healthy fibroblasts from a cancer patient are reprogrammed in the T-cell extract as described herein. The reprogrammed T-cells are expanded for approximately 7 days in culture using interleukin-2 (IL-2), anti-CD3 beads, and anti-CD28 beads (Dynal Biotech, Oslo, Norway) in the culture medium.

Elimination of Undesired Self-Reacting, CD4$^+$, and CD4$^+$/CD8$^+$ Reprogrammed T-Cells To eliminate "self"-reacting T-cells that may elicit an autoimmune reaction when administered to the recipient mammal, a standard cytotoxic assay is used. In particular, the reprogrammed T-cells are mixed with macrophages and natural killer cells from the recipient mammal. The "self"-reacting T-cells are immediately killed by complement-mediated lysis. The remaining living T-cells are collected and expanded in the culture as described above.

Negative selection of CD8$^+$ T-cells may be performed to eliminate CD4$^+$ and CD4$^+$/CD8$^+$ T-cells, which may otherwise die by apoptosis in the thymus. This selection step is performed by removing CD4-containing cells from the culture with anti-CD4 beads (Dynal). The remaining T-cell population is the desired CD8$^+$ cells. As an alternative to performing this negative selection step, a reprogramming extract formed from CD8$^+$ T-cells or CD4$^+$ T-cells can be used to produced the desired reprogrammed cells that are not double positive.

Analysis of T-Cell Receptor Expression

The ability of the reprogrammed cells to express a T-cell receptor (TCR) is determined by immunofluorescence using antibodies reactive with each chain of a TCR (α, β, g, d). If desired, additional antibodies can be used to determine the specificity of the expressed TCR. Flow cytometry may be used in combination with cell sorting to collect a population of T-cells expressing all chains of the TCR, and thereby a potentially functional TCR.

Because a mixed population of T-cells is used to prepare the reprogramming extract, the reprogrammed T-cells may express multiple variants of the TCR because each T-cell may express a different TCR. The TCR protein or nucleic acid is sequenced using standard sequencing techniques. Because the sequences of many TCRs are known, the TCR sequence of the variable region indicates the specific antigen that the TCR is directed against. Thus, reprogrammed T-cells that express a TCR against a particular tumor antigen can be selected.

Optional Incubation of Recombinant Cells with an Antigen of Interest

To induce the proliferation of T-cells reacting specifically with a particular tumor antigen, the reprogrammed T-cells are optionally exposed to one or more tumor antigens (e.g., an antigen from a library of tumor antigenic peptides). Enrichment of these cells produces a T-cell clone specific for that antigen. Exemplary libraries of tumor antigens include commercially available libraries, libraries made by coating the bottom of a 96-well plate with recombinant tumor antigens and ~50,000 T-cells per well, and libraries of tumor antigens linked to magnetic beads such as Dynal beads. Examples of tumor antigens include v-Ras, v-Src, and the antigens listed in Table 1.

TABLE 1

Exemplary Antigens

| Antigen | Associated Cancer | GenBank Number/Reference |
|---|---|---|
| Prostate-specific antigen (PSA)/human kallikrein 3 (hK3) | Prostate cancer | AF335478; AK335477 |
| Human kallikrein 2 (hK2)/human glandular kallikrein 1 | Prostate cancer | AF174646 |
| Melanoma-associated antigen (MAGE) | Hepatocellular carcinoma, breast cancer; expressed by a broad range of human tumors | XM03502 |
| B melanoma-associated antigen (BAGE) | Expressed by a broad range of human tumors | XM03502 |
| NY-ESO-1 protein A | Expressed by a broad range of human tumors; melanoma; synovial sarcomas | AJ003149 |
| HOM-TES-14/synaptonemal complex protein 1 | Cutaneous T-cell lymphoma | XM032672 |
| cTAGE-1 (CTCL-associated antigen 1) | Cutaneous T-cell lymphoma | AF177229 |
| SSX-4 | Gastric carcinoma, breast cancer | NM005636 |
| Pmel17/gp100 | Melanoma | S73003 |
| SSX-3 | Breast cancer | U90840 |
| SSX-2 | Breast cancer | NM003147 |
| GAGE | Expressed by a broad range of human tumors; neuroblastoma | |
| MAGE-C1 | Cutaneous T-cell lymphoma | XM051674 |
| XAGE-1b | Melanoma | AJ290447 |
| LAGE-1 | Esophageal carcinoma; gastric carcinoma | AJ223041 |
| HMB-45 | Hepatic angiomyolipoma; renal angiomyolipoma; lung cancer | |
| Melan-A | Hepatic angiomyolipoma; renal angiomyolipoma; melanoma; retinal | NM005511 |

TABLE 1-continued

Exemplary Antigens

| Antigen | Associated Cancer | GenBank Number/Reference |
|---|---|---|
| | pigment epithelium (RPE) adenoma | |
| Mart-1 | Melanoma; breast cancer | U06452 |
| Adnab-9 (adenoma-associated antigen) | Adenocarcinoma; colorectal cancer | AA552696 |
| CaCo3/61 | Colorectal cancer | Hum Pathol. 1999 Apr; 30 (4): 467-73. |
| FBB2/29 | Colorectal cancer | Hum Pathol. 1999 Apr; 30 (4): 467-73. |
| NCAM 123C3 (CD56) | Lung cancer | XM041415 |
| MITF (microphthalmia-associated transcription factor) | Clear cell sarcoma; melanoma | ABO61771 |
| PARIS-1 | Prostate cancer | Biochem Biophys Res Commun 2002 Jan 18; 290 (2): 830-8; XM005525 |
| G250 | Renal cell carcinoma | AJ010588 |
| Muc1 (upregulation) | Colorectal carcinoma and lymph node metastasis | XM053256 |
| TFF1 (trefoil factor 1) | Renal Cell carcinoma; breast cancer | XM4009779 |
| Muc4 | Pancreatic adenocarcinoma | XM038251 |
| Muc1-C and -D (Muc1 splice variants) | Cervical cancer | Gynecol Oncol 2001 Nov; 83 (2): 343-7 |
| 9D7 | Renal cell carcinoma | Int J Cancer 2002 Jan 10; 97 (2): 217-24 |
| HER2 (human epidermal growth factor receptor 2) | Gastric cancer; non-small-cell lung cancer (NSCLC); breast cancer; colorectal and pancreatic adenocarcinomas | |
| Bcl-2 | Oral leiomyosarcoma | XM008738 |
| Ki-67 | Prostate cancer; cystosarcoma phyllodes (breast cancer); hypopharyngeal carcinoma | XM088291 |
| CO17-1A/GA733 (CEA) BW494/32 CA19-9 | Colorectal carcinoma Pancreatic cancer Pancreatic and biliary cancer; gastric cancer | BM501764 |

For this incubation with a tumor antigen, standard methods can be used to expand the desired cells that are reactive with the antigen (see, for example, Gjertsen et al., Int. J. Cancer 72:784-790, 1997). For example, reprogrammed cells are plated in 24-well tissue culture plates (Nunc, Roskilde, Denmark) at a density of 1, 2, 3, 4, 5, 6, 7, 8 or $9 \times 10^6$ (preferably, $2 \times 10^6$ cells per well). Cells are stimulated with an antigen (e.g., one or more tumor specific antigens at a concentration of 1, 5, 10, 25, 50, 75 or 100 µM, (preferably 25 µM). Between 5 days and 15 (e.g., day 9), T-cell blasts are split by dilution. Inspection of blasts in the microscope allow one to seed 1 to 10 cells (e.g., 5 cells per well) in Terasaki plates (Nunc). Cells are grown on irradiated peripheral blood monocytes (PBMC) isolated from the patient and cultured at 1, 2, 3, 4 or $5 \times 10^4$ feeder cells per well, preferably $2 \times 10^5$ cells per well. Reprogrammed cells are propagated with the antigen (e.g., a tumor antigen at a concentration between 1 and 100 µM as described above) and between 1 and 10 µM per mL of recombinant human interleukin 2 (rIL-2) purchased commercially. After between 5 and 15 days (e.g., day 9), reprogrammed cells are transferred to flat bottomed 96 well plates coated with approximately 1, 2, 3, 4 or $5 \times 10^4$ irradiated PBMC per well (preferably 2×10⁵ cells per well). Recombinant IL-2 is added to the cultures at a concentration of 1 to 100 µM (preferably 25 µM), together with 0.5, 1, 2.5 or 5 µg/mL (preferably 1 µg/ml) of phytohaemagglutinin (PHA) and cultivated for 3 to 10 days (preferably 6 days). Reprogrammed cells are then transferred to 24-well plates with PHA/rIL-2 and irradiated PBMC at the concentrations listed above and screened for T-cell antigen receptors specific for the immunizing antigenic peptide. Screening of the expressed TCR may be performed by PCR analysis, cloning of the TCR gene, and DNA sequencing. In addition, the TCR protein may be isolated by electrophoresis and sequenced using standard methods. Alternatively, a standard ELISA assay may be used to determine the amount of antigen bound to an expanded T-cell, and standard assays may be used to measure the activation of a T-cell by the antigen.

Alteration of Reprogrammed Cells by Transfection with an Antigen-Specific TCR Gene As an alternative to expanding reprogrammed T-cells using an antigen of interest, standard methods can be used to transfect cells with a nucleic acid encoding a TCR specific for an antigen of interest (see, for example, Bell et al. Nature Medicine 7: 1155-1158, 2001; Ausubel et al. Current Protocols in Molecular Biology, John Wiley & Sons, New York, 2000). Between $10 \times 10^6$ and $50 \times 10^6$ (e.g., between $20 \times 10^6$–$30 \times 10^6$) reprogrammed T-cells are resuspended in 250 µL 1640 RPMI containing 5% fetal calf serum (FCS) without antibiotics and mixed with DNA (0.1, 1, 10, 20, 40, 60, 80 or 100 µg DNA per transfection). The DNA encodes fully active and clonotypic TCRs (e.g., TCRs known to be specific for certain tumor forms or TCRs isolated from T-cells expanded in the presence of an antigen of interest as described above) and is inserted into the cells by electroporation. Electroporation is performed, for example, with a BTX Electro Square Porator T820 (BTX Corp., San Diego, Calif.) using the machine settings: low voltage, pulse length=10, 1.4 mm gap cuvettes, and either 310, 320, 340, 360 or 380 V.

Insertion of the transfected TCR into the T-cell genome may be assessed by fluorescence in situ hybridization (see, for example, Collas and Aleström, 1998; Transgenic Res. 7:303-309, 1998; Collas et al., J. Cell Sci. 112, 1045-1054, 1999) or by restriction enzyme analysis and Southern blotting (see, for example, Collas et al., Nucl. Acids Res. 26, 4454-4461,1998), and verified by sequencing the insertion domains.

Expression of the transfected TCR gene(s) may be evaluated by RT-PCR using specific primers. Protein expression may be monitored by immunofluorescence using specific antibodies against the chosen TCR. The ability of the tumor antigen to activate the transfected T-cell can also be measured using standard assays. Exemplary assays include a T-cell proliferation assay based on relative incorporation of ³H-thymidine in the proliferating T-cells and an assay for the induction of "capping" of the TCR on the T-cell surface upon antigen stimulation. Capping is monitored by immunofluorescence using antibodies against conserved regions of the TCR (e.g., anti-TCRα and β chain antibodies; Håkelien et al., Nat. Biotechnol. 320, 2002, in press; Skalhegg et al., Science 263, 84-87, 1994).

Applications of Reprogrammed T-Cells with a Desired TCR

The desired reprogrammed T-cells with a TCR specific for a tumor antigen are optionally further cultured and expanded with anti-CD3 and anti-CD28 beads for 7-14 days. The expanded T-cells are preferably purified using standard methods such as column chromatography or magnetic bead purification using an immobilized antigen. Potentially, each T-cell clone is frozen and stored in a "T-cell bank" for the patient. Thus, these methods allow the generation of a bank of T-cells that express a TCR against antigens from any possible type of cancer that patient may develop (e.g., colon cancer, prostate cancer, ovarian cancer, lymphomas, glycomas, melanomas, and osteosarcomas).

Alternatively, the T-cells are transplanted into the patient. The reprogrammed T-cells are administered to the patient by intravenous infusion in escalating doses of $3.3 \times 10^7$, $1 \times 10^8$, $3.3 \times 10^8$ and $1 \times 10^9$ cells/m² of body surface area weekly for four weeks (Walter et al., N. Engl. J. Med. 333:1038-1044, 1995). T-cell activity may be assessed before, during, and/or after the therapy using standard methods such as those described below. The ability of the administered cells to decrease the size of a tumor or decrease the number of cancerous cells in a patient can also be measured. If desired, the dose of the administered cells can be adjusted over time based on the magnitude of the effect of the cells on the number of cancerous cells in the patient.

Maturation of Reprogrammed Cells In Vivo

As an alternative to reprogramming cells in a T-cell extract to produce desired T-cells, cells can be reprogrammed in a stem cell extract (e.g., a hematopoietic stem cell extract formed from hematopoietic stem cells purified from bone marrow) to form stem cells or other T-cell precursors that differentiate into T-cells after being administered to a recipient mammal (Greiner et al., Stem Cells 16: 166-177, 1998 and references therein). These reprogrammed cells can be genetically modified as described above by the insertion of a nucleic acid encoding a TCR specific for a particular tumor antigen.

To further study the maturation of reprogrammed cells (e.g., cells reprogrammed in a T-cell extract or a stem cell extract such as a hematopoietic stem cell extract) into T-cells in vivo, severe combined immunodeficiency (SCID) mice or other immunocompromised animals can be used to produce mature clonotypic T-cells from donor cells (e.g., fibroblasts) in vivo (Greiner et al., Stem Cells 16: 166-177, 1998 and references thererin; Pollock et al., Fund. Appl. Toxicol. 22:130-138, 1994). In particular, intravenous injections of $10 \times 10^4$ to $100 \times 10^4$ reprogrammed cells (e.g., $50 \times 10^4$ cells) are performed. Animals are sacrificed at specific time points (preferably every third day up to two weeks and then every week up to a year), and spleenocytes, thymocytes, and peripheral blood T-cells are taken from the sacrificed animals. Flow cytometry analysis (FAC scan) is performed to monitor the continuity of T-cell phenotype by staining for all typical T-cell markers (preferably CD2, CD3, CD4/CD8, CD25, CD28 and various isoforms of CD45). Staining is performed using commercially available specific antibodies (see, e.g., Håkelien et al., Nat. Biotechnol 320, 2002, in press) for flow cytometry analysis as described in Gjertsen et al., supra. The T-cells of the mice are tested for lymphokine and cytokine expression (preferably IL-1 to IL-16, TNF, and TGF) using commercially available antibodies and ELISA kits (e.g., kits from R&D or Pharmingen). Functional assays for specific T-cell activation (e.g., activation by the tumor antigen) and cytotoxicity using the $^{51}$Cr-release cytotoxicity assay may also be performed. An exemplary cytotoxicity assay is described in Gjertsen et al., supra. T-cell activation assays include measuring T-cell proliferation in the presence of a stimulating antigen, based on ³H-thymidine incorporation and cell counts.

Additionally, matured T-cells can be harvested from the SCID mice and administered to other mammalian subjects (e.g., humans). If desired, to increase the number of T-cells transplanted in the subject, mature T-cells isolated from mice can be expanded in vitro in the presence of a relevant antigen (e.g., an antigen from the subject) as described above.

EXAMPLE 9

Reprogramming to Generate T-Cells Reactive with a Fat Cell, Autoimmune Generated Cell, Autoantibody, or an Infectious Pathogen The methods described in Example 8 for generating T-cells that are reactive with a tumor antigen can be generally applied to produce T-cells reactive with any antigen or cell type. For example, reprogrammed cells can be incubated with an antigen from a fat cell, autoimmune generated cell, autoantibody, or an infectious pathogen to expand the cells expressing a TCR that binds the antigen.

Exemplary fat cell antigens include leptin, PPARg1, PPARg2, SREBPIC, interleukin 6, adiponectin, resistin, adipsin, C/EBP transcription factors, insulin receptor, and TNFα. If desired, an antigen can be used that is specific for certain fat cells or that is expressed at higher levels or has increased activity in certain fat cells. For example, visceral adipose tissue is more sensitive to the lipolytic action of catecholamines and less sensitive to the antilipolytic action of insulin than subcutaneous adipose tissue and can differentially express some proteins. In particular, the inhibitor of the plasminogen activator (PAI1) is expressed in visceral adipose tissue much more than in subcutaneous adipose tissue (Alessi et al., Diabetes 46:860-867,1997). TNFα is preferentially secreted in visceral adipose tissue (Mohamed Ali et al., J Clin Endocrinol Metab. 82:4196-200, 1997). Leptin is believed to be expressed essentially by subcutaneous adipose tissue. The enzyme 11betahydroxysteroid dehydrogenase also has different levels of activity in subcutaneous and visceral adipose tissue. PPAR gamma, which participates in the differentiation of preadipocytes into adipocytes, is more active in subcutaneous than visceral adipose tissue.

Similarly, any antigen from an infectious pathogen (e.g., a protein, nucleic acid, carbohydrate, lipid, or small molecule from a pathogen or an intact pathogen such as a bacteria, virus, or yeast) can be used in the present methods. Other exemplary antigens include a cell component or intermediate (e.g., a bacterial cell wall component), a viral envelop protein such as HLA, a viral coat protein such as env or gag (e.g., HIV env or gag), any other cell surface protein (e.g., a cell receptor), carbohydrate, or component, or an antigen listed in FIG. 21. If desired, multiple antigens from the same pathogen or from different pathogens can be used to select reprogrammed T-cells reactive with these antigens. This combination of reprogrammed T-cells may be more effective than a single population of reprogrammed T-cells for preventing or treating an infection.

Additionally, reprogrammed T-cells can be generated that react with an autoimmune generated cell, such as a B-cell that produces undesired autoantibodies that bind self epitopes or a T-cell that reacts with self epitopes or destroys cells expressing these eptitopes. Reprogrammed cells that express a TCR specific for an autoantibody (e.g., such as an autoantibody listed in FIG. 20) can be used to eliminate the autoantibody and/or B-cells expressing the autoantibody for the prevention or treatment of autoimmune disease.

EXAMPLE 10

Reprogramming to Generate Stem Cells

An embryonic stem cells extract was used to reprogram permeabilized, mouse fibroblasts as described below. Similar methods can be used to reprogram other cells, such as other fibroblasts (e.g., human skin fibroblasts).

Briefly, mouse embryonic stem cells were cultured in the presence of leukemia inhibitory factor (LIF) without feeder layers using standard procedures. In particular, wild-type mouse embryonic stem cells were cultured on 0.1% gelatin-coated dishes in the absence of feeder layers in DMEM high glucose medium (Gibco) supplemented with 15% fetal calf serum, penicillin/streptomycin, 2-β-mercaptoethanol, non-essential amino acids, and leukemia inhibitory factor (LIF, 10 pg/ml, Sigma). An embryonic stem cell reprogramming extract was prepared as follows. Embryonic stem cells were harvested, washed three times in PBS, washed once in ice-cold cell lysis buffer described above, and the cell pellet was resuspended in an equal volume of cell lysis buffer. The suspension was sonicated on ice until all cells and nuclei were disrupted. The resulting lysate was centrifuged at 15,000×g for 15 minutes at 4° C. The protein concentration of the extract was approximately 25-30 mg/ml. The supernatant ("reprogramming extract") was either used fresh or aliquoted, snap-frozen in liquid nitrogen, and stored at –80° C. until use.

Mouse NIH3T3 cells, a transformed fibroblast cell line, were cultured in DMEM medium containing 10% FCS, penicillin streptomycin, L-glutamine, and 2-β-mercaptoethanol. The cell cultures were maintained in a 5% $CO_2$ atmosphere at 37° C. The cells were grown onto 12-mm round glass coverlips coated with poly-L-lysine to a density of ~50,000 cells per coverslip. Cells were permeabilized with Streptolysin O as described above. Sreptolysin O was removed by gentle aspiration and replaced by 80 µl of mouse embryonic stem cell extract containing an ATP generating system and nucleotides. Cells were incubated in the extract for one hour at 37° C. in regular atmosphere or 5% $CO_2$. Culture medium (500 µl) containing 2 mM $CaCl_2$ was added directly to the cells which were subsequently allowed to reseal for two hours at 37° C. in a 5% $CO_2$ incubator. $CaCl_2$-containing medium was removed and replaced by regular embryonic stem culture medium containing LIF.

Figure 16A:
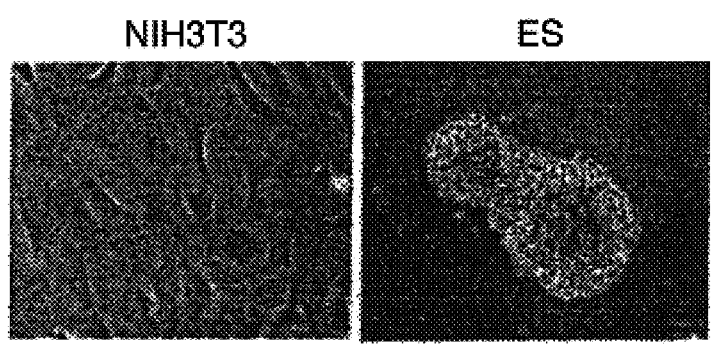
FIG. 16A is a set of pictures showing the morphology of NIH3T3 fibroblasts and mouse ES cells.
Figure 16B:
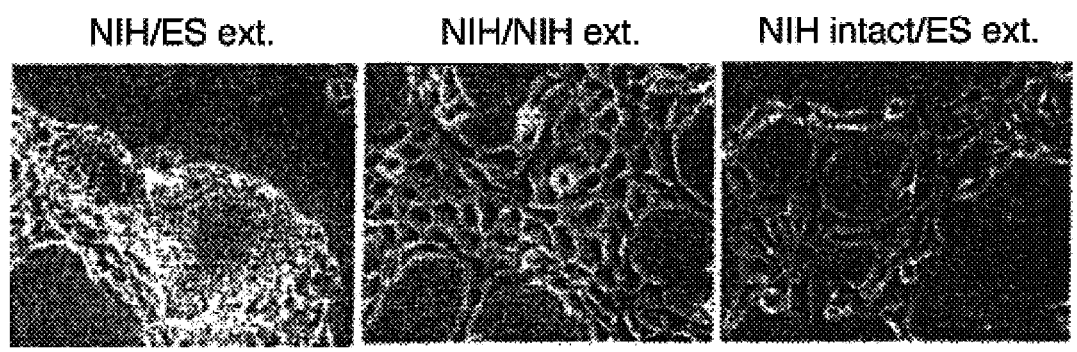
FIG. 16B is a set of pictures showing the morphology of NIH3T3 fibroblasts reprogrammed in mouse embryonic stem cell extract, fibroblasts mock-reprogrammed in NIH3T3 extract, and intact NIH3T3 cells exposed to ES cell extract. Phase contrast micrographs are shown (bars, 20 μm).

Reprogrammed NIH3T3 cells were cultured and examined on day four post-reprogramming. Phase contrast microscopy analysis showed that the cells grew in clumps, forming 'colonies' resembling those formed by embryonic stem cells (compare FIG. 16A and FIG. 16B). Some of the larger colonies such as that shown on FIG. 16B lifted off the culture dish to form embryoid bodies. In contrast, control fibroblasts permeabilized with Streptolysin O and exposed to a control NIH3T3 extract did not form colonies and maintained a typical fibroblast phenotype (compare FIG. 16B with input NIH3T3 cells in FIG. 16A). Similarly, control intact (non-permeabilizied) NIH3T3 cells exposed to the embryonic cell extract did not acquire the embryonic cell phenotype (FIG. 16B). Embryonic stem cell morphology of the reprogrammed cells was seen for at least 10 days in culture.

Figure 17:
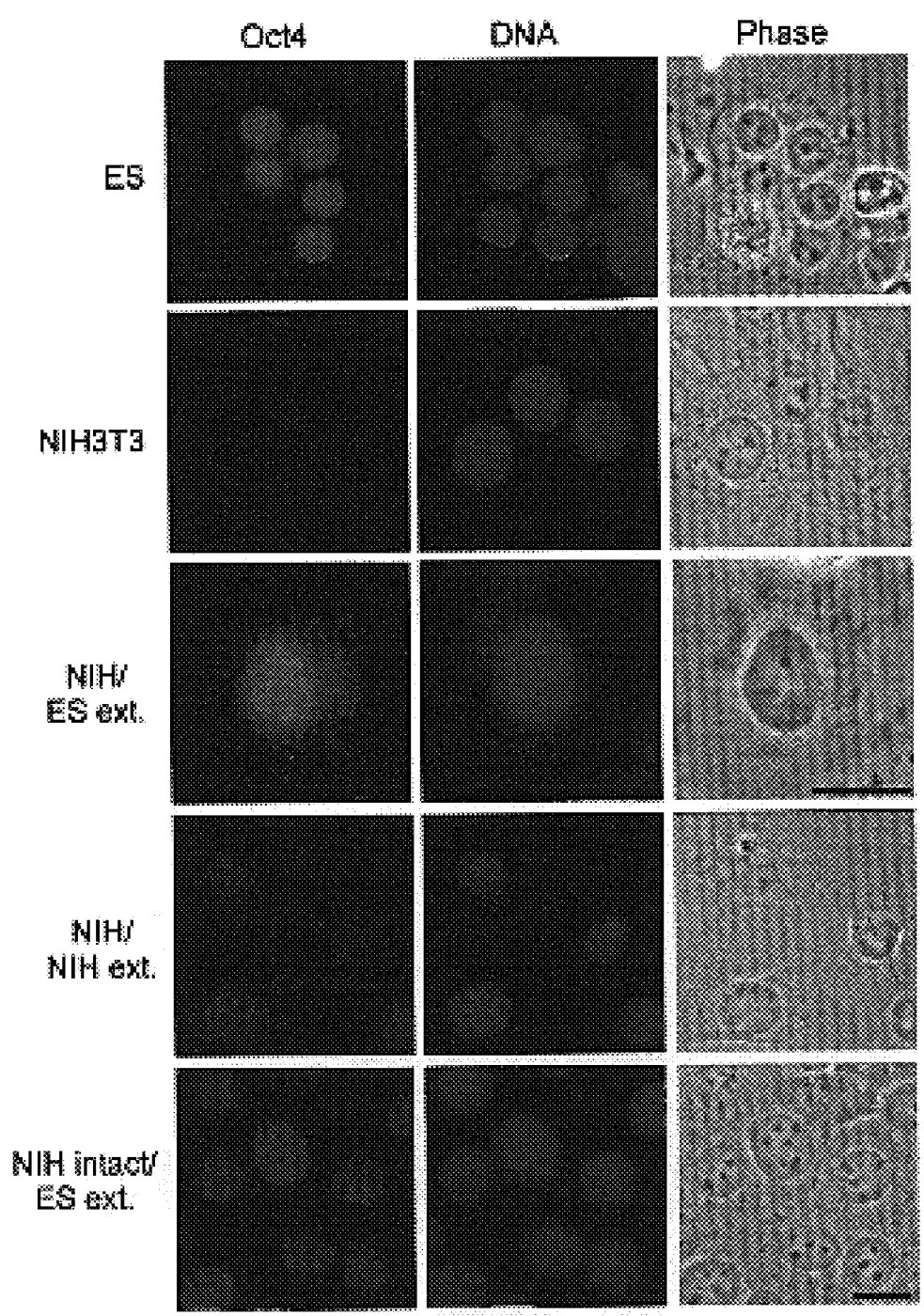
FIGS. 17A and 17B are pictures of the immunofluorescence and immunoblotting analysis, respectively, of Oct4 in NIH3T3 cells, embryonic stem cells and NIH3T3 fibroblasts reprogrammed in embryonic stem cell extract ("NIH/ES ext."; day-4 post-reprogramming). NIH3T3 cells exposed to a control NIH3T3 cell extract do not express Oct4 ("NIH/NIH ext.").

As a molecular marker of reprogramming, the reprogrammed cells were examined for the expression of Oct4, the product of the Oct4 gene. Oct4 expression is unique to germ cells, stem cells, preimplantation embryos, and the epiblast of the early post-implantation embryos. Therefore, Oct4 expression represents a useful marker for identification of pluri- or toti-potent cells. Oct4 expression was monitored four days after reprogramming by immunofluorescence using a commercially available anti-Oct4 antibody (Santa Cruz Biotechnology). For immunofluorescence analysis (Collas et al., J. Cell Biol. 135:1715-1725, 1996) cells were grown or cytospun onto poly-L-lysine coated glass cover slips, fixed with 3% paraformaldehyde (Sigma), and permeabilized with 0.1% Triton X-100 (Sigma) for 15 minutes. The proteins were blocked in 2% BSA in PBS/0.01% Tween-20 (PBST). Primary antibodies (anti-Oct4, 1:25 dilution) and FITC-conjugated anti-rabbit IgG secondary antibodies (1:250 dilution; Sigma) were incubated with cells for 30 minutes each. Cells were washed three times in PBS and mounted in anti-fade solution containing 0.1 µg/ml of the DNA stain, Hoechst 33342. FIG. 17A shows a clear anti-Oct4 labeling in input embryonic stem cells. As expected, NIH3T3 fibroblasts were not labeled (FIG. 17A). NIH3T3 cells reprogrammed in the embryonic stem cell extract exhibited anti-Oct4 labeling; in contrast, NIH3T3 cells exposed to a control NIH3T3 extract or intact NIH3T3 cells exposed to the embryonic stem cell extract (FIG. 17A) were not labeled with anti-Oct4. This result indicates that the reprogrammed cells express the embryonic stem cell-specific transcription factor, Oct4.

Figure 17B:
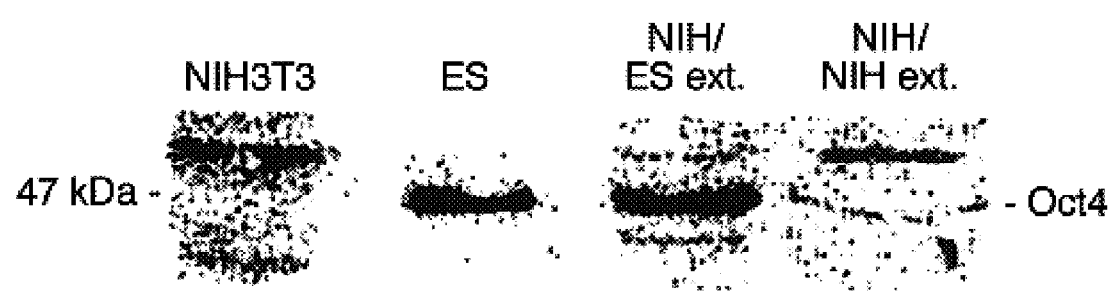
Figure 18:
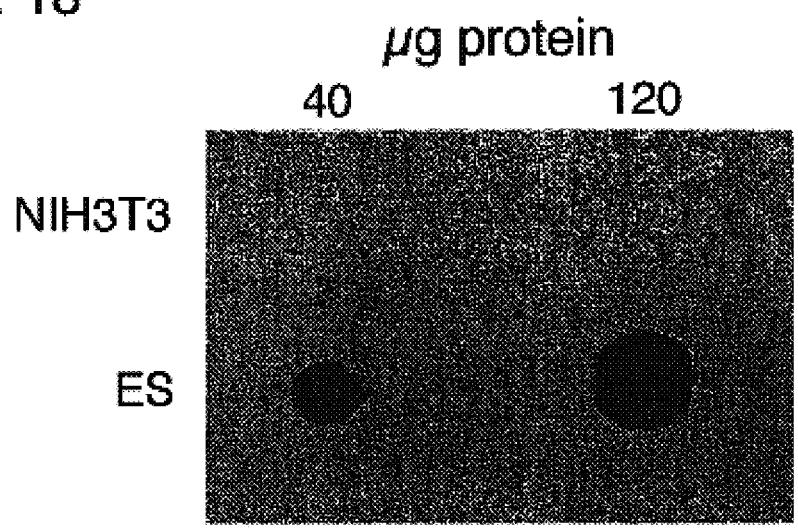
FIG. 18 is a picture of a membrane showing the detection of alkaline phosphatase activity in mouse embryonic stem cells. The top row contains lysates of NIH3T3 cells, and the bottom row contains lysates of embryonic stem cells. Two and 6 μl lysate were applied onto the membrane (protein concentration is ~20 μg/μl).
Figure 19:
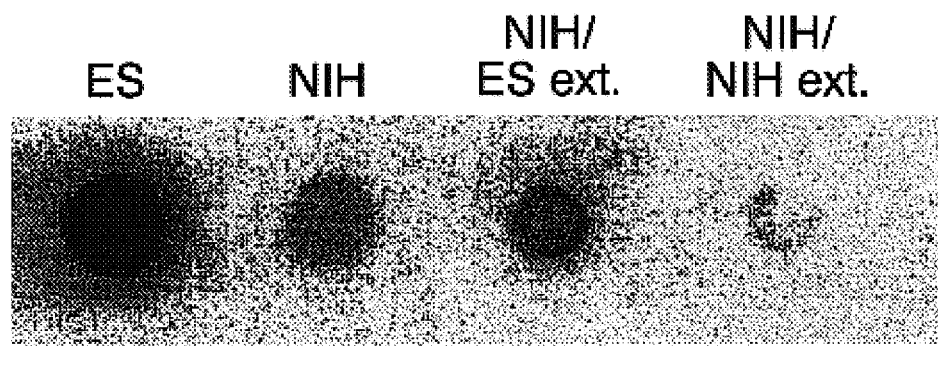
FIG. 19 is a picture of a membrane showing the detection of alkaline phosphatase activity in NIH3T3 cells reprogrammed in the embryonic stem cell extract.

Immunofluorescence observations were verified by Western blotting analysis. Immunoblotting analysis of cells was performed as described earlier (Collas et al., J. Cell Biol. 135:1715-1725,1996,). Briefly, cells were lysed in SDS-sample buffer, and the proteins were resolved by 10% SDS-polyacrylamide gel electrophoresis (PAGE) and electroblotted onto a nitrocellulose membrane. Membranes were incubated with affinity-purified rabbit polyclonal anti-Oct4 antibodies (Santa Cruz Biotechnology) for 1.5 hours, washed and incubated with HRP-conjugated secondary antibodies (anti-rabbit IgG, 1:5,000) for 1 hour. Blots were revealed by enhanced chemiluminescence (Amersham). FIG. 17B shows that while input NIH3T3 cells did not express Oct4 ("NIH"), NIH3T3 cells exposed to the embryonic stem cell extract expressed high levels of Oct4 ("NIH/ES ext."). The expression level was similar to that of embryonic stem cells used to prepare the extract (FIG. 17B, "ES"). Control NIH3T3 cells exposed to NIH3T3 cell extract did not express Oct4, as anticipated (FIG. 17B). 50,000 NIH3T3 cells and 10,000 embryonic stem cells and reprogrammed cells were used in the immunoblot shown in FIG. 17B. A novel, rapid, sensitive and semi-quantitative assay was developed to measure alkaline phosphatase, another embryonic stem cell marker, in embryonic stem cells and in the reprogrammed cells. The assay is based on spotting 1-2 µl (~20 µg protein per µl) of a Triton X-100 soluble lysate of embryonic stem cells, NIH3T3 cells exposed to NIH3T3 extract, intact-NIH3T3 cells exposed to embryonic stem cell extract, or of any cell of choice on a dry nitrocellulose membrane or on any other appropriate solid support. The test spot is of known protein concentration or from a known cell number to allow comparison to other spots. If desired, an aliquot containing a known amount of alkaline phosphatase or having a known level of alkaline phosphatase activity can also be spotted on the filter to form a reference spot. The membrane was wetted in Tris-buffered saline and drained. Alkaline phosphatase was detected by applying a detection solution normally designed to detect alkaline phosphatase-conjugated DNA probes on Southern blots (Alk-Phos Direct detection solution, Amersham). Alkaline phosphatase dephosphorylates a substrate contained in the detection solution, resulting in light emission. The membrane was drained and exposed to film. If the test sample is applied to a solid support other than a membrane, such as a 96-well plate, than either the 96-well plate is exposed to film or, it is exposed to a CCD camera to measure light emitted by the alkaline phosphate detection reaction. Alkaline phosphatase in the embryonic stem cell lysate, but not in the NIH3T3 cell lysate, resulted in the appearance of a light spot detected on the film (FIG. 18). Additionally, permeabilized NIH3T3 cells reprogrammed in embryonic stem cell extract, but not control cells, had alkaline phosphatase (FIG. 19).

The amount of alkaline phosphatase in the test spot can be determined by comparing the signal from the test spot to the signal from the reference spot or to the signal from a series of reference spots with increasing levels of alkaline phosphatase (e.g., forming a standard curve). The concentration of protein or the number of cells used to derive the test spot (e.g., the units of alkaline phosphatase mg protein) can be used to extrapolate the level of alkaline phosphatase in the original test cell or sample.

The reprogrammed cells were passaged and replated on day four using standard embryonic stem culture techniques, using LIF supplemented medium. Ten days after reprogramming, however, Oct4 expression levels were greatly reduced in the reprogrammed cells. The cells also lost the typical embryonic stem cell colony morphology they acquired after the reprogramming reaction. This result may be the result of either (i) transient reprogramming of the cells, i.e., the reprogramming factors are diluted out as the reprogrammed cells divide and are no longer active, (ii) spontaneous differentiation of the reprogrammed embryonic stem cells into fibroblasts, or (iii) loss of the truly reprogrammed embryonic stem cells such that contaminating non-reprogrammed fibroblasts outgrew the embryonic stem cells and remained in the culture. If desired, expression of Oct4 and other stem cell-specific proteins may be maintained in the reprogrammed cells for a longer period of time by performing multiple rounds of reprogramming. Moreover, the permeabilized cells can be exposed to the stem cell extract for a longer period of time during each round of reprogramming. Additional nuclear factors can also be added to the stem cell extract as described above to maximize reprogramming.

Collectively, these data indicate that NIH3T3 cells exposed to an embryonic stem cell extract acquire an embryonic stem cell phenotype, express Oct4, and express alkaline phosphatase.

If desired, the contribution of the reprogrammed ES cells to the three germ layers in mouse fetuses can be measured to further characterize the reprogrammed ES cells. For example, transgenic primary fetal ROSA26 mouse fibroblasts positive for the reporter gene, lacZ, coding for β-galactosidase (β-gal) can be reprogrammed as described above in an ES cell extract. Then, the reprogrammed cells are injected into mouse blastocysts. β-gal staining of sections of E7.5 embryos indicates where the reprogrammed cells are located. Additionally, because the ROSA26 mice are brown, reprogrammed fetal ROSA26 fibroblasts may be introduced into blastocysts of white (CD1) mice to produce chimeras. The production of brown-white chimeras indicates that the reprogrammed cells are incorporated into the individual. Control mock-reprogrammed cells introduced into blastocysts are not expected to contribute to the individual.

Because ES cells fused to mouse thymocytes have been previously reported to promote Oct4 expression and stable epigenetic change in the thymocyte nuclei, reprogrammed ES cells may also be tested to determine whether they contain any chromatin alterations. These studies should provide additional information on the stability and heritability of the changes initiated in the reprogrammed cells.

OTHER EMBODIMENTS

From the foregoing description, it will be apparent that variations and modifications may be made to the invention described herein to adopt it to various usages and conditions. Such embodiments are also within the scope of the following claims.

What is claimed is:

1. A method of reprogramming a cell to express a T-cell receptor (TCR) reactive with an antigen of interest, said method comprising the steps of:
   (a) incubating a permeabilized fibroblast cell with an interphase activated T-cell extract under conditions that result in TCR expression in said permeabilized fibroblast cell; and
   (b) selecting a cell that expresses a TCR reactive with an antigen of interest.

2. The method of claim 1, wherein said cell, following step (a), is incubated under conditions that allow the membrane of said cell to reseal.

3. The method of claim 1, wherein said permeabilized fibroblast cell of step (a) is further incubated with RNA or protein for a T-cell receptor reactive with said antigen of interest.

4. The method of claim 1, wherein said method further comprises, prior to step (a), incubating said permeabilized fibroblast cell with a mitotic cell extract under conditions that allow chromatin condensation and nuclear envelope breakdown in said permeabilized fibroblast cell.

5. The method of claim 1, wherein said permeabilized fibroblast cell is a permeabilized human fibroblast cell.

6. The method of claim 1 or 5, wherein said interphase activated T-cell extract is a human interphase activated T-cell extract.

7. The method of claim 1, wherein said permeabilized fibroblast cell is generated by incubating a fibroblast cell with streptolysin O.

* * * * *

UNITED STATES PATENT AND TRADEMARK OFFICE
CERTIFICATE OF CORRECTION

PATENT NO. : 7,491,534 B2  Page 1 of 1
APPLICATION NO. : 10/426595
DATED : April 14, 2009
INVENTOR(S) : Collas et al.

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 840 days Delete the phrase "by 840 days" and insert -- by 1,454 days --

Signed and Sealed this

Thirteenth Day of April, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,491,534 B2 | |
| APPLICATION NO. | : 10/426595 | |
| DATED | : February 17, 2009 | |
| INVENTOR(S) | : Collas et al. | |

It is certified that error appears in the above-identified patent and that said Letters Patent is hereby corrected as shown below:

Title Page, Item (56) under ASSIGNEE, replace "Kirin Holdings Kabushiki Kaisha,"
with --Kyowa Hakko Kirin CO. LTD.,--.

Title Page 3, Item (56) under OTHER PUBLICATIONS, in Lohka et al., 1983, replace
"Mitolic" with --Mitotic--.

Title Page 4, Item (56) under OTHER PUBLICATIONS, in Sotomaru et al., replace
"Endoculeated" with --Enucleated--.

Title Page 5, Item (56) under OTHER PUBLICATIONS, in Kikyo et al., replace
"Remondeling" with --Remodeling--.

Column 1, Line 15, replace "anandoned" with --abandoned--.

Column 4, Line 43, replace "produces an an antibody" with --produces an antibody--;

Line 46, replace "typrosine" with --tyrosine--.

Column 9, Line 6, replace "is a from" with --is from--.

Column 10, Line 15, replace "embodiment, cell" with --embodiment, the cell--.

Column 14, Line 22, replace "gain or loss" with --gain or lose--.

Column 16, Lines 47-48, replace "160-19-25, 1993" with --160:19-25, 1993--.

Column 18, Line 44, replace "aquired immune deficiency syndrom"
with --acquired immune deficiency syndrome--.

Signed and Sealed this
Tenth Day of January, 2012

David J. Kappos
*Director of the United States Patent and Trademark Office*

CERTIFICATE OF CORRECTION (continued)
U.S. Pat. No. 7,491,534 B2

Figure 6B:
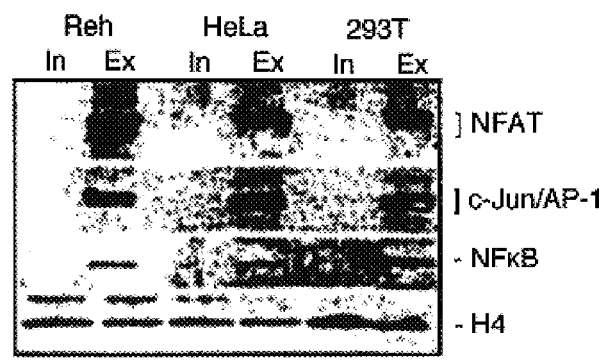
FIG. 6B in an illustration of an immunoblot showing the nuclear uptake of NFAT, c-Jun/AP1, and NFκB by these nuclei, as described for FIG. 3B.

Column 20, Line 15, replace "FIG. 6B in an" with --FIG. 6B is an--.

Column 21, Line 22, replace "Microccocal" with --Micrococcal--.

Column 22, Line 10, replace "intranucleuear" with --intranuclear--;

Line 51, replace "293t" with --293T--;

Line 62, replace "housekeeping gens" with --housekeeping genes--;

Line 66, replace "293t" with --293T--.

Column 28, Line 25, replace "hi stone" with --histone--.

Column 38, Line 63, replace "association. And Erk" with --association, and Erk--.

Figure 11A:
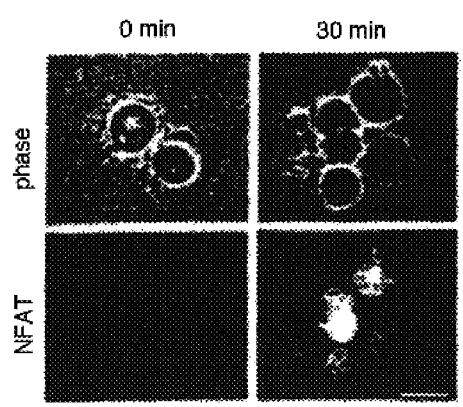
FIGS. 11A-11C demonstrate the nuclear import and chromatin binding of transcriptional activators of the IL-2 gene in 293T fibroblast nuclei exposed to stimulated T-cell extract.
Figure 11B:
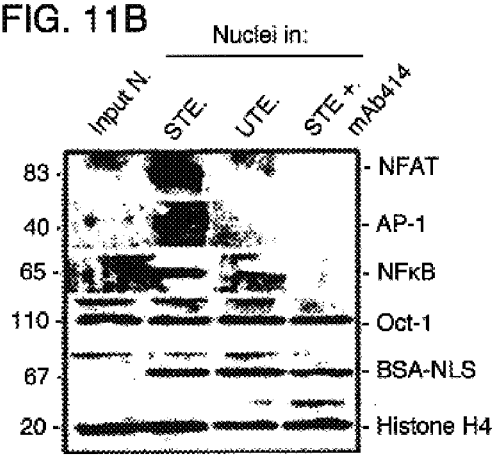
Figure 11C:
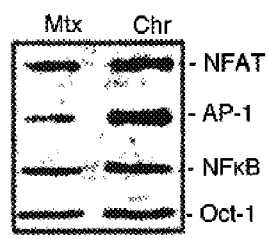

Column 39, Line 20, replace "(FIGS. 1A and 11B)" with --(FIGS. 11A and 11B0--.

Column 41, Line 11, replace "microccocal" with --micrococcal--;

Line 12, replace "DNA to from" with --DNA from--.

Column 46, Line 18, replace "phosphorscreen" with --phosphor screen--;

Lines 31-32, replace "house keeping" with --housekeeping--;

Line 35, replace "293t" with --293T--;

Line 64, replace "phorbolmyristylacetate" with --phorbol myristyl acetate--.

Column 48, Line 59, replace "One in three experiment" with --One in three experiments--;

Line 60, replace "one in five experiment" with --one in five experiments--.

Column 50, Line 30, replace "buffey coats" with --buffy coats--;

Line 31, replace "buffey coat" with --buffy coat--;

Line 40, replace "ReprogrammedT-Cells" with --Reprogrammed T-Cells--;

Line 57, replace "produced" with --produce--.

CERTIFICATE OF CORRECTION (continued)
U.S. Pat. No. 7,491,534 B2

Column 52, in TABLE 1-continued, under Associated Cancer,
    Line 23, replace "Colorectalcarcinoma" with --Colorectal carcinoma--.

Column 55, Line 56, replace "eptitopes" with --epitopes--.

Column 56, Line 29, replace "Sreptolysin O" with --Streptolysin O--;

Line 49, replace "(non-permeabilizied) with --(non-permeabilized)--.